United States Patent
Geisert et al.

(10) Patent No.: US 9,216,024 B2
(45) Date of Patent: *Dec. 22, 2015

(54) SYSTEM AND METHOD FOR AN INTERVERTEBRAL IMPLANT

(75) Inventors: Christophe Geisert, Huefingen (DE); Thierry Marnay, Castelnau le Lez (FR); Rudolf Bertagnoli, Vienna (AT); Eduard Kufeld, Tuttlingen (DE); Barbara Schweizer, Sulz am Neckar (DE); Stephan Eckhof, Rielheim-Wellheim (DE)

(73) Assignee: DePuy Synthes Products, Inc., Raynham, MA (US)

( * ) Notice: Subject to any disclaimer, the term of this patent is extended or adjusted under 35 U.S.C. 154(b) by 1439 days.

This patent is subject to a terminal disclaimer.

(21) Appl. No.: 11/575,790

(22) PCT Filed: Sep. 16, 2005

(86) PCT No.: PCT/IB2005/053051
§ 371 (c)(1), (2), (4) Date: Nov. 17, 2008

(87) PCT Pub. No.: WO2006/033067
PCT Pub. Date: Mar. 30, 2006

(65) Prior Publication Data
US 2009/0216330 A1    Aug. 27, 2009

Related U.S. Application Data

(63) Continuation of application No. 10/947,661, filed on Sep. 23, 2004, now Pat. No. 7,763,024, and a
(Continued)

(30) Foreign Application Priority Data

Jun. 22, 2005 (WO) .................. PCT/IB2005/052041

(51) Int. Cl.
*A61F 2/44* (2006.01)
*A61B 17/00* (2006.01)
(Continued)

(52) U.S. Cl.
CPC .......... *A61B 17/1671* (2013.01); *A61B 17/1604* (2013.01); *A61B 2019/303* (2013.01); *A61B 2019/462* (2013.01)

(58) Field of Classification Search
CPC ........... A61B 17/1671; A61B 17/1604; A61B 2019/303
USPC ......... 606/79, 84, 86 R, 99; 623/17.11–17.16
See application file for complete search history.

(56) References Cited

U.S. PATENT DOCUMENTS 4,239,045 A   12/1980   Schlein
4,349,921 A   9/1982   Kuntz
(Continued)

FOREIGN PATENT DOCUMENTS

DE         100 35 182      2/2002
DE   20 2004 003 750      5/2004
(Continued)

OTHER PUBLICATIONS

Brochure "Prodisc-L", publication designation SMT 001 G-03/03.
(Continued)

*Primary Examiner* — Christopher Beccia
(74) *Attorney, Agent, or Firm* — Baker & Hostetler LLP

(57) ABSTRACT

The invention relates to the preparation of an intervertebral space with a trial implant (9), the insertion of an implant (5, 6, 7), the inserters (13, 16), and the method for feeding and inserting the implant (5, 6, 7) by means of an oblique anterior approach. In the novel improved method, the associated instruments (13, 16) for inserting an implant (5, 6, 7) into an intervertebral space, in particular for the lumbar spine at an oblique anterior angle of 45° was developed, the left side of the body being preferred for insertion of the implant (5, 6, 7). Either the implant (5, 6, 7) can be inserted all in one, or first the upper part (5) and lower parts (7) and then the inlay (6) may be inserted. By insertion by means of the left oblique anterior approach at 45°, optimum utilization of the area of the intervertebral space is ensured (footprint), and better retention of the implant is guaranteed by the exact chiselling at an angle of 90° normal to the respective intervertebral surface.

62 Claims, 56 Drawing Sheets

Related U.S. Application Data continuation of application No. 10/996,797, filed on Nov. 26, 2004, now Pat. No. 7,780,731.

(60) Provisional application No. 60/640,106, filed on Dec. 30, 2004.

(51) Int. Cl.
*A61B 17/58* (2006.01)
*A61B 17/16* (2006.01)
*A61B 19/00* (2006.01)

(56) References Cited

U.S. PATENT DOCUMENTS

| | | |
|---|---|---|
| 4,759,766 A | 7/1988 | Buettner-Janz et al. |
| 4,772,287 A | 9/1988 | Ray et al. |
| 4,827,928 A | 5/1989 | Collis, Jr. |
| 4,881,534 A | 11/1989 | Uhl et al. |
| 4,904,260 A | 2/1990 | Ray et al. |
| 5,135,528 A | 8/1992 | Winston |
| 5,167,725 A | 12/1992 | Clark et al. |
| 5,314,477 A | 5/1994 | Marnay |
| 5,397,364 A | 3/1995 | Kozak et al. |
| 5,423,825 A | 6/1995 | Levine |
| 5,507,816 A | 4/1996 | Bullivant |
| 5,562,736 A | 10/1996 | Ray et al. |
| 6,261,293 B1 | 7/2001 | Nicholson et al. |
| 6,261,295 B1 | 7/2001 | Nicholson et al. |
| 6,315,797 B1 | 11/2001 | Middleton |
| 6,325,827 B1 | 12/2001 | Lin |
| 6,368,350 B1 | 4/2002 | Erickson et al. |
| 6,413,278 B1 | 7/2002 | Marchosky |
| 6,478,801 B1 | 11/2002 | Ralph et al. |
| 6,478,822 B1 | 11/2002 | Leroux et al. |
| 6,485,495 B1 | 11/2002 | Jenkinson |
| 6,517,544 B1 | 2/2003 | Michelson |
| 6,575,899 B1 | 6/2003 | Foley et al. |
| 6,599,291 B1 | 7/2003 | Foley et al. |
| 6,607,558 B2 | 8/2003 | Kuras |
| 6,610,089 B1 | 8/2003 | Liu et al. |
| 6,626,943 B2 | 9/2003 | Eberlein et al. |
| 6,635,060 B2 * | 10/2003 | Hanson et al. .................. 606/79 |
| 1,295,578 A1 | 11/2003 | O'Neil |
| 6,641,582 B1 | 11/2003 | Hanson et al. |
| 6,641,613 B2 | 11/2003 | Sennett |
| 6,645,248 B2 | 11/2003 | Casutt |
| 6,648,895 B2 | 11/2003 | Burkus et al. |
| 6,656,224 B2 | 12/2003 | Middleton |
| 1,283,026 A1 | 1/2004 | Patel et al. |
| 6,676,703 B2 | 1/2004 | Biscup |
| 6,679,886 B2 | 1/2004 | Weikel et al. |
| 6,682,562 B2 | 1/2004 | Viart et al. |
| 1,384,455 A1 | 4/2004 | Fraser et al. |
| 6,719,760 B2 | 4/2004 | Dorchak et al. |
| 6,770,074 B2 | 8/2004 | Michelson |
| 6,793,678 B2 | 9/2004 | Hawkins |
| 6,802,863 B2 | 10/2004 | Lawson et al. |
| 6,824,565 B2 | 11/2004 | Muhanna et al. |
| 6,830,570 B1 | 12/2004 | Frey et al. |
| 6,835,208 B2 | 12/2004 | Marchosky |
| 6,875,222 B2 | 4/2005 | Long et al. |
| 6,936,071 B1 | 8/2005 | Marnay et al. |
| 6,966,929 B2 | 11/2005 | Mitchell |
| 6,994,727 B2 | 2/2006 | Khandkar et al. |
| 7,004,971 B2 | 2/2006 | Serhan et al. |
| 7,011,684 B2 | 3/2006 | Eckman |
| 7,018,416 B2 | 3/2006 | Hanson et al. |
| 7,025,787 B2 | 4/2006 | Bryan et al. |
| 7,037,340 B2 | 5/2006 | Gau |
| 7,048,764 B2 | 5/2006 | Ferree |
| 7,118,580 B1 | 10/2006 | Beyersdorff et al. |
| 7,153,325 B2 * | 12/2006 | Kim et al. .................. 623/17.15 |
| 7,160,304 B2 | 1/2007 | Michelson |
| 7,169,183 B2 | 1/2007 | Liu et al. |
| 7,204,851 B2 | 4/2007 | Trieu et al. |
| 7,204,852 B2 | 4/2007 | Marnay et al. |
| 7,503,934 B2 * | 3/2009 | Eisermann et al. ......... 623/17.15 |
| 7,749,271 B2 * | 7/2010 | Fischer et al. ............. 623/17.11 |
| 7,905,921 B2 * | 3/2011 | Kim et al. .................. 623/17.16 |
| 8,114,163 B2 * | 2/2012 | Berelsman et al. ......... 623/20.11 |
| 2002/0128715 A1 | 9/2002 | Bryan et al. |
| 2003/0083747 A1 | 5/2003 | Winterbottom et al. |
| 2003/0139812 A1 | 7/2003 | Garcia et al. |
| 2003/0195517 A1 | 10/2003 | Michelson |
| 2003/0195520 A1 | 10/2003 | Boyd et al. |
| 2003/0195629 A1 | 10/2003 | Pafford et al. |
| 2003/0195631 A1 | 10/2003 | Ferree |
| 2004/0010316 A1 | 1/2004 | William et al. |
| 2004/0024462 A1 | 2/2004 | Ferree et al. |
| 2004/0133278 A1 | 7/2004 | Marino et al. |
| 2004/0148027 A1 | 7/2004 | Errico et al. |
| 2004/0158254 A1 | 8/2004 | Eisermann |
| 2004/0158326 A1 * | 8/2004 | Ralph et al. ................ 623/17.11 |
| 2004/0199168 A1 | 10/2004 | Bertagnoli et al. |
| 2004/0215198 A1 | 10/2004 | Marnay et al. |
| 2004/0220670 A1 * | 11/2004 | Eisermann et al. ......... 623/17.14 |
| 2004/0243241 A1 | 12/2004 | Istephanous et al. |
| 2004/0260286 A1 | 12/2004 | Ferree |
| 2005/0021040 A1 | 1/2005 | Bertagnoli |
| 2005/0065611 A1 | 3/2005 | Huppert et al. |
| 2005/0267581 A1 | 12/2005 | Marnay et al. |
| 2006/0030862 A1 | 2/2006 | De Villiers et al. |
| 2006/0167461 A1 | 7/2006 | Hawkins et al. |
| 2006/0293754 A1 | 12/2006 | De Villiers et al. |

FOREIGN PATENT DOCUMENTS

| | | |
|---|---|---|
| EP | 0 637 439 | 2/1995 |
| EP | 1 259 175 | 7/2004 |
| WO | WO-01/15637 | 3/2001 |
| WO | WO-02/065957 | 8/2002 |
| WO | WO-03/084449 | 10/2003 |
| WO | WO-2004/041131 | 5/2004 |
| WO | WO-2004/080355 | 9/2004 |

OTHER PUBLICATIONS

Brochure "Prodisc-L", publication designation SMT014-04/04.
Brochure "Prodisc-C", publication designation SMT013-04/04.
Brochure PRODISC® "Retrospective Clinical Study: 7 to 11 Year Follow-Up", publication No. SMT 002E-03/06.
Product of Medtronic—"Maverik".

* cited by examiner

Fig.45
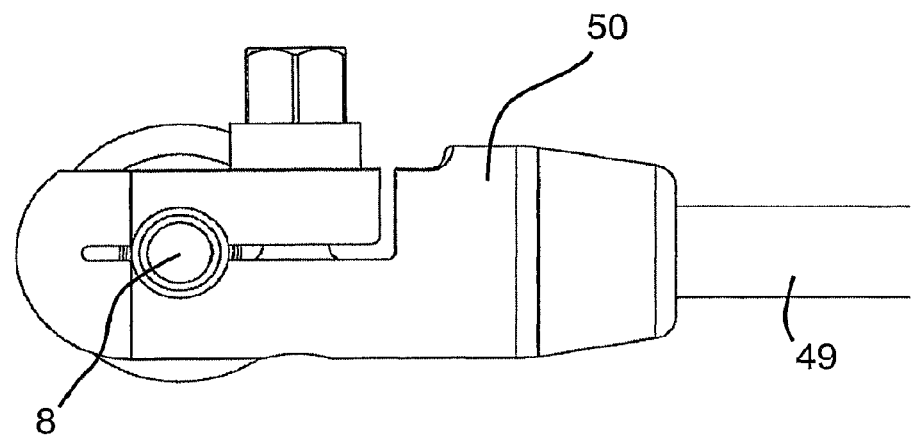
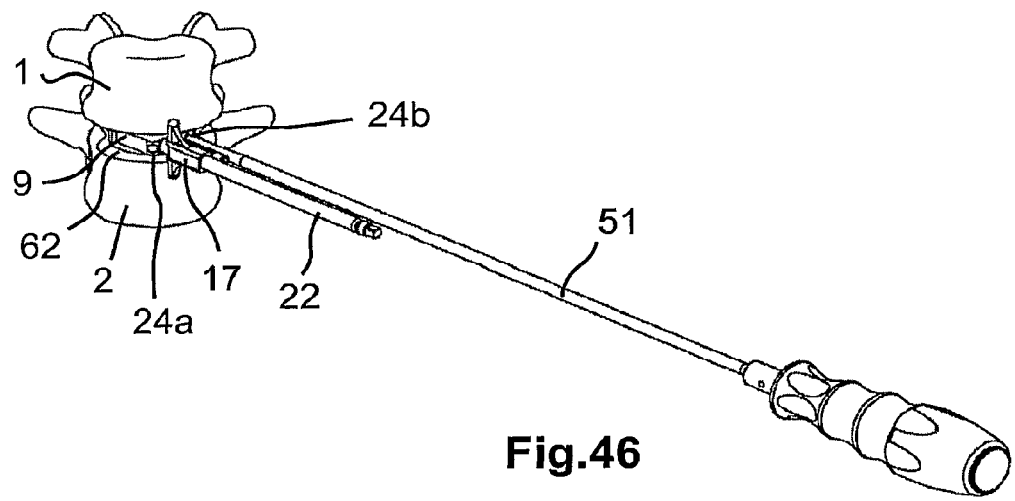
Fig.46

SYSTEM AND METHOD FOR AN INTERVERTEBRAL IMPLANT

CROSS-REFERENCE TO RELATED APPLICATIONS

This application is a continuation of U.S. Ser. No. 10/947,661 filed in U.S. on Sep. 23, 2004, U.S. Ser. No. 10/996,797 filed in U.S. on Nov. 26, 2004 of the U.S. Provisional Application U.S. Ser. No. 60/640,106 filed in U.S. on Dec. 30, 2004 and of PCT/IB2005/052041 filed in Geneva on Jun. 22, 2005, the entire contents of which are hereby incorporated herein by reference.

TECHNICAL FIELD OF THE INVENTION

The invention relates to a system and method for an intervertebral implant, in detail a trial implant for the preparation of an intervertebral space for insertion of an intervertebral disc prosthesis, to an implant for insertion into this prepared intervertebral space; to a chisel for use with an implant or a trial implant for preparation of the intervertebral space, to a pre-trial implant for radiographic and geographic orientation in the intervertebral space; to a device for keeping an intervertebral space open for discectomy and/or for the insertion of an implant, trial implant or pre-trial implant; to a mounting instrument for mounting an intervertebral disc implant having a superior and inferior implant plate and an inlay; to an inserter for inserting a trial implant or an implant into the intervertebral space; and to a method for positioning and fixing an intervertebral implant in the intervertebral space.

DESCRIPTION OF THE PRIOR ART

Implants having at least one upward- or downward-projecting keel are frequently used as intervertebral implants. For receiving at least one keel of an implant in the superior or inferior vertebra, a groove is usually chiselled by means of a chisel for each keel. A pre-trial implant or a trial implant can be used in the intervertebral space in the conventional manner for radiologic or spatial orientation. In order to keep an intervertebral space open for discectomy and/or for insertion of an implant, trial implant or pre-trial implant, struts are customarily used and are mounted on the outside of the vertebra.

Known implants for insertion and the method for direct oblique anterior preparation of an intervertebral space have been publicized under the name Prodisc® (brand of Spine Solutions) both for the lumbar spinal region and for the cervical spine region and have been successfully launched on the market.

Under the title "Instrument and Method for preparing an intervertebral space for receiving an artificial disc implant", patent applications related to the tools or instruments and the method for the preparation of an intervertebral space for insertion of an artificial disc implant directly from the anterior were filed on 2003-04-03 as U.S. application Ser. No. 10/023,879 and subsequently as PCT/US04/12664. The intervertebral implant Prodisc® currently on the market corresponds substantially to the content of this patent application.

Furthermore, patent applications related to the instruments required for Prodisc® and the method for insertion of the intervertebral implant were filed with title "Instruments and method for inserting an intervertebral implant" on 2003-07-02 as U.S. application Ser. No. 10/622,803 and subsequently as PCT/US04/22608. The Prodisc® system corresponds substantially to the content of the patent application.

Prodisc® is described in the brochures of Spine Solutions as "Cervical Total Disc Replacement" for the cervical spinal region and as "Lumbar Total Disc Replacement" for the lumbar spinal region:

Brochure "Prodisc-L", with the publication designation SMT 001 G-03/03 and also SMT014-04/04 describes how the form and function of an intervertebral disc can be substantially restored by insertion of an intervertebral disc prosthesis from the anterior.

The instruments required for this purpose and the surgical technique are described:
creation of an access to the two affected vertebrae;
removal of the intervertebral disc (discectomy) from the intervertebral region;
determination of the implant size, implant height, angle of lordosis and implant position by means of a trial implant by the exact central orientation thereof with radiographic monitoring;
precutting of grooves simultaneously from above and below, directly from the anterior direction, by means of a fork-shaped double chisel guided in the trial implant;
insertion of the upper (superior) and lower (inferior) implant plates, the inferior and the superior plates simultaneously being mounted in the predetermined position without distraction.
With the aid of an inserter, the two adjacent vertebrae are forced apart and
by means of a pusher the PE inlay is pushed into the inferior plate and securely locked;
the instruments are removed and the final implant position is checked by means of radiographic monitoring.

Brochure "Prodisc-C", with the publication designation SMT013-04/04, describes how the form and function of a cervical spine is substantially restored by insertion of a cervical intervertebral disc prosthesis:
First, fixation of the cervical vertebra to a holder by means of screws and subsequently discectomy are carried out, and the intervertebral space is held apart by means of a spreading forceps.
A trial implant having an adjustable stopper is inserted, and, guided by a fork-like chisel, a groove is then simultaneously chiselled directly from the anterior direction into the superior and inferior cervical vertebrae.
The already completely assembled implant is then inserted into the cervical intervertebral space by means of a special inserter.

In the brochure PRODISC® "Retrospective Clinical Study: 7 to 11 Year Follow-Up" published with the number SMT 002E-03/06, the aims, the method and the results of these implant techniques are summarized with a conclusion:
All implants (61 out of 64) which were inserted within a period of 7-11 years were intact and functioned properly.
There was a substantial reduction in back pain and leg pain, and 92.7% of the patients were very satisfied with the insertion of the prosthesis.
Both Prodisc® products and the associated instruments have already been tested and have been very well accepted by the patient. The mobility of the spine was completely restored in many cases.

Also known is PCT publication WO-2004/080355A1 "Articular disc prosthesis for anterior-oblique insertion", which describes an intervertebral disc prosthesis for anterior/lateral-oblique insertion. A product of Medtronic "Maverik" corresponds to an embodiment of this published Patent Application. "Maverik" is an intervertebral disc prosthesis which—after corresponding preparation of the intervertebral space—can be inserted from the oblique anterior/lateral direction at an angle of 30°.

This PCT publication WO-2004/080355 teaches that insertion can be effected from the lateral direction. In the case of the insertion direction chosen for "Maverik", however, the fact that lateral insertion leads to a change of the footprint, i.e. to a change of the sagittally visible base surface of the implant, was overlooked. In comparison with known implants which permit oblique anterior insertion, "Maverik" is smaller and approximately triangular. This is evidently associated with its insertion direction of 30°. However, a smaller footprint means in certain circumstances poorer anchorage of the prosthesis in the vertebra. On consideration of the PCT publication together with "Maverik", a person skilled in the art would, however, therefore generally be discouraged from choosing an oblique anterior/lateral access. The footprint reduction and poorer fixing associated therewith appear seriously disadvantageous to a person skilled in the art.

Furthermore, publication WO-2004/080355A1, at FIG. 40 showed a figure with an angle of about 52° to the AP direction, measured from the figure. In publication WO-2004/080355A1, this angle is about 37° in FIG. 44*a*. The fact that Medtronic, which is associated with SDGI, actually markets and delivers its product "Maverik" with only 30° is understood by the person skilled in the art to teach departure from the originally disclosed access angle of about 52° through about 37° to 30°. To the person skilled in the art, however, this means that the implant area must be reduced in order to bypass the vessels without risk of injury (oblique access). This is the teaching of this WO publication in conjunction with the product "Maverik".

Evidently, in the choice of the angle at the time of the development of Maverik, the persons skilled in the art did not regard an angle between 52° and 37° as optimal, but rather an angle of about 30° which is not even described in WO-2004/080355A1, and accepted the effect with footprint reduction.

Another patent publication, EP1259175B1, relates to "Instruments for disc space preparation". It discloses a medical instrument for the preparation of an intervertebral space between adjacent vertebrae of a patient. A cutting edge guide is designed so that it has a distraction holder for maintaining distraction between the two vertebrae. A blade channel has a guide channel which is designed so that it can receive a guide rib at or on a cutting edge in order to maintain the orientation of the cutting edge relative to the holder and hence relative to the vertebrae.

U.S. published application no. 20040199168 discloses instruments and methods for the positioning of one or more implants in a spinal intervertebral space. The instruments and methods are designed for oblique insertion laterally relative to the intervertebral space. The instruments include a distractor, and a guide to permit positioning of one or more implants in the intervertebral space.

SUMMARY OF THE INVENTION

One object of the invention is the provision of novel intervertebral implants, of a novel improved method and of the associated instruments or of devices for the preparation of an intervertebral space and for the insertion of an intervertebral implant, in particular for the lumbar spine.

According to another object, the method of the invention is intended to permit oblique anterior/lateral insertion at an angle of about 45°, in particular left oblique-anterior insertion, viewed from the patient.

A trial implant according to a version of the invention may be inserted into a prepared intervertebral space. It serves for determining the size and position of the implant to be inserted. The trial implant may be oriented radiographically by means of sighting slots according to the invention, and simultaneously serves as a guide for a chisel. A chisel may be used for chiselling, into the intervertebral surface of the superior and inferior vertebrae, a respective groove each of which is normal to the intervertebral surface so that an implant insertable in exchange for the trial implant and having a corresponding keel rests as flat as possible on the vertebral surface. The trial implant has a superior and an inferior contact surface with at least one guide slot each which guides the chisel in at least two directions in space.

The keel of the implant may be fixed thereto or, according to a version which may be used independently of the above, may be mounted rotatably relative to the contact surface, with subsequent fixing in the contact surface.

According to a version of the invention, the chisel is in the form of a mono-chisel, and is guided in the trial implant or in the implant. For the preparation of the intervertebral space, in particular for radiographic and spatial orientation in the intervertebral space, a pre-trial implant according to the invention may also be used.

In order to keep the intervertebral space open for a discectomy and/or for insertion of an implant or trial implant, leaf-like struts according to the invention are used and are inserted in the proximal area of the intervertebral space-preferably to the side of a trial implant—and run in a wedge shape at the angle of lordosis and may be curved medially at their medial end in order to improve the vision of the operating area. These novel struts may also be used independently of the above. The struts may be individual struts which can be inserted into the intervertebral space. For mounting of an intervertebral disc implant with a superior and inferior implant plate and an inlay according to the invention, a mounting instrument is used by means of which the exactly fitting implants may be assembled from a group of implant plates and inlays directly in the operating theatre. In a certain embodiment of the invention, an inserter according to the invention for the trial implant or for the implant serves for the insertion into the intervertebral space. The positioning and fixing of the intervertebral implant or of the trial implant for preparation is effected in the intervertebral space preferably at an oblique anterior, in particular left oblique anterior, angle, according to the invention at an angle of about 45° to the medial plane (anterior-posterior plane), viewed from the patient.

According to a version of the invention, a special assembly device, by means of which the inlay can be placed in the correct position in the implant plate or locked with it, is used for assembly of the implant.

According to a version of the method of the invention, an inserter is used for inserting the trial implant or the implant, it has a retaining mechanism for an implant collet, which is passed through a rod to an actuating part having a locking lever by means of which the implant can be held or released. According to a version of the invention, the implant can be inserted all in one, or first the upper and lower part followed by the inlay. Before and during the insertion, the intervertebral space is held open by the struts according to the invention.

In a preferred version, the invention starts from an optimum "footprint" with an insertion direction of about 45° giving de facto this abrupt improvement effect at 45° with the largest possible footprint in spite of anterior/lateral access.

Some particular advantages resulting from the oblique insertion at about 45°:

The main blood vessels running on the anterior side of the spine are less extended during the operation;

this results in easier access than the direct oblique anterior access.

It makes it possible to bypass the complex vessel structure (stomach/intestine) which is present directly in front of the vertebrae.

Although the lateral approach is already known per se through "Maverik", the insertion angle there is 30° relative to the anterior-posterior plane. However, owing to the disadvantage of the footprint reduction of this known lateral insertion method, the inventors were discouraged from applying it further since they attached considerable importance to the footprint size or the optimum adhesion between the vertebrae and the implant.

Through inventive considerations and experiments on the part of the inventors, it was surprisingly found that an insertion angle of about 45° during insertion of the implant proves to be optimum with regard to the best possible footprint—with a simultaneously advantageous access.

According to a version of the invention, particular attention is also devoted to the preparation of the intervertebral space by means of a trial implant and the exact chiselling of the groove for receiving the implant keel at 90° to the respective intervertebral surface. This ensures very good retention of the implant.

Although the drawings also show the preferred embodiments, neither the drawings nor the description are to be interpreted as being restricted. On the other hand, contents of the drawings and of the description as well as the contents of the patent claims belong to the disclosure of the invention in this patent application. These and other features, aspects, and advantages of the present invention will become better understood with regard to the following description, appended claims, and accompanying drawings.

For better preparation for an intervertebral disc prosthesis, a novel trial implant was developed for the preparation of the intervertebral space, having a superior and inferior bearing surface and having one guide slot each in the superior and inferior bearing surface, at least one of the guide slots being formed in such a way that an insertable or inserted guide can be held or is held nondisplaceably in two directions in space—in particular parallel and normal to the respective bearing surface. A movement of a guide in the longitudinal direction relative to the guide slot is thus possible. Owing to the novel formation according to the invention, for example, the use of a monochisel instead of a fork-like chisel is possible. However, this novel guide slot in the trial implant also makes it possible to locate other tools and devices relative to the trial implant.

A further development of the trial implant in which the guide slot serves for guiding the chisel is characterized in that the chisel is in the form of a monochisel which is connected to a guide which is displaceable relative to it and is formed diametrically oppositely to the respective guide slot. The guide projects beyond the chisel in the longitudinal direction. The guide thus permits the positioning of the chisel relative to the trial implant and hence to the vertebra even before it touches the vertebra.

According to a particular further development of the invention, the two guide slots (one each in the superior and in the inferior implant plate) are in different three-dimensional positions relative to one another (angle β). This makes it possible for the trial implant in cooperation with the chisel to enable preparation of a groove from the oblique anterior/lateral direction. It is also possible to provide a plurality of guide slots per plate.

A development according to the invention which is independent of the above and of course may also preferably be used together therewith relates to a trial implant for the preparation of an intervertebral space for use of an intervertebral disc prosthesis, having a superior and inferior bearing surface and having at least one groove each in the superior and inferior bearing surface, at least one of the grooves being in the form of a sighting slot so that, in the case of a trial implant inserted into an intervertebral space under radiographic monitoring, it enables detection of the position thereof relative to the vertebra. This ensures in a simple manner that a surgeon can perform the correct orientation of the trial implant under radiographic monitoring, and the subsequent position of the implant can thus be well prepared.

This is particularly simplified if the sighting slot is at that angle (?) or at a complementary angle (d) to the respective guide slot, which corresponds to the surgical approach angle (e) or the direction of insertion of the implant into the intervertebral space for the implantation of an intervertebral disc prosthesis.

In order to permit an all round positioning check by means of X-rays guided by a C-arc, a further development provides, per bearing surface, two sighting slots which are at a right angle to one another.

In principle, all materials tolerated by the body are available for the choice of material, but it is advantageous if the trial implant is composed of X-ray-opaque or X-ray visible material. In the case of this design, the sighting slots are as a rule produced by milling and are open to the outside. However, they can also be filled with X-ray-transparent material, for example plastic. The trial implant can thus also be plastic-coated (e.g. polyethylene), which permits an integrated surface and improved sliding properties on the insides of the vertebrae.

Alternatively, the trial implant may also be composed of X-ray-transparent material, X-ray-opaque or X-ray-visible inlays being provided instead of the sighting slots. In the case of this alternative design, the X-ray visibility effect or the positioning aid is further simplified if the guide slots, too, are X-ray-visible.

An invention which is independent of the above but which is preferably used together with the above constructions comprises providing, on the lateral surface, at least one impact hollow for the engagement of an impact bar in the case of a trial implant for the preparation of an intervertebral space for insertion of an intervertebral disc prosthesis, having a superior and inferior bearing surface and having a lateral surface. These novel impact hollows permit secure attachment of impact bars guided by the surgeon's hand. A trial implant can thus be precisely positioned.

According to a further development, a guide shank intended for engagement of an impact shank or handle likewise serves for positioning and also for removal of a positioned trial implant according to one of the preceding designs.

According to a further embodiment, an adjustable stop serves for limiting the depth of penetration of a trial implant into the intervertebral space.

According to the novel insertion method according to the invention, the trial implant is preferably formed for insertion from about 45° relative to the medial plane (anterior-posterior plane) between two vertebrae.

The invention also comprises a novel implant for use as an intervertebral disc prosthesis in an intervertebral space, having a superior and inferior bearing surface and having at least one guide slot each in the superior and inferior bearing surface, at least one of the guide slots being formed in such a way that an insertable or inserted guide can be held or is held nondisplaceably in two directions in space—in particular parallel and normal to the respective bearing surface. Such an implant makes it possible to avoid the use of a trial implant and thus to accelerate the operation process. However, its use will require even further tests so that the application is currently not yet preferred. In any case, this guide slot—as in the trial implant—may serve for guiding a chisel, the chisel being in the form of a monochisel which is connected to a guide which is displaceable relative to it and is formed diametrically opposite to the respective guide slot and projects longitudinally beyond the blade of the chisel.

As in the case of the trial implant, the two guide slots may be in a different three-dimensional position relative to one another (angle β).

The invention also comprises a novel implant for use as an intervertebral disc prosthesis in an intervertebral space and for the preparation of the intervertebral space, having a superior and inferior bearing surface and having at least one groove each in the superior and inferior bearing surface, at least one of the grooves being in the form of a sighting slot so that, in the case of an implant inserted into an intervertebral space, said groove enables its position relative to the vertebrae to be detected radiographically.

This is particularly simplified if the sighting slot is at that angle (?) or at a complementary angle (d) to the respective guide slot which corresponds to the surgical approach angle (e) or the direction of insertion of the implant into the intervertebral space for the implantation of the intervertebral disc prosthesis. In order to permit all round positioning guided in the form of an arc, two sighting slots, which are at a right angle to one another, are provided per bearing surface.

In principle, all materials tolerated by the body are available for the choice of material, but it is advantageous if the implant is composed at least partly of X-ray-opaque or X-ray-visible material. Instead of the sighting slots, X-ray-opaque or X-ray-visible inlays may be provided, the guide slots being X-ray visible.

In a further embodiment of an implant according to the invention for use as an intervertebral disc prosthesis in an intervertebral space and for the preparation of an intervertebral space for use of an intervertebral disc prosthesis, having a superior and inferior bearing surface and having a lateral surface, at least one impact hollow for engagement of an impact bar is provided on the lateral surface. These novel impact hollows permit secure attachment of impact bars guided by the surgeon's hand. The implant can thus be precisely positioned. The implant preferably has a removable guide shank for engagement of an impact shank or shank for the implant, which also very greatly facilitates the positioning.

According to a further development, an adjustable stop serves for limiting the depth of penetration of an implant into an intervertebral space.

The invention also comprises a novel implant for use as an intervertebral disc prosthesis in an intervertebral space and/or for the preparation of an intervertebral space for use of the implant, having a superior and inferior bearing surface and having at least one anchorage keel each on each bearing surface, the anchorage keel being held removably or lockably on the implant. Such an implant would make it possible to avoid the use of a trial implant and would thus accelerate the operation process. The anchorage keel should be lockable in the guide slot.

This guide slot may serve for guiding a chisel and is preferably in the form of a trapezoidal guide. In addition to the guide slot, a tapped hole for a stop screw for stopping a trapezoidal foot of the keel is provided.

In a further embodiment according to the invention, the anchorage keel itself is in the form of a chisel, it being possible for the chisel to have passages.

The implant according to the invention is formed for insertion between two vertebrae at about 45° to the medial plane.

In a further embodiment according to the invention, the anchorage keel is fixed to a rotation plate which is rotatably and lockably mounted in the bearing surface, the implant having, parallel to the bearing surface, a slot through which a clamping screw can pass, which clamping screw can be screwed tight in a tapped hole in the rotation plate.

The novel trial implant with a chisel guided therein serves for the preparation of the grooves, the chisel being guided in the superior bearing surface so that, when it is subjected to an impact, a groove in the superior vertebra and in the inferior bearing surface is guided so that a groove forms in the inferior vertebra, the two grooves forming at in each case a right angle to the respective intervertebral surface.

The implant according to the invention and/or the trial implant are preferably designed in such a way that the impact shank on its proximal end has a coupling piece for force-transmitting coupling to the shank, which coupling piece has two locks which act separately from one another and have a frictional or interlocking connection and at least one of which is capable of remote release and the two couplings can each transmit at least either a torque or an axial force.

According to the invention, the impact shank of the implant or of the trial implant has, at its distal end, an impact head which has impact surfaces on both sides, i.e. in the distal direction as well as in the proximal direction. The impact shank is preferably provided between its proximal and distal ends with a detachable and displaceable support rod which can be fixed to the impact shank by means of a lockable clamping device.

According to a further development, the implant and/or trial implant according to the invention has a detachable and adjustable stop, the adjustable stop having a captive stopper body on an adjusting screw, and the adjusting screw having a larger external diameter at its proximal end than that bore in the stopper body which it passes through, and the adjusting screw having, at its distal end, an actuator which likewise has a larger external diameter than the bore. This adjustable stop is preferably arranged directly adjacent to the shank in order to stop excess impact force from the impact shank directly at the shank.

According to a further development, the adjustable stop is arranged directly adjacent to the shank and has a bore by means of which it can be guided at least approximately without play on the shank.

On its proximal stop side, the adjustable stop may have a groove-like recess, and this recess is supported with its lateral surfaces in the impacted state at least approximately without play on the bearing surfaces so that it is guided in the normal direction to the bearing surfaces by the implant or trial implant.

A further invention, in particular for use with an implant or a trial implant for the preparation of an intervertebral space for use of an intervertebral disc prosthesis, is a chisel, having a chisel blade and a chisel shank, having an impact head at its distal end, the chisel shank being connected to a displaceable guide which can be inserted in particular into at least one of the guide slots. This chisel has a guide according to the invention, the guide being spring-loaded relative to the chisel shank so that, in the unloaded state, it is pushed towards and beyond the proximal end of the chisel blade. In a particular development, the guide is connected to a piston which is displaceable in the interior of the chisel shank under spring load and has a stop for mounting on a lateral surface.

According to the invention, the implants or trial implants, including the chisel, are in the form of set.

The invention also comprises a novel pre-trial implant for the preparation of an intervertebral space for insertion of an intervertebral disc prosthesis, having a superior and inferior bearing surface, in particular for radiographic and geographic orientation in the intervertebral space, the pre-trial implant being produced substantially from an X-ray-transparent, approximately rectangular or trapezoidal frame which contains a compound slide which is formed from two X-ray-visible spindles and carries a carriage body which is firmly connected to a positioning bar which is oriented at an angle to the two spindles which corresponds to the approach angle (e), the positioning bar projecting through the frame.

According to a particular development, the carriage body carries X-ray-visible markers.

The invention also comprises a novel device for keeping an intervertebral space open for a discectomy and/or for the insertion of an implant or trial implant or pre-trial implant according to one of the preceding specifications, said device being formed from two struts which are independent of one another and can be selected from a group of leaf-like, different struts, the two struts having a wedge shape at the angle of lordosis in their proximal region and optionally being medially curved at their proximal end.

According to the invention, the struts are toothed in their proximal region at their edges facing the vertebrae, and have a coupling device at their distal end for direct or indirect connection to an attachment frame (e.g. Synframe®, trademark of Synthes).

In order to facilitate the access to the vertebrae, at least one of the two struts is angled in the medial direction in its distal region. At least one of the two struts can be reduced in height between its proximal and its distal region.

According to the invention, the two struts can be connected by means of connecting pieces at their distal end, and the connecting piece can be connected to a handle, preferably by means of a detachable coupling, the handle having guide elements for laterally supporting the struts.

The invention also comprises a novel assembly tool for assembling an intervertebral disc implant having a superior and an inferior implant plate and an inlay—in particular according to one of the preceding specifications—with a baseplate and a base as well as a collet in the base, the collet being formed for interlocking with an implant plate, and a batten-like guided sliding element which has an interlocking receptacle for the inlay is coordinated with the base, the two implant plates and inlay being capable of being placed in their receptacles so that they are correctly positioned relative to one another and lock with one another after insertion of the sliding element with inserted implant plate and inserted inlay.

According to a preferred development, the base and the sliding element are slideably connected to one another by means of a parallel guide.

The invention also comprises a novel inserter for inserting a trial implant or an implant according to one of the preceding specifications, having a hand grip of a bar and a retaining mechanism, the retaining mechanism having a locking part and an implant collet, and the implant collet having a locking lever which, in the inserted state, can hold an implant in the implant collet or release it in a controlled manner, and the actuation of the locking part and of the locking lever being effected by a rod or by an actuating part guided in a rod.

According to a particular further development of the inserter, a rod carrying a hand grip at its distal end, an actuating handle which is connected to the actuating part in the rod is provided in the region of the hand grip.

A locking lever of this inserter is preferably medially curved at its free proximal end in order thus—in the locked state—to secure a trial implant or an implant also to prevent loss in the proximal direction.

In order to permit size adaptations for individual use of implants and in order to be able better to design it as set, the implant collet is, according to the invention, designed in a plurality of parts and comprises a collet which can be selected from a group which can be fixed by means of the locking part to a rod, the respective collet being formed diametrically oppositely to the distal part of the respective trial implant or respective implant. The fixing of the respective collet to the locking part is effected by means of at least one guide pin which is longitudinally displaceable together with the locking part on the rod.

In a further embodiment, the inserter comprises a device for holding and inserting a superior implant plate and an inferior implant plate of an intervertebral implant, said inserter comprising a device by means of which the inlay can be introduced by left oblique anterior insertion at about 45° after insertion of the two implant plates with spreading thereof.

The invention also includes an intervertebral implant in the form of an intervertebral disc prosthesis having a superior implant plate, an inferior implant plate and an inlay having at least one anchorage keel (for anchorage each in a superior and in an inferior adjacent vertebra) of a spine, the anchorage keel, in the installed state, lying in a plane which extends at about 45° to the medial plane of the spine.

According to a particular development, this anchorage keel has cockscomb-like teeth at its free end facing the respective vertebra, the toothed system having an inclination which facilitates insertion but prevents removal, by virtue of the fact that the flanks of the teeth in the distal direction have a shallower inclination than the flanks of the teeth in the proximal direction.

This intervertebral implant or implant is coated with a titanium foam or granular titanium over the predominant part of its surface so that it can better integrate with the bones.

The devices, equipment and instruments are used in a method according to the invention for the insertion of an intervertebral implant into an intervertebral space between a superior and an inferior vertebra, the intervertebral implant comprising a superior implant plate, an inferior implant plate and an inlay, and the intervertebral implant being inserted at about 45° with a left oblique anterior approach into at least one prepared groove each in the superior and inferior vertebra.

According to the invention, in a variant, the intervertebral implant can be inserted all in one, or first the two implant plates can be inserted at about 45° and then the inlay can be inserted using an instrument according to the invention at about 45°.

Preferably, each prepared groove for one keel each of the implant plates in the superior and inferior vertebra makes an angle of 90° with the respective intervertebral surface.

An X-ray observation using the sighting slots and/or the guide slot is preferably made during the insertion and positioning of the implant or trial implant.

In the method for the preparation of an intervertebral space through removal of the intervertebral disc and subsequent chiselling of at least one groove each into the superior and inferior vertebrae, a trial implant is pushed into the intervertebral space and is held by the vertebrae under the tension of the muscles.

A trapezoidal guide of a chisel is then inserted into a trapezoidal guide slot, this guide slot and the guide holding the chisel at about 90° to the respective intervertebral surface and at an invariable normal distance. The chisel which is longitudinally displaceable relative to the guide is then tapped stepwise into the respective vertebra up to a stop. Both the insertion of the trial implant and the chiselling are effected at about 45° relative to the medial plane.

The method using the devices and instruments according to the invention for positioning and fixing an intervertebral implant in the intervertebral space therefore preferably comprises the following steps:

- in a first step, a trial implant adapted to the intervertebral space is positioned in the cleaned intervertebral space (with or without struts) at a surgical approach angle e of about 45°,
- in a second step, one groove each is tapped into the superior and inferior vertebrae, normal to the respective intervertebral surface, using a chisel guided in the trial implant, and
- in a third step, struts are used laterally with respect to the trial implant,
- in a fourth step, the trial implant is removed
- and in a fifth step, the implant is inserted either all in one completely with both implant plates and the inlay using an inserter according to the invention, or, using another inserter, first upper and lower part of the implant and then the inlay are inserted.

The positioning of the trial implant in the intervertebral space is effected with the aid of a shank mounted on the trial implant, under radiographic monitoring, using sighting slots in the trial implant and optionally by impacts on impact hollows at the periphery.

By turning the adjusting screw of the adjustable stop using a screwdriver, a trial implant inserted a track too far can also be pulled back.

The trunk of the trial implant is, if required, fixed by means of the impact shank on a frame (Synframe®, trademark of Synthes) or held by a person.

In an alternative method according to the invention, for increasing the accuracy of fit, the chisel guided in the trial implant is left in the superior or inferior groove after the chiselling, and the opposite groove is then chiselled using a further chisel.

LIST OF REFERENCE NUMERALS/PARTS OF THE INVENTION

1 Superior vertebra
2 Inferior vertebra
3 Groove in superior vertebra
4 Groove in inferior vertebra
5 Upper/superior implant plate
6 Inlay, preferably of polyethylene
7 Lower/inferior implant plate
 The plates 5 and 7 are named as superior and inferior, but they can also be formed or installed vice versa. Thus, the inlay can also be fixed, for example, on the superior plate.
8 Impact shank for trial implant, mounted on the guide shank 22 if required.
9 Trial implant
10 Chisel
11 Upper/superior guide slot for chisel 10 or guide slot for keel 54a'
12 Lower/inferior guide slot for chisel 10 or guide slot for keel 54b'
13 Inserter for insertion of 45° implant (all in one)
14 45° implant (all in one)
15 45° implant, divided embodiment
16 Inserter for insertion at 45°, first insertion of upper and lower part and subsequently insertion of inlay
17 Adjustable stop
18 Assembly tool, preferred for assembly since the implant can be assembled before despatch and packing or at the operating table itself before surgery. This makes it easier for the operating theatre staff to produce, according to the invention, the correct combination in each case from a selection of plates and inlays.
19 Collet (receptacle for implant)
20 Strut left
21 Strut right
22 Trial implant shank is a handle and guide for impact shank 8
23 a, b Parallel guidance of 18, e.g. by means of guide pins, the implant is inserted over head to ensure that the bone ingrowth layer on the surface of the implant plate is not damaged during insertion of the inlay, which might weaken the connection to the bone.
24 a, b Impact hollows, at least one on the trial implant
25 Thread for adjustable stop
26 a,b Lateral sighting slots
27a,b Anterior-posterior (AP) sighting slots
28 Chisel shank
29 Impact head
30 Chisel blade
31 Fit-in guidance for the guide slots 11 and 12
32 Piston
33 Spring
34 Rinse slot
35 Bearing pin
36 Bearing pin axle
37 Distance piece
38 Locking lever
39 Joint pin
40 Actuating bar
41 Actuating handle
42 Rod
43 Locking part
44 a,b Guide pin
45 Hand grip
46 Insert pin for superior plate
47 a,b Insert pin for inferior plate
48 Spring
49 Support rod for attachment on Synframe or on another support device
50 Clamping device
51 Impact bar
52 Mallet with notch which fits into the shank of the chisel
53 Screwdriver
54a Upper anchorage keel of the implant
54b Lower anchorage keel of the implant
55 Double arrow
56 Slot
57 Clamping screw
58 Tapped hole
59 Rotation plate
60a,b Upper and lower keel socket
61 Tapped hole
62 Intervertebral space 63 Superior bearing surface of the trial implant
64 Inferior bearing surface of the trial implant
65 Lateral surface
66 Stop screw
67 Coupling piece between shank 22 and impact shank 8
68 Impact head
69 Stopper body
70 Adjusting screw
71 Actuator
72 Bore
73 Superior bearing surface of the implant
74 Inferior bearing surface of the implant
75 Stopper
76 Frame
77 a,b X-ray-visible spindles
78 Carriage body
79 Pre-trial implant
80 Positioning bar
81 Proximal area
82 Edges of struts
83 Coupling device of struts
84 Attachment frame
85 Distal area of the struts
86 Distal end of the struts
87 Connecting piece
88 Handle connected to the connecting piece
89 Coupling
90 Guide element for lateral support
91 Baseplate
92 Base
93a Collet for implant plate
93b Collet for the inlay
94 Sliding element
95 Proximal end of the locking lever 38
96a,b X-ray-visible markers of the carriage body 78
97 Actuating element
98 Proximal end
99 Connecting handle to the struts
100 Strut left
101 Strut right
102 Handle
103 Lock
104 Impact plate
105 Recesses for screwdrivers
106 Impact pipe
107a,b Guide rail for struts
108 Support rod
109 Lock
110 Module device
111a,b Cockscomb-like end of the keels which faces the vertebra
112a,b Teeth of the keels
113 Proximal end
x . . . Distance from the end region of the grooves to the spinal canal
a . . . Angle of lordosis=angle of the bearing surface of the trial implant=angle of the implant 14, 15
β . . . Angle between the anchorage keels
? . . . Angle between sighting slot and guide slot or between the AP line and the anchorage keels 54a,b
d . . . . Complementary angle to ? between sighting slot and guide slot
e . . . Surgical approach angle, the angle between AP and the approach of the surgeon to the vertebra

DESCRIPTION OF THE DRAWINGS

FIG. 18: An oblique view of the implant 5', 6, 7' having superior plate 5', inferior plate 7' and an inlay 6, with a superior bearing surface 73, an inferior bearing surface 74, a superior rotatable anchorage keel 54a; the double arrow 55 indicates the direction of rotation. The anchorage keel 54a is fixed to a rotation plate 59. Through a slot 56, the rotation plate can be fixed to the superior plate 5' by means of a clamping screw 57 through a tapped hole 58;

FIG. 22: A trial implant 9 having shaft 22, superior and inferior guide slot 11, 12, with sighting slots 27a,b, with impact hollows 24a,b, with thread 25 for the adjustable stop 17, with sighting slots 26a,b. The sighting slots may also be filled with a X-ray-transparent material;

FIG. 21) with impact hollows 24a,b, with thread 25 for the adjustable stop, with sighting slots 26a,b.

FIG. 26: A trial implant 9 having shaft 22, superior and inferior bearing surface 63, 64, superior and inferior guide slot 11, 12, with sighting slots 27a,b (underside) with impact hollows 24a,b, with thread for the adjustable stop 17, with sighting slots 26a,b (underside), with adjustable stop 17, having a mobility of about 9 mm.

FIG. 34) is coordinated with each implant plate 5, 7 with inlay 6 (cf. FIG. 10);

FIG. 41: Inserter 13 with locking part 43 and with collet 19a, with bearing pin 35, distance piece 37, and inserted implant 5, 6, 7;

FIG. 45: Clamping device 50 with handle 8 and support rod 49;

FIG. 46: Trial implant 9 inserted into the intervertebral space 62 between the superior vertebra 1 and the inferior vertebra 2 with an adjustable stop 17 and a shank 22. The trial implant can be brought into the correct position with the impact bar 51 by tapping into the impact hollows 24a,b. The adjustable stop 17 prevents the trial implant 9 from being pushed too deeply into the intervertebral space 62;

FIG. 46);

FIG. 92b: Side view of the holding and impact device 110 (for the struts 100, 101), with handle 102, lock 103, locking peg 109, support rod 108, impact head 104, impact pipe 106 and guide 107a;

The figures are described overall. Identical reference numerals denote identical components. Identical reference numerals having different indices denote functionally similar components.

Figure 1:
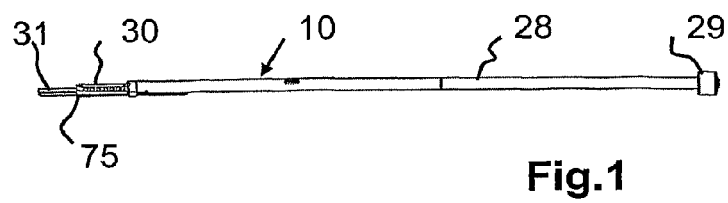
FIG. 1: A chisel 10 having a chisel blade 30 (monochisel), a diametrically opposite guide part 31 and a shank 28 with an impact head 29 and a stopper 75.

BEST MODE OF EMBODIMENTS OF PREFERRED PROCEDURES OR METHODS FOR USING THE INVENTION

A trial implant 9 (FIG. 20-23) having a superior and inferior bearing surface 63, 64 and having one guide slot 11, 12 each in the superior and inferior bearing surface 63, 64 serves for the preparation of an intervertebral space 62 for insertion of an intervertebral disc prosthesis according to the invention. At least one of the guide slots 11, 12 is formed in such a way that an insertable or inserted guide 31 can be held or is held nondisplaceably in two directions in space—in particular parallel and normal to the respective bearing surface.

The guide slots 11, 12 serve for guiding a chisel 10 (FIG. 1) in the trial implant 9. According to the invention, the chisel is in the form of a monochisel 10 which is connected to a guide 31 which is displaceable relative to it and is formed diametrically opposite to the respective guide slot 11, 12. The two guide slots 11, 12 are at an angle β relative to one another in different positions in space.

At least one of the slots 26a, 26b, 27a, 27b in the trial implant 9 (FIG. 20-23) serves as a sighting slot. It is formed in such a way that, when a trial implant 9 is inserted into an intervertebral space 62, it enables the position thereof to be detected relative to the vertebrae 1, 2 by means of X-rays.

Figure 62:
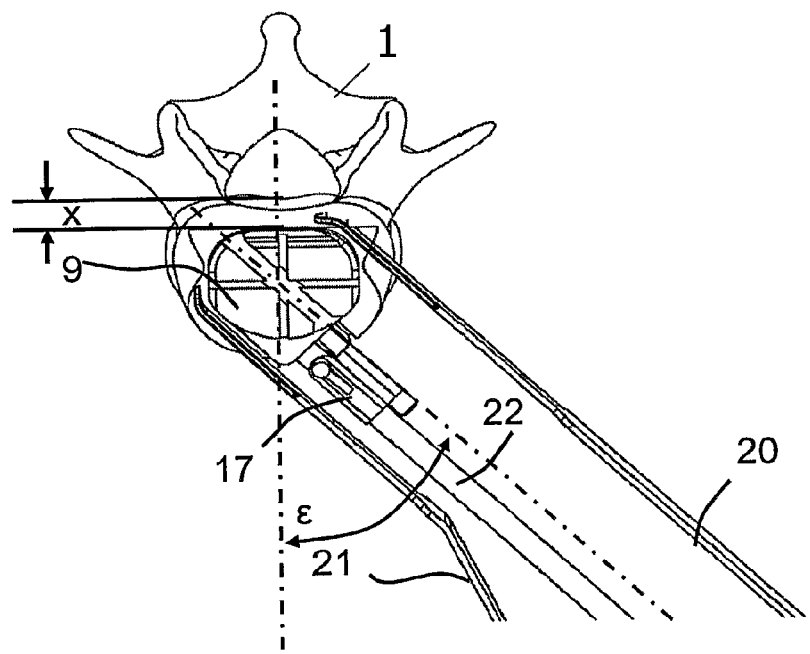
FIG. 62: Plan view of an inferior vertebra 2, with inserted trial implant 9 with adjustable stop 17 and shank 22, and with inserted left 20 and right 21 struts. The trial implant 9 is at distance x from the end region of the grooves to the spinal canal. The struts 20 and 21 are inserted at the surgical approach angle e to the left and right of trial implant 9. The right strut 21 is angled at about 20° in the middle part in order to permit a better view.
Figure 63A:
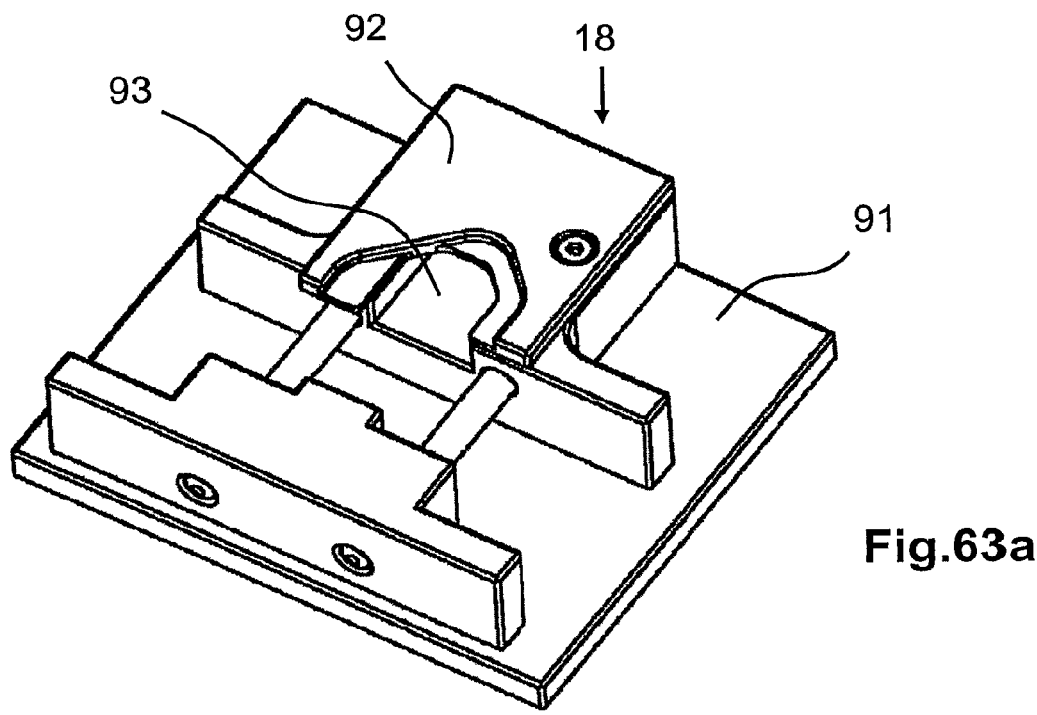
FIG. 63a-e: Implant assembly tool 18 for assembling the implant with the inlay 6 (FIG. 63c,d) and the inferior plate 7 (FIG. 63c-e); with baseplate 91, base 92 and collet for the implant plate with the inlay 93 (FIG. 63a,b).
Figure 63B:
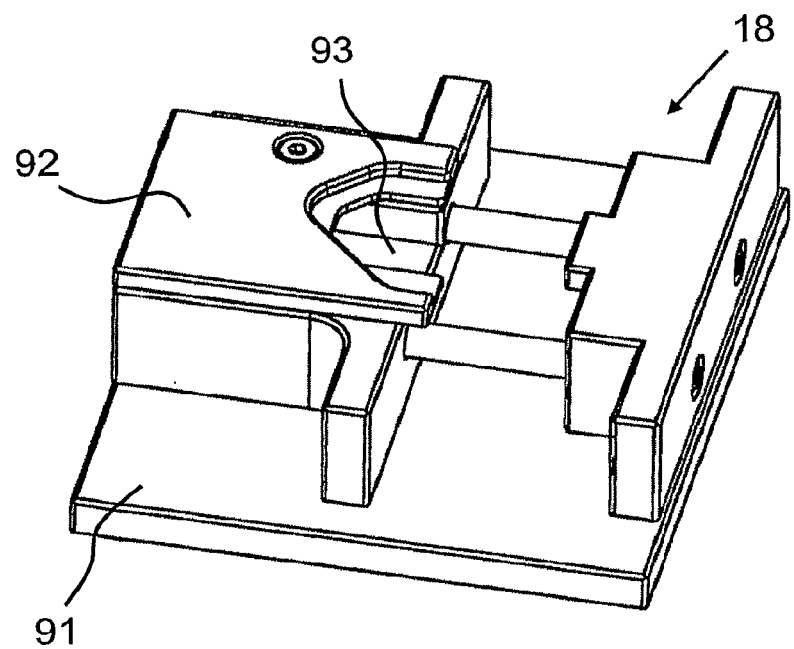
Figure 63C:
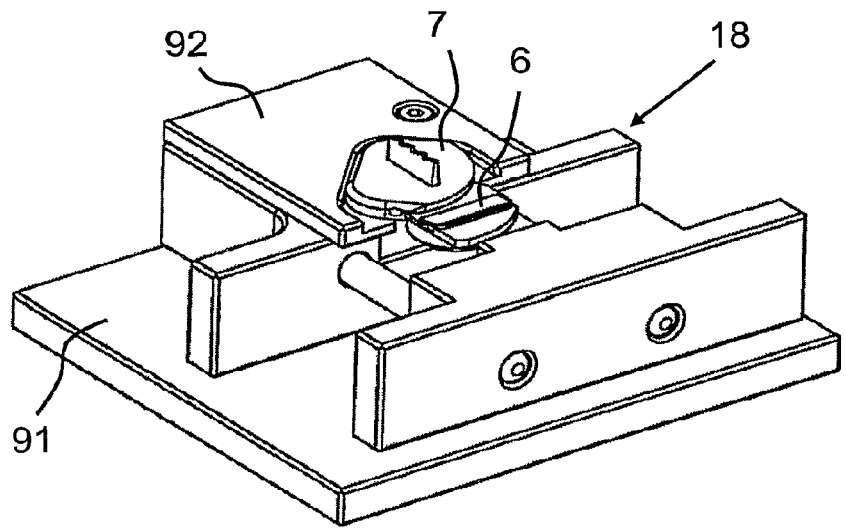
Figure 63D:
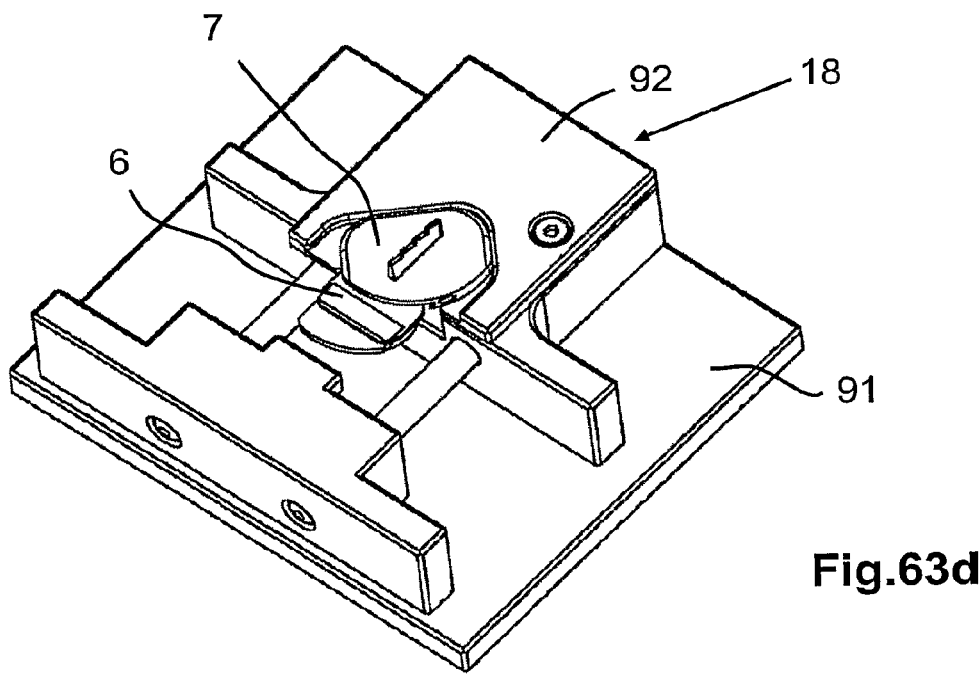
Figure 63E:
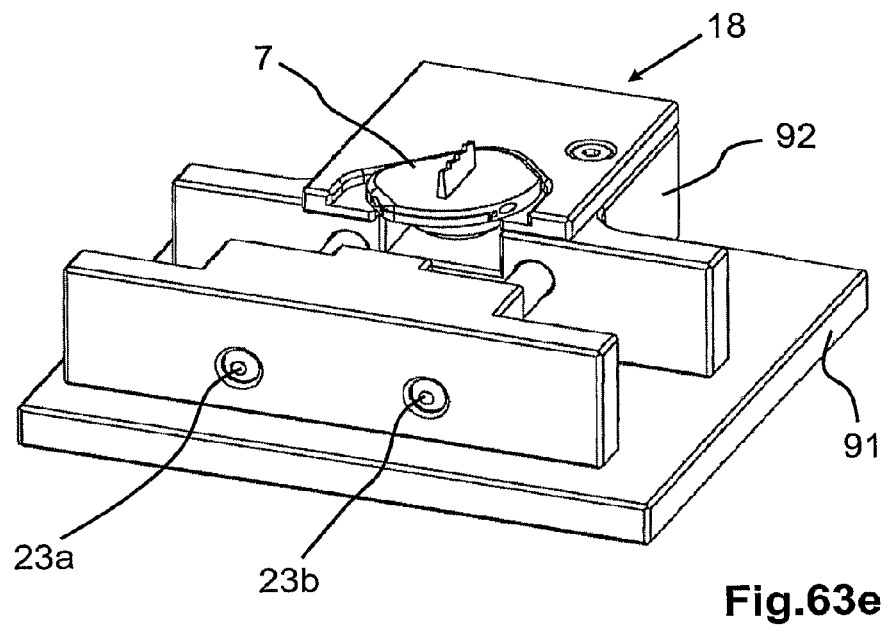

The sighting slots of the trial implant 9 (FIG. 20-23), 26a, 26b, 27a, 27b, are at an angle ? or at a complementary angle d to the respective guide slot 11, 12. The surgical approach angle e (FIG. 62, 76) corresponds to the direction of insertion of the implant into the intervertebral space 62 for the implantation of the intervertebral disc prosthesis.

The two sighting slots 26a, 26b, 27a, 27b per bearing surface 63, 64 in the trial implant 9 (FIG. 20-23) are preferably at a right angle to one another.

The trial implant 9 consists of X-ray-opaque or X-ray-visible material.

The sighting slots 26a, 26b, 27a, 27b in the trial implant 9 (FIGS. 20-23) can be filled with X-ray-transparent material, e.g. plastic, or the trial implant 9 may be plastic-coated, e.g. of polyethylene.

Instead of the sighting slots 26a, 26b, 27a, 27b in the trial implant 9 of X-ray-transparent material, X-ray-visible inlays may also be provided or the guide slots 11, 12 may be X-ray-visible.

Figure 47:
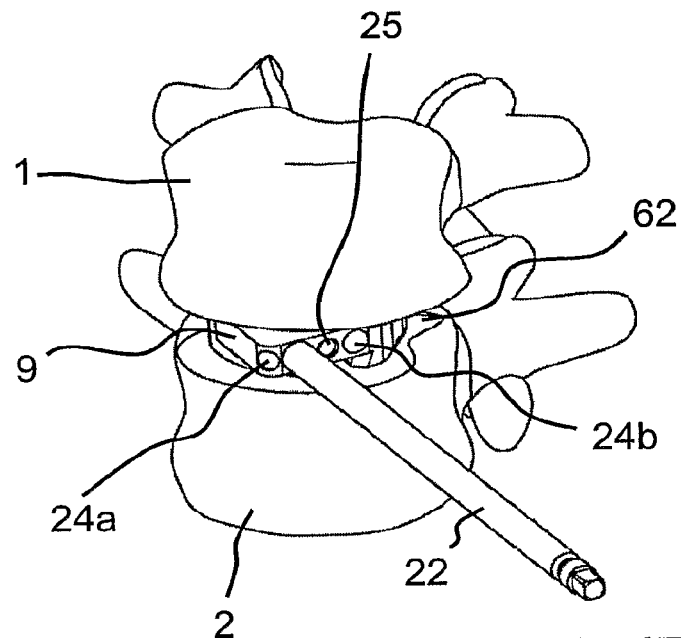
FIG. 47: Trial implant 9 inserted into the intervertebral space 62 between the superior vertebra 1 and the inferior vertebra 2 with a shank 22, and with impact hollows 24a, b and the thread 25 for the adjustable stop 17 (cf.
Figure 48:
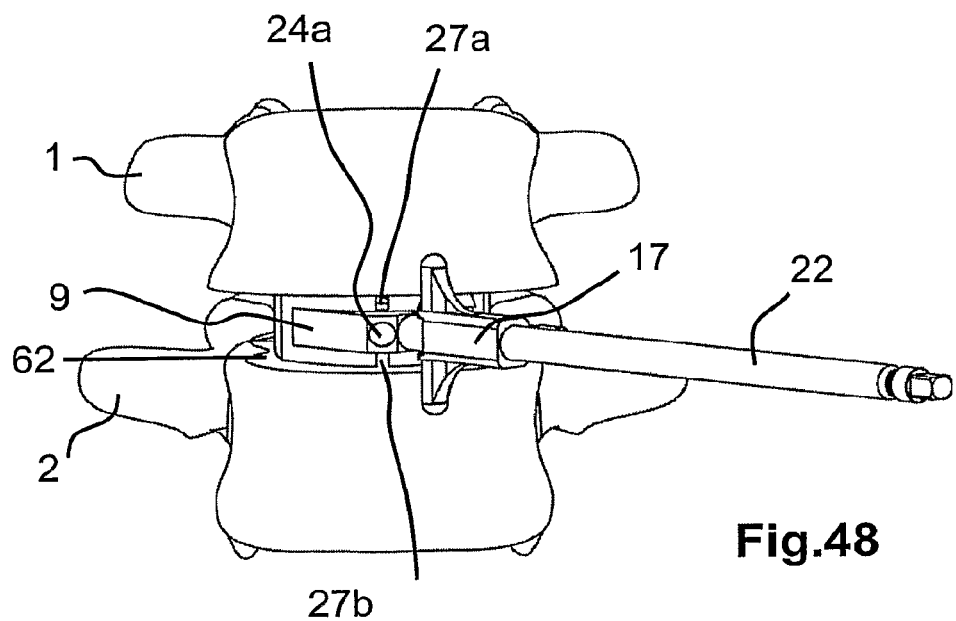
FIG. 48: Trial implant 9 inserted into the intervertebral space 62 between the superior vertebra 1 and the inferior vertebra 2 with a shank 22, and with impact hollows 24a and adjustable stop 17 and with the sighting slots 27a,b, viewed from the anterior-posterior direction.
Figure 49:
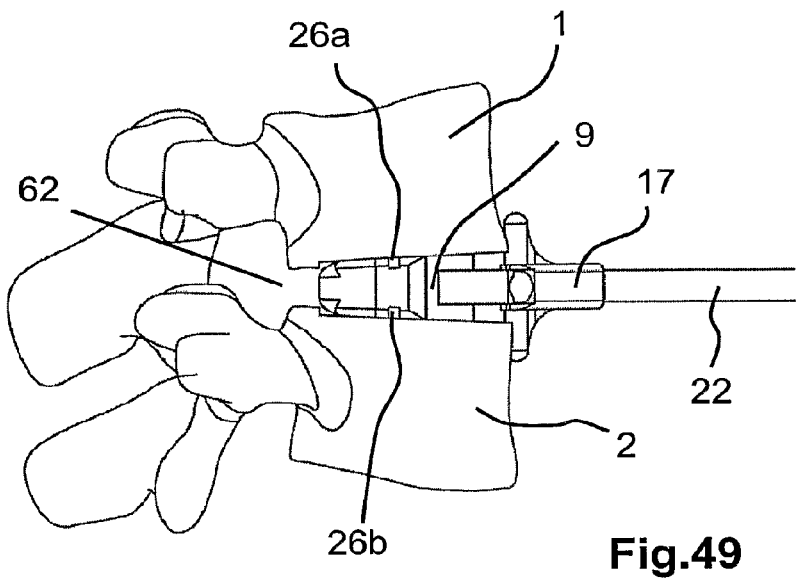
FIG. 49: Trial implant 9 inserted into the intervertebral space 62 between the superior vertebra 1 and the inferior vertebra 2 with a shank 22, and with adjustable stop 17 and with the sighting slots 26a,b, viewed from the lateral direction.

In the trial implant 9 for the preparation of an intervertebral space 62 (FIGS. 46, 47) for insertion of an intervertebral disc prosthesis, having a superior and inferior bearing surface 63, 64 and having a lateral surface 65 (FIGS. 22, 23), at least one impact hollow 24a, 24b for the engagement of an impact bar 51 is provided on the lateral surface 65.

Figure 96:
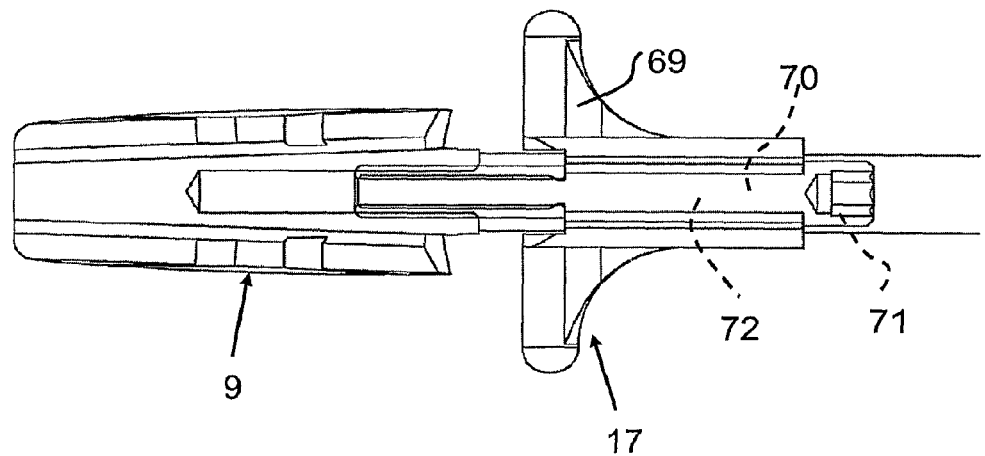
FIG. 96: Cross-section through an adjustable stop 17 inserted into a trial implant 9, with stopper body 69, adjusting screw 70, actuator 71 and bore 72.

The trial implant 9 has a guide shank 22 for engagement of an impact shank or handle 8, and is equipped with an adjustable stop 17 (FIGS. 21, 96) which limits the depth of insertion of the trial implant 9 into the intervertebral space 62.

Figure 17:
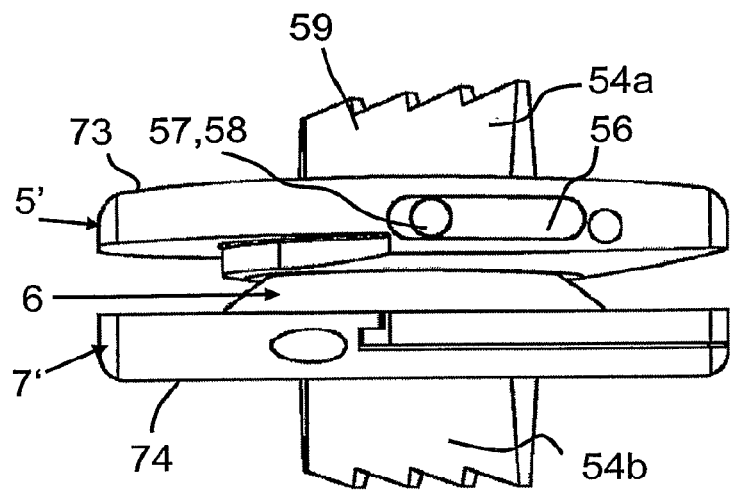
FIG. 17: AP view of an implant variant according to the invention, having superior plate 5', inferior plate 7' and an inlay 6, with a superior bearing surface 73, an inferior bearing surface 74 with anchorage keel 54b, a superior rotatable anchorage keel 54a. The anchorage keel 54a is fixed to a rotation plate 59 (cf.

For use as an intervertebral disc prosthesis in a prepared intervertebral space 62, a further implant 5', 6, 7' according to the invention is provided (FIGS. 17, 18, 19) having a superior and inferior bearing surface 73, 74 and having at least one guide slot 11, 12 each in the superior and inferior bearing surface 63, 64 (FIG. 10-14), at least one of the guide slots 11, 12 being formed in such a way that an insertable or inserted guide 31 can be held or is held nondisplaceably in two directions in space—in particular parallel and normal to the respective bearing surface.

Figure 12:
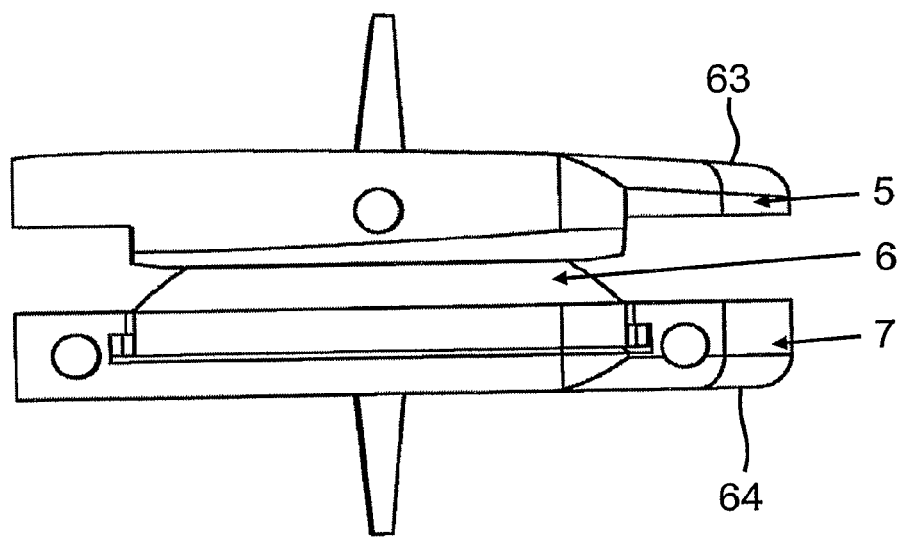
FIG. 12: The implant 5, 6, 7 with superior 63 and inferior 64 bearing surface, 45° view.
Figure 13:
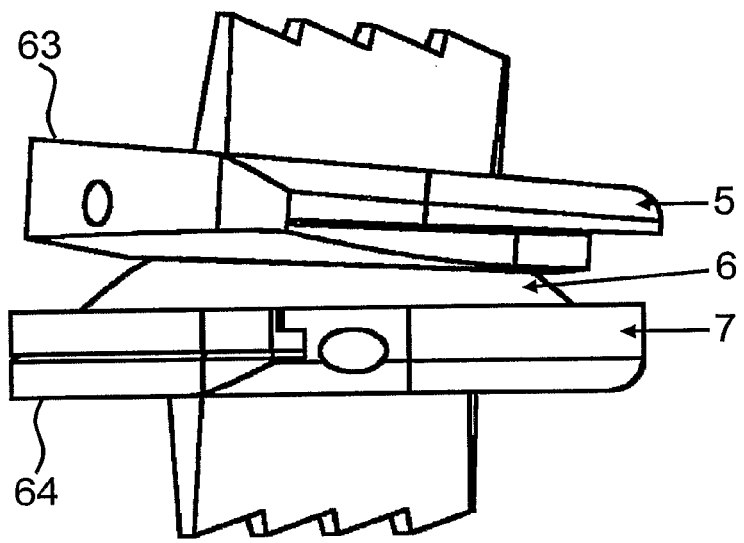
FIG. 13: The implant 5, 6, 7 with superior 63 and inferior 64 bearing surface, side view.
Figure 14:
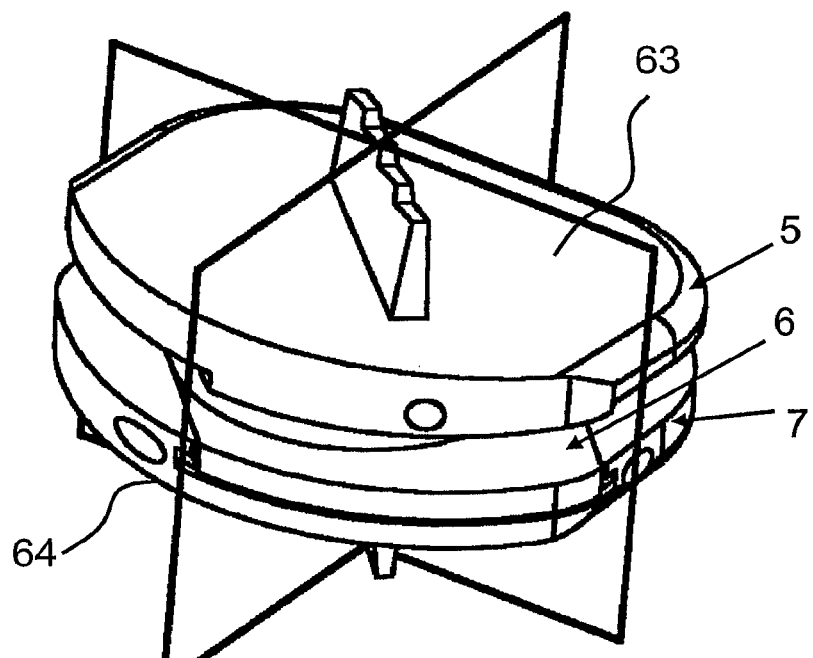
FIG. 14: The implant 5, 6, 7 with superior 63 and inferior 64 bearing surface, oblique view with the AP and lateral planes.
Figure 15:
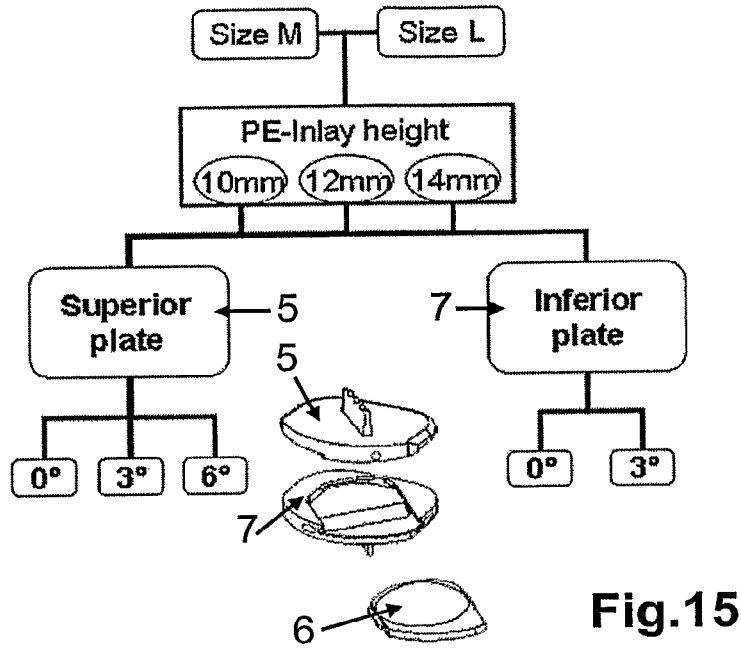
FIG. 15: Overview of different-size implants M (medium) and L (large), with PE inlays 6 in the sizes 10 mm, 12 mm, 14 mm, and superior plates 5 with the angles of lordosis 0°, 3°, 6°, and the inferior plate 7 with 0° and 3° and the inlay 6.
Figure 16:
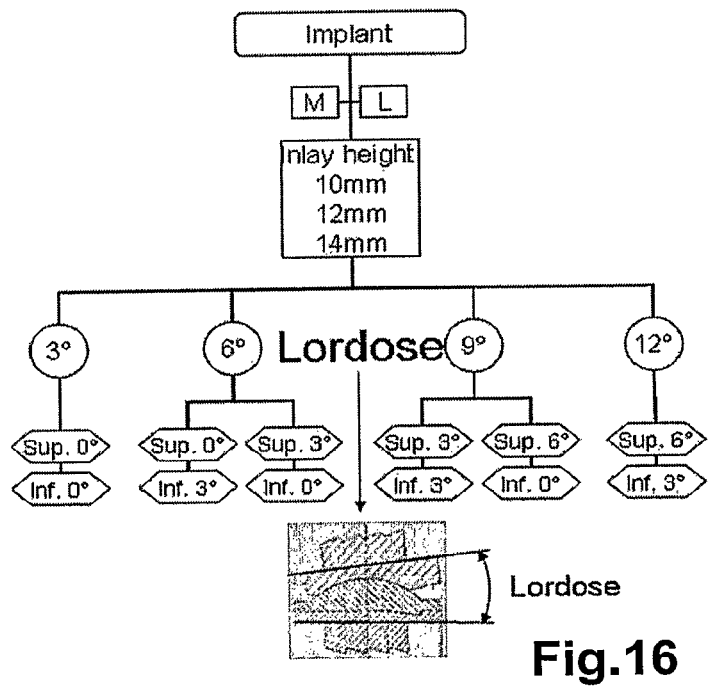
FIG. 16: Overview of the choice of implant: during the operation, the surgeon chooses implants of size M or L according to the bearing surface of the vertebra. The inlays 6 with the sizes 10 mm, 12 mm or 14 mm are mounted between the superior plate 5 and the inferior plate 7. This results, through pairing of a superior plate 5 with an inferior plate 7, in implants having an angle of lordosis of 3°, 6°, 9° or 12°. 12° is an exception and is reserved for the specially trained surgeon for special cases.

In this implant 5', 6, 7', the guide slot 11, 12 (FIG. 19) serves for guiding a chisel 10 (FIG. 1). The chisel is in the form of a monochisel 10 and is connected to a guide 31 which is displaceable relative to it and is formed diametrically opposite to the respective guide slot 11, 12. The two guide slots 11, 12 of the implant 5', 6, 7' are at an angle 1 relative to one another in different positions in space (FIG. 12).

Figure 64:
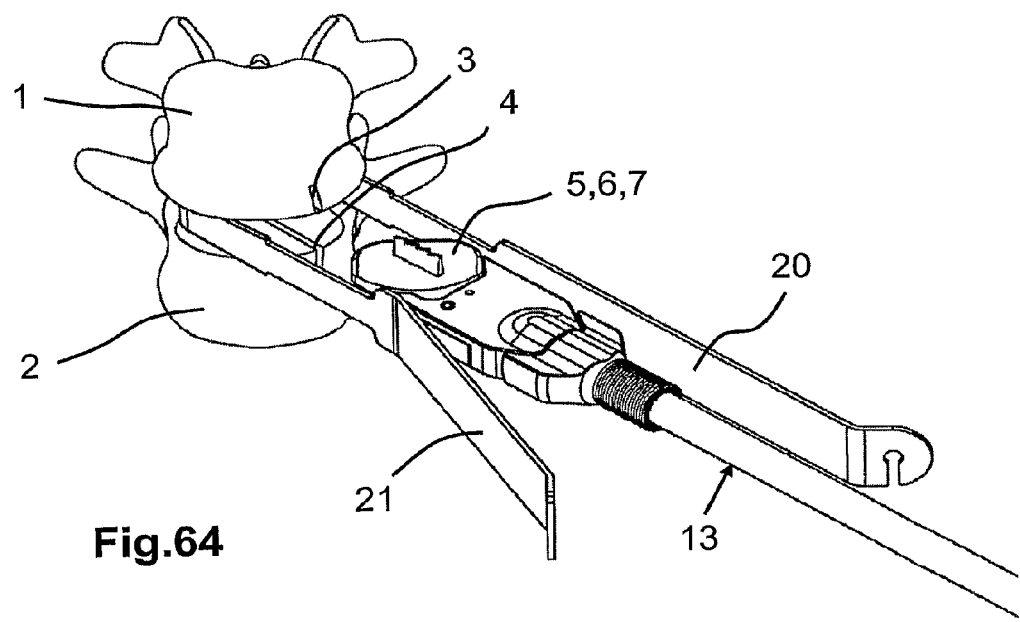
FIG. 64: Upper vertebra 1 and inferior vertebra 2 with the chiselled grooves 3 and 4, with inserted struts 20 and 21, and with the inserter 13 for insertion of the 45° implant 5, 6, 7 all in one (both superior plate 5 and inferior plate 7 with inserted inlay 6 simultaneously)

The implant 5', 6, 7' is intended for use as an intervertebral disc prosthesis in an intervertebral space 62 (FIG. 64) and for the preparation of the intervertebral space 62, having a superior and inferior bearing surface 63, 64 (FIG. 12) and having at least one slot 26a, 26b, 27a, 27b each in the superior and inferior bearing surface 63, 64, at least one of the slots being in the form of a sighting slot so that, when an implant 5', 6, 7' is inserted into an intervertebral space 62 (FIG. 18), it enables the position thereof to be detected relative to the vertebrae 1, 2 by means of X-rays.

In the case of implant 5', 6, 7', the sighting slots 26a, 26b, 27a, 27b are at an angle ? or at a complementary angle d to the respective guide slot 11, 12, which corresponds to the surgical approach angle e or the direction of insertion of the implant 5', 6, 7' into the intervertebral space 62 for the implantation of the intervertebral disc prosthesis. Two sighting slots 26a, 26b, 27a, 27b are provided per bearing surface 62, 63 and are at a right angle to one another.

The implant 5', 6', 7' (FIG. 18) consists partly, in various combinations, of X-ray-opaque or X-ray-visible and of X-ray-transparent or X-ray-invisible material. Except for the inlay 6, all parts may comprise metal or plastic; instead of the sighting slots 26a, 26b, 27a, 27b, for example, it is also possible to provide X-ray-opaque or X-ray-visible inlays, or the guide slots 11, 12 may be X-ray-visible.

At least one impact hollow 24a, 24b for engagement of an impact bar 51 is provided on the lateral surface 65 of the implant 5', 6, 7'.

The implant 5', 6, 7' (FIG. 18) has a removable guide shank 22 for engagement of an impact shank or handle which is equipped with an adjustable and removable stop 17 which limits the insertion of the implant 5', 6, 7' into the intervertebral space 62.

The implant 5', 6, 7' (FIG. 18) for insertion as an intervertebral disc prosthesis into an intervertebral space 62 and/or for the preparation of an intervertebral space 62 for insertion of the implant 5', 6, 7' having a superior and inferior bearing surface 63', 64' and having at least one anchorage keel 54a', 54b' each on each bearing surface 63', 64', has anchorage keels 54a', 54b' which are removably or lockably held on the implant 5', 6, 7'.

Figure 18:
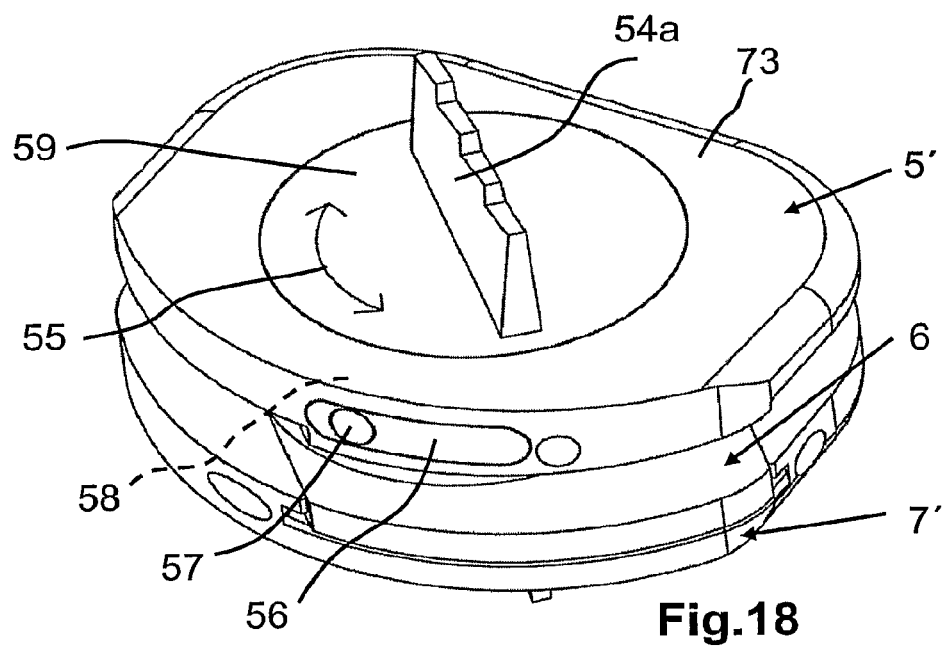
FIG. 18). Through a slot 56, the rotation plate 59 can be fixed to the plate 5' by means of a clamping screw 57 through a tapped hole 58.
Figure 19:
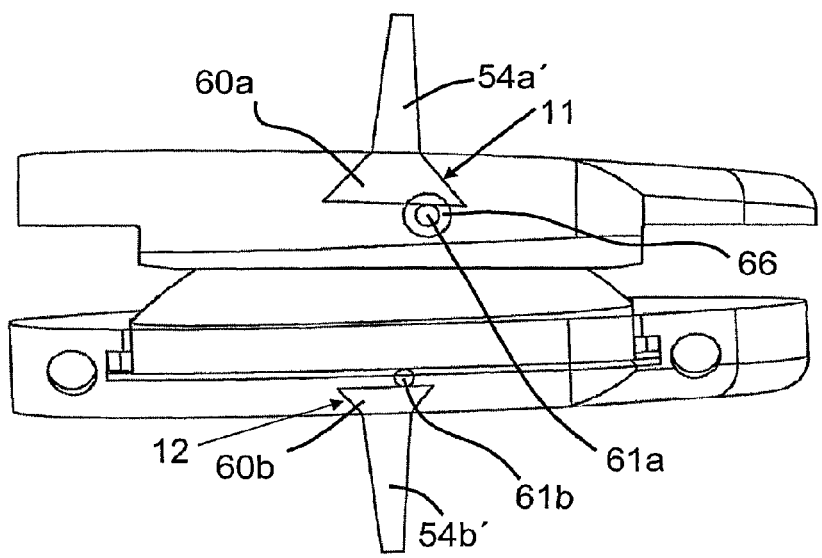
FIG. 19: A further variant having mobile keels 54a' and 54b'. The keels 54a' and 54b' with the keel sockets 60a and 60b rest in a guide slot 11' and are fixed through a tapped hole 61a by means of a stop screw 66. This variant can be presented either only above or above and below or only below.
Figure 20:
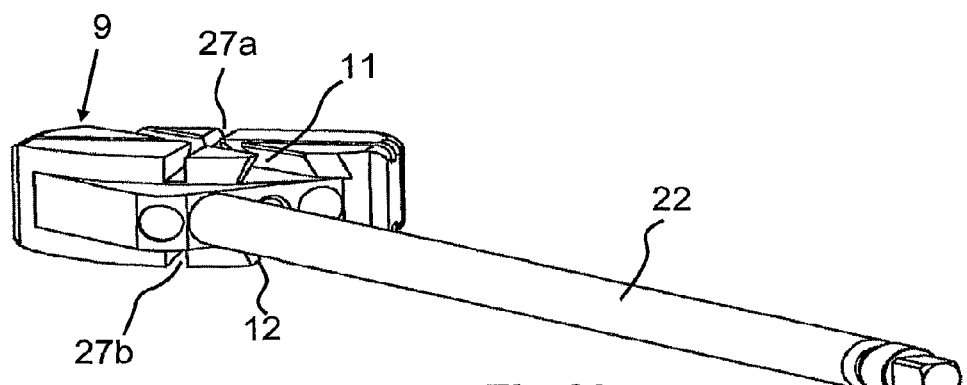
FIG. 20: A trial implant 9 having shaft 22, superior and inferior guide slot 11, 12, with sighting slots 27a,b.
Figure 21:
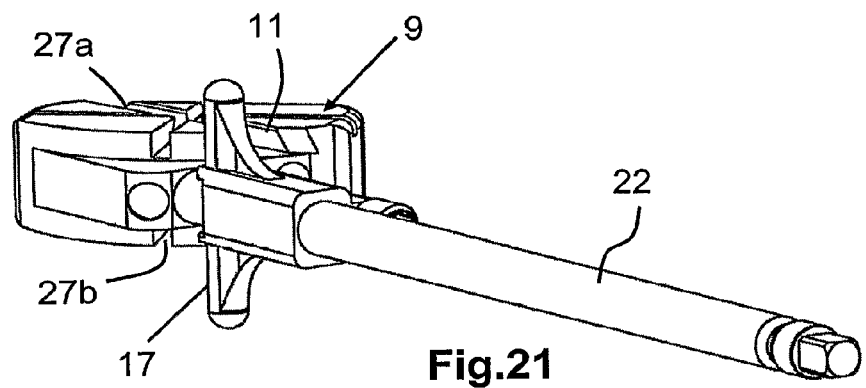
FIG. 21: A trial implant 9 having shaft 22, superior and inferior guide slot 11, 12 (cf.
Figure 22:
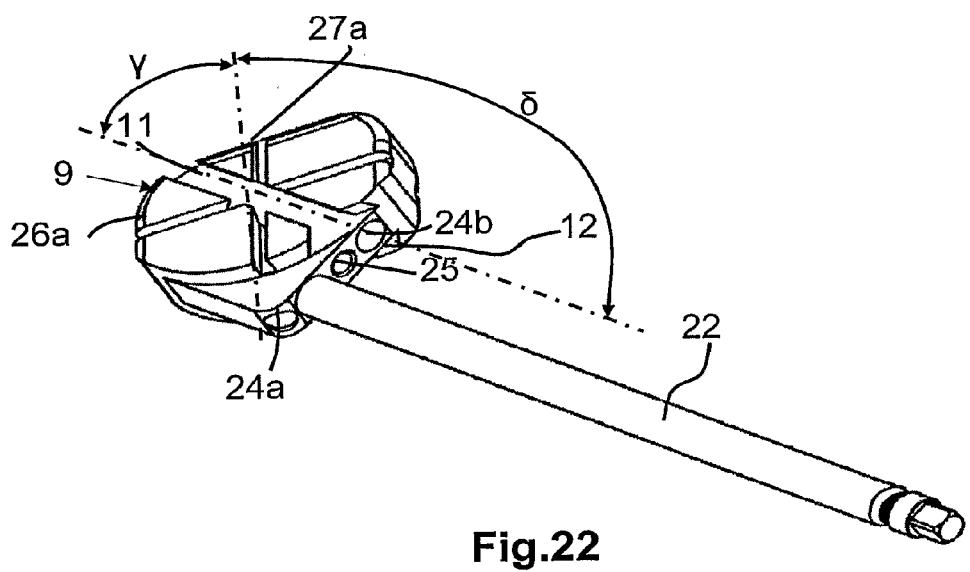
FIG. 22), with sighting slots 27a,b with adjustable stop 17.
Figure 23:
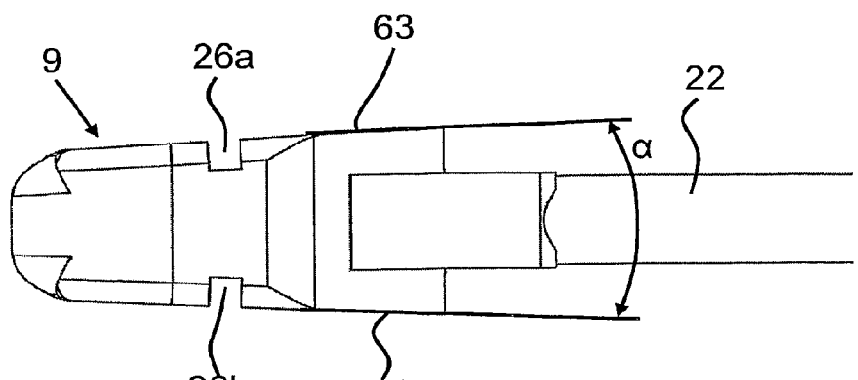
FIG. 23: A trial implant 9 having shaft 22, superior and inferior bearing surface 63, 64 with sighting slots 26a,b.
Figure 24:
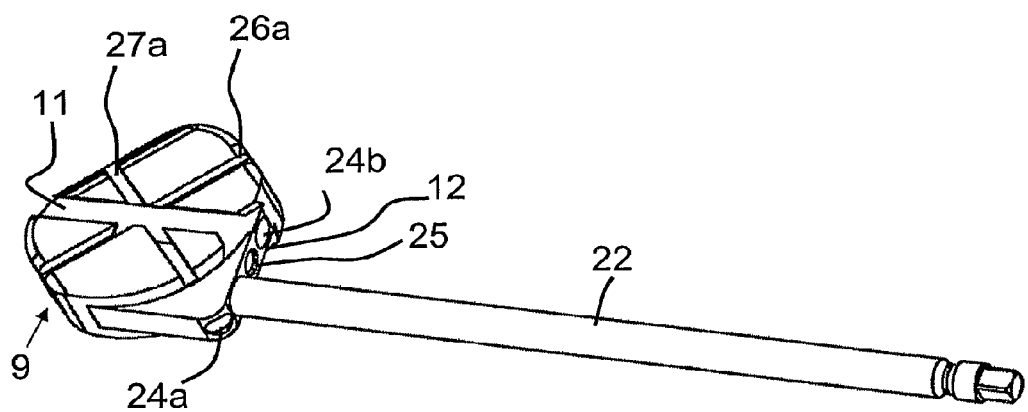
FIG. 24: A trial implant 9 having shaft 22, superior and inferior guide slot 11, 12 (cf.
Figure 25:
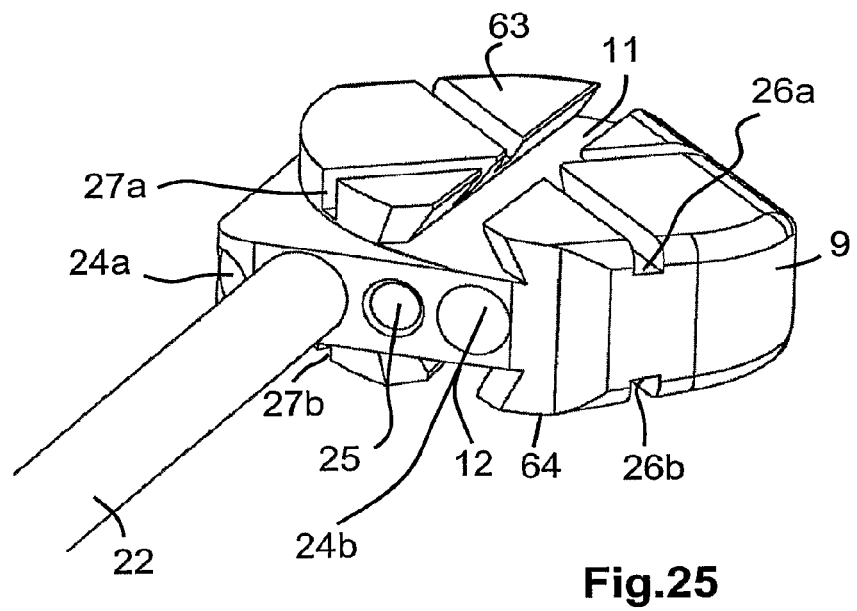
FIG. 25: A trial implant 9 having shaft 22, superior and inferior bearing surface 63, 64, superior and inferior guide slot 11, 12, with sighting slots 27a,b with impact hollows 24a,b, with thread 25 for the adjustable stop, with sighting slots 26a,b.
Figure 26:
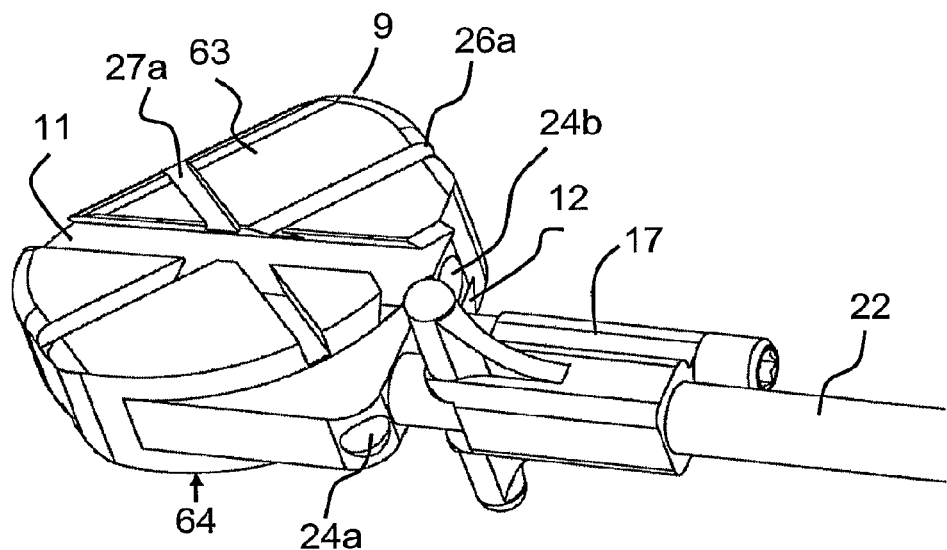
FIG. 26), with sighting slots 27a,b (cf.

The guide slot 11, 12 in the implant 5', 6, 7' (FIG. 18) or trial implant 9 is, according to the invention, in the form of a trapezoidal guide (FIG. 19).

In addition to the guide slot 11, 12 in the implant 5', 6, 7', a tapped hole (FIG. 19) 61a, 61b for a stop screw 66 for stopping a trapezoidal socket 60a, 60b of the keel 54a', 54b' is provided;

The anchorage keel 54a, 54b, 54a', 54b' in the implant 5', 6, 7' (FIG. 19) may also be in the form of a chisel, it being possible for the chisel 10 to have passages.

The anchorage keel 54 of the implant 5', 6, 7' (FIG. 18) may be attached to a rotation plate 59 which is rotatably and lockably mounted in the bearing surface 63'.

A slot 56 through which it is possible to pass a clamping screw 57 which can be tightened in a tapped hole 58 in the rotation plate 59 is provided parallel to the bearing surface 63' of the implant 5', 6, 7' (FIG. 18).

With the trial implant 9 and the chisel 10 guided therein, a groove 3 can be chiselled in the superior vertebra 1 and a groove 4 in the inferior vertebra 2 at right angles to the respective intervertebral surface (FIG. 53-58).

The impact shank 8 of the implant 5, 6, 7 or trial implant 9 has, at its proximal end, a coupling piece 67 for coupling to the shank 22 with force transmission.

Figure 44:
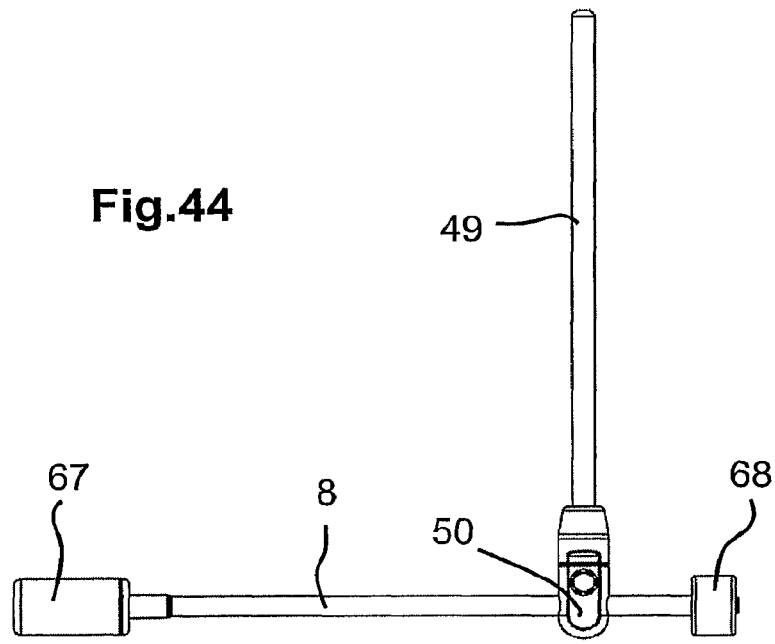
FIG. 44: Handle 8 with impact head 68 and coupling piece 67 for the trial implant with support rod 49 for attachment on Synframe or on another support device, with a clamping device 50.

The impact shank 8 (FIG. 44) of the implant 5, 6, 7 or trial implant 9 may have, at its distal end, an impact head 68 which has impact surfaces on both sides, i.e. in the distal direction as well as in the proximal direction. The impact shank 8 has, between its proximal and distal ends, a detachable and displaceable support rod 49 which can be fixed by means of a lockable clamping device 50 to the impact shank 8.

Figure 50:
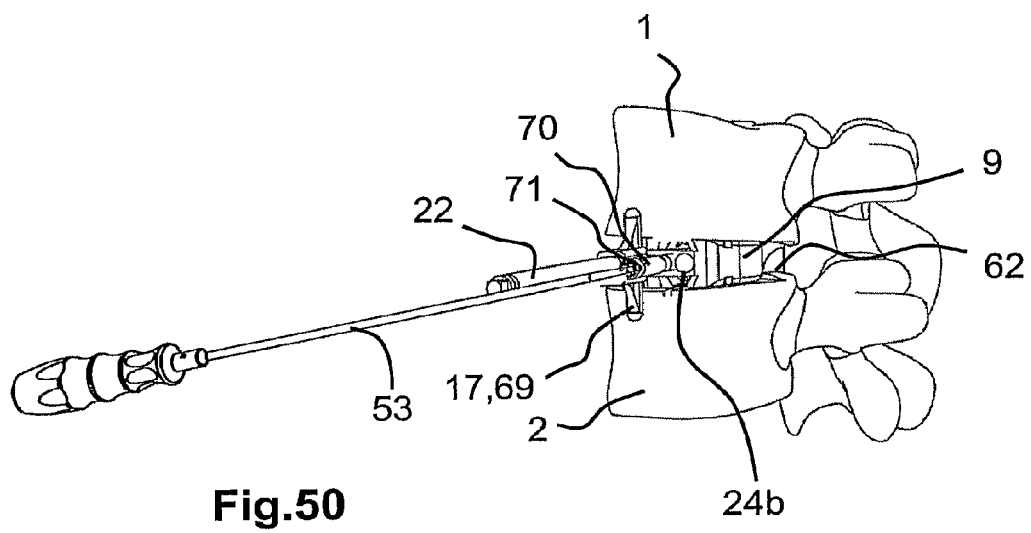
FIG. 50: Trial implant 9 inserted into the intervertebral space 62 between the superior vertebra 1 and the inferior vertebra 2 with a shank 22 and with impact hollows 24a,b and adjustable stop 17 and with the screwdriver 53 for adjusting the depth of penetration of the trial implant with the adjustable stop 17, with stopper body 69, adjusting screw 17 and actuator 71.
Figure 51:
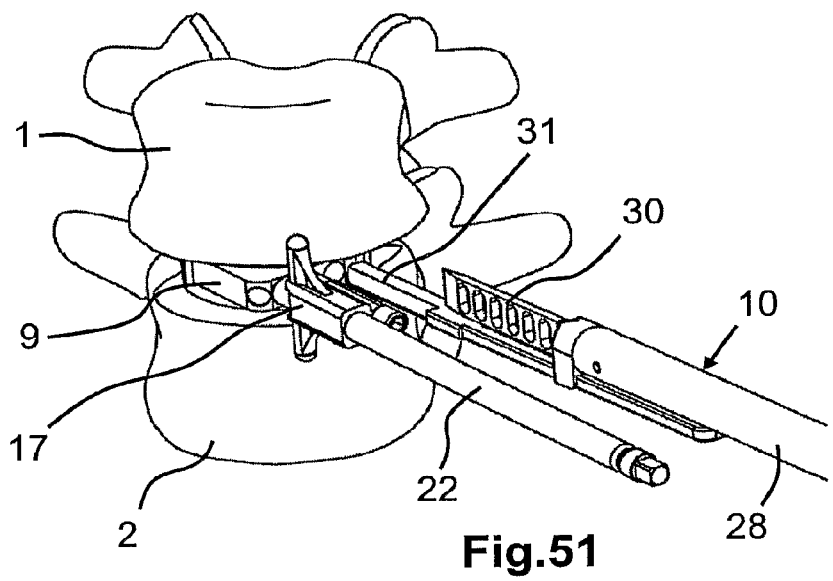
FIG. 51: Trial implant 9 with adjustable stop 17 and shank 22, inserted between a superior vertebra 1 and an inferior vertebra 2, and chisel 10 having fit-in guidance 31 and a chisel blade 30, fixed to a chisel shank 28.

A detachable and adjustable stop 17 (FIG. 96) is provided for limiting the penetration of the implant 5, 6, 7 or trial implant 9, the adjustable stop 17 having a captive stopper body 69 (FIGS. 50, 96) on an adjusting screw 70, and the adjusting screw 70 having a larger external diameter at its proximal end than that bore 72 in the stopper body 69 through which it passes, and the adjusting screw 70 having, at its distal end, an actuator 71 (FIGS. 50, 96) which likewise has a larger external diameter than the bore 72. The adjustable stop 17 is arranged directly adjacent to the shank 22 in order to stop excessive impact force from the impact shank 8 directly at the shank 22.

Figure 52:
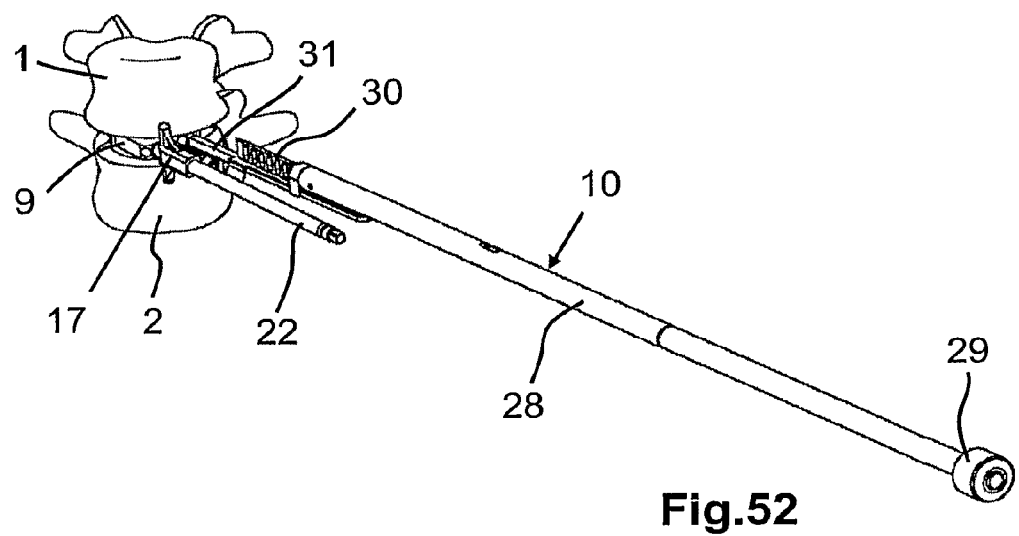
FIG. 52: Trial implant 9 with adjustable stop 17, inserted between a superior vertebra 1 and an inferior vertebra 2, and chisel 10 having a fit-in guidance 31 and a chisel blade 30, attached to a chisel shank 28 with impact head 29.
Figure 53:
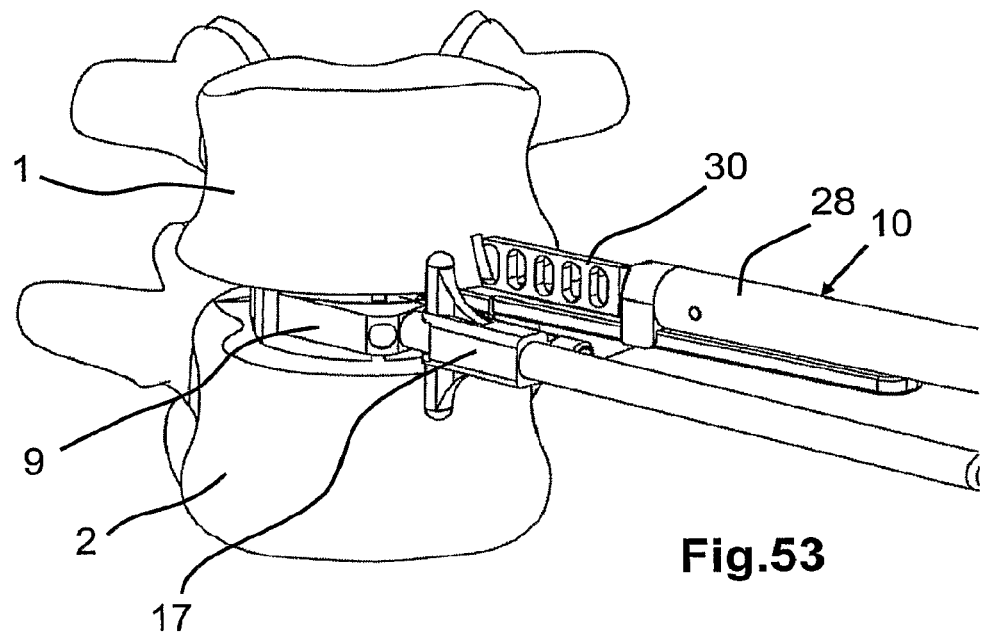
FIG. 53: Trial implant 9 with adjustable stop 17, inserted between a superior vertebra 1 and inferior vertebra 2, and chisel 10, attached to a chisel shank 28, with retracted chisel blade 30.
Figure 54:
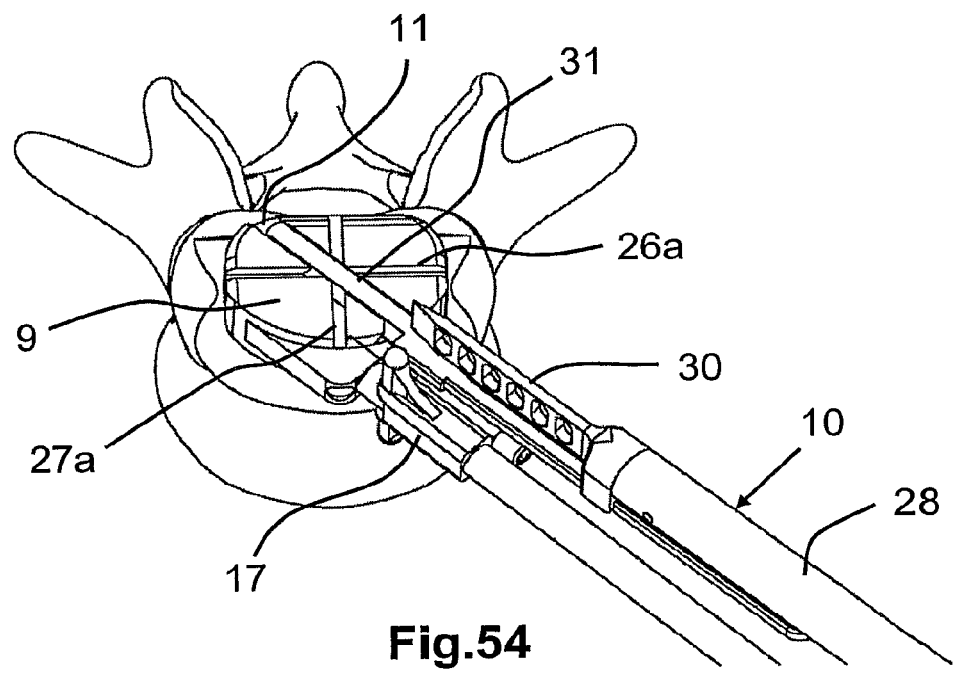
FIG. 54: Plan view of a trial implant 9 having sighting slots 26a and 27a, with adjustable stop 17, inserted between a superior vertebra 1 and an inferior vertebra 2, and chisel 10 with a fit-in guidance 31 and a chisel blade 30 attached to a chisel shank 28, with retracted chisel blade 30 before penetration into the guide slot 11.
Figure 55:
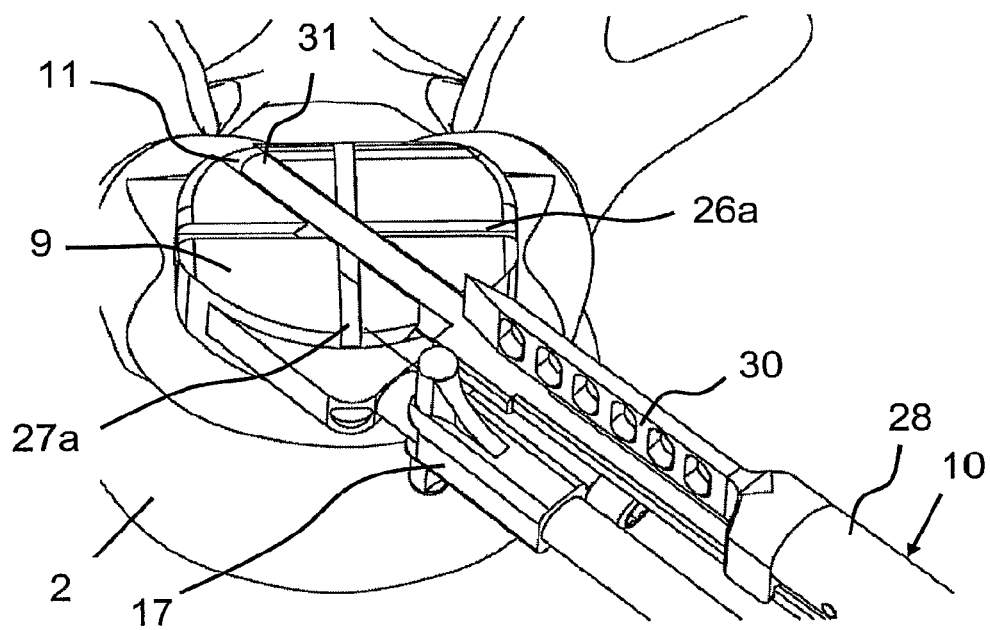
FIG. 55: Plan view of a trial implant 9 having sighting slots 26a and 27a, with adjustable stop 17, inserted between a superior vertebra 1 and an inferior vertebra 2, and chisel 10 with a fit-in guidance 31 and a chisel blade 30 attached to a chisel shank 28, with retracted chisel blade 30 before penetration into the guide slot 11.
Figure 56:
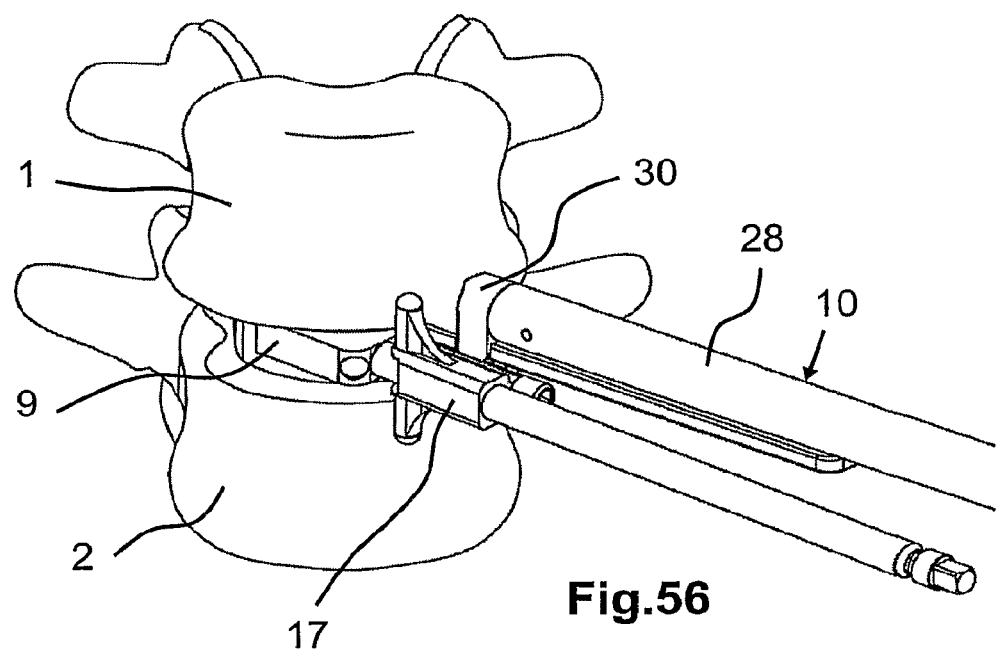
FIG. 56: Trial implant 9 having adjustable stop 17, inserted between a superior vertebra 1 and an inferior vertebra 2, and chisel 10, attached to a chisel shank 28, with tapped-in chisel blade 30.
Figure 57:
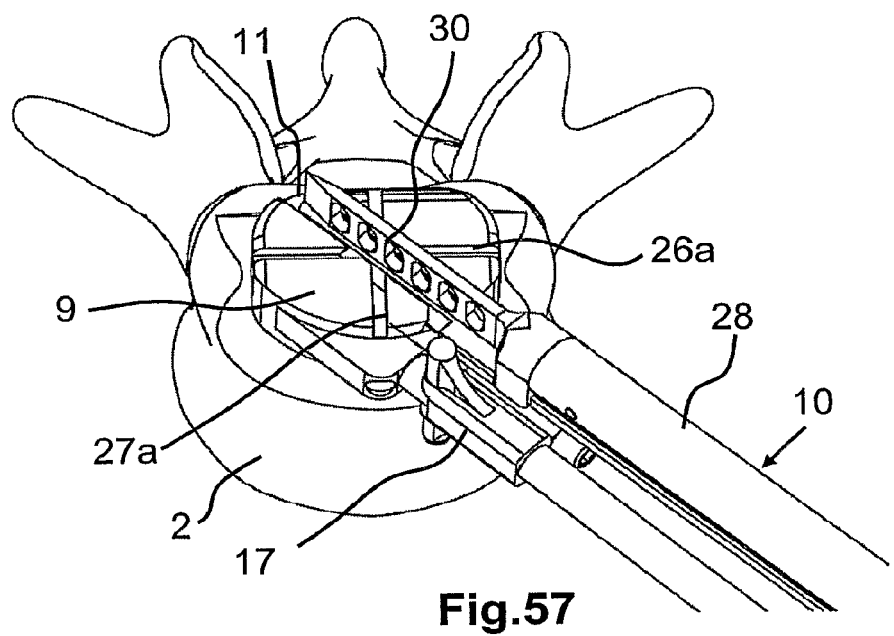
FIG. 57: Plan view of a trial implant 9 with sighting slots 26a and 27a, with adjustable stop 17, inserted between a superior vertebra 1 and an inferior vertebra 2, and chisel 10 and a chisel blade 30, attached to a chisel shank 28, with tapped-in chisel blade 30 in the guide slot 11.

The chisel 10 (FIG. 1) is provided in particular for use with an implant 5', 6, 7' (FIG. 18) or a trial implant 9 for the preparation of an intervertebral space 62 for insertion of an intervertebral disc prosthesis. Said chisel has a chisel blade 30 (FIG. 52) and a chisel shank 28 with an impact head 29 on the distal end thereof, the chisel shank 28 being connected to a displaceable guide 31 which can be inserted in particular into at least one of the guide slots 11, 12 (FIG. 55).

Figure 27:
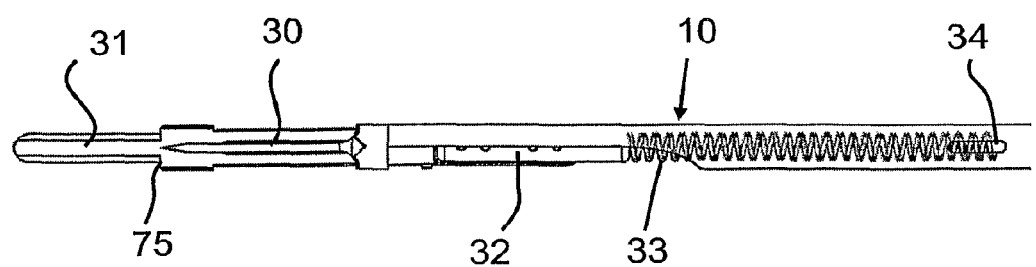
FIG. 27: A chisel 10 in the starting position with chisel blade 20, fit-in guidance 31, with piston 32, spring 33 and rinse slot 34.
Figure 28:
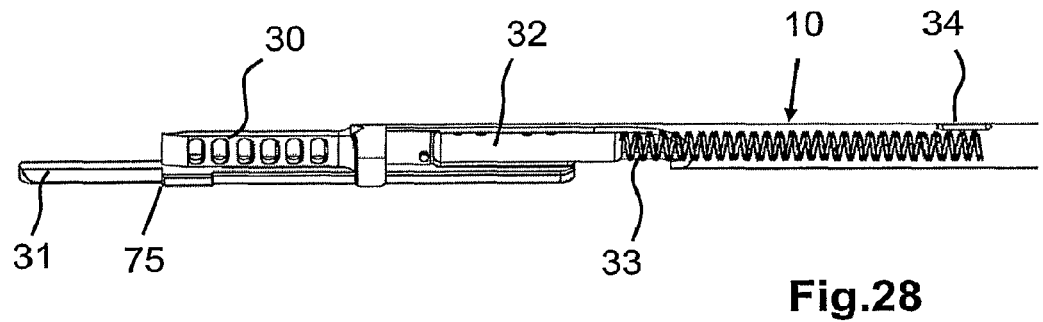
FIG. 28: A chisel 10 in the starting position with chisel blade 30, fit-in guidance 31 with stopper 75, with piston 32, with spring 33 and with rinse slot 34.
Figure 29:
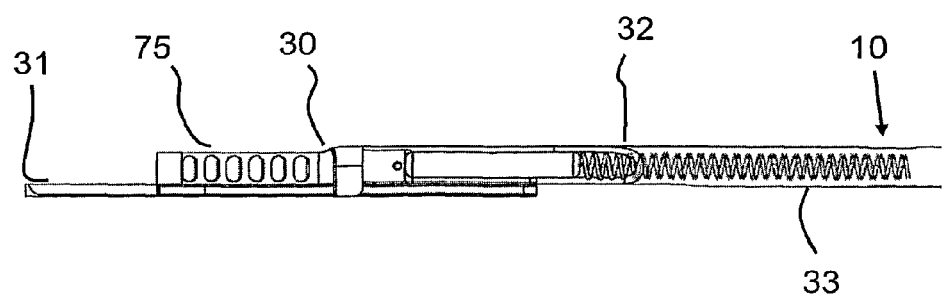
FIG. 29: A chisel 10 in the starting position with chisel blade 30, fit-in guidance 31 with stopper 75, with piston 32, with spring 33.
Figure 30:
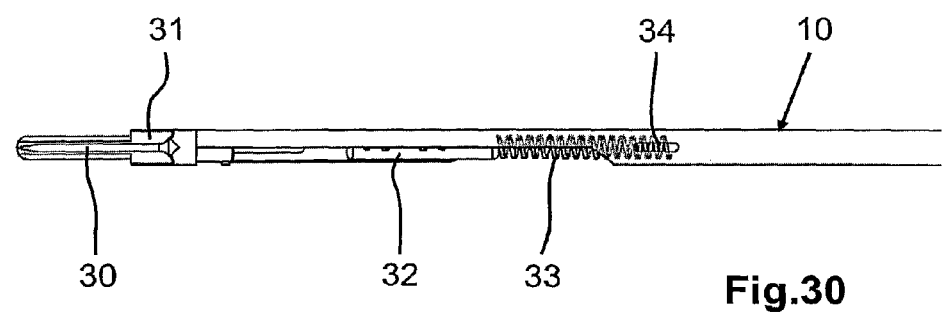
FIG. 30: Plan view of a chisel 10 in the impact position with chisel blade 30, fit-in guidance 31, with piston 32, spring 33 and rinse slot 34.
Figure 31:
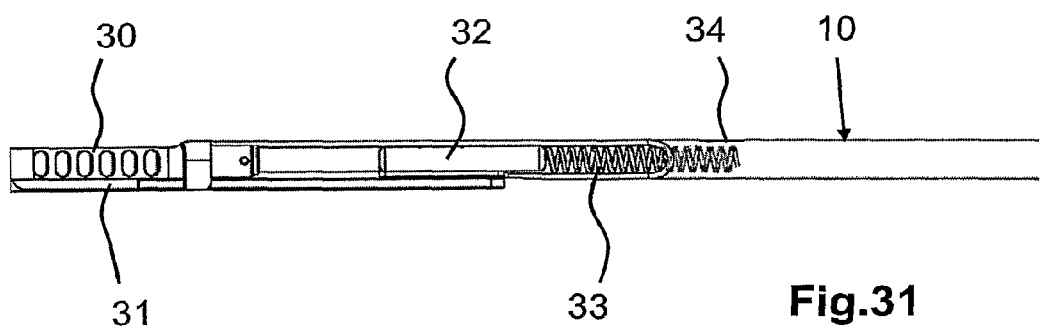
FIG. 31: Side view of a chisel 10.
Figure 32:
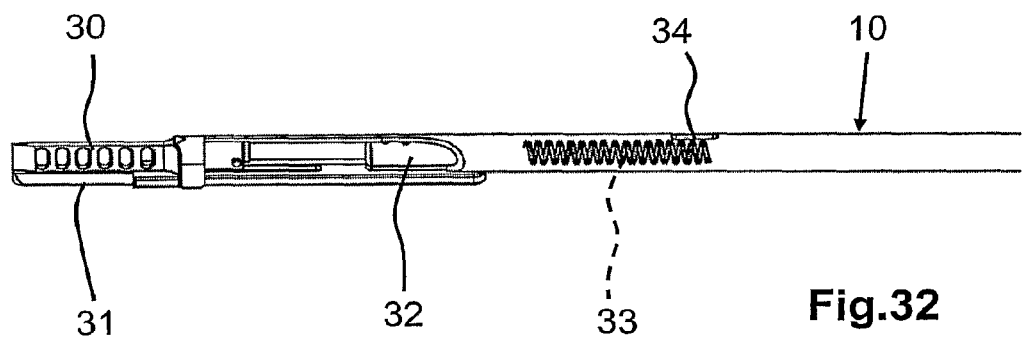
FIG. 32: Oblique view of a chisel 10.
Figure 58:
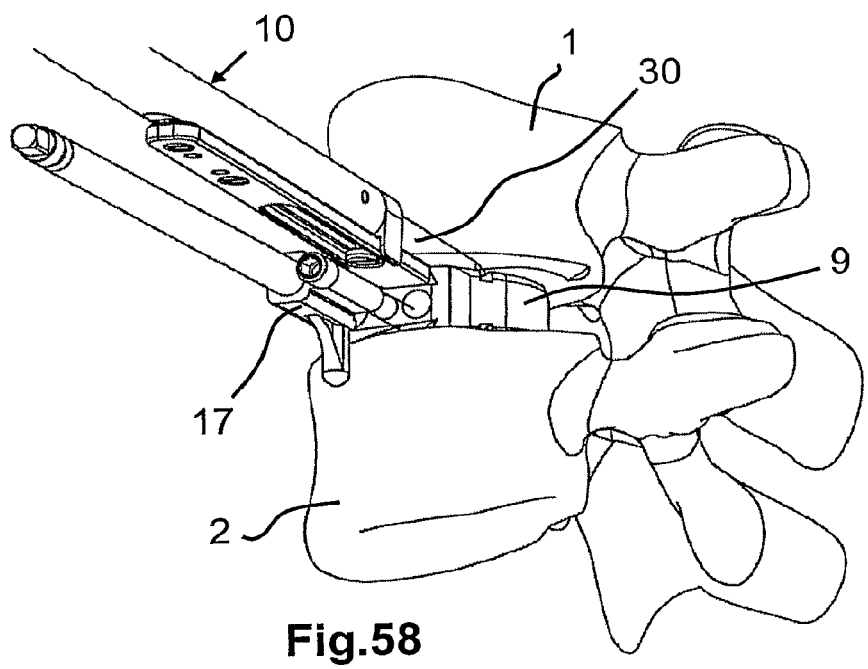
FIG. 58: Bottom view of a trial implant 9, with adjustable stop 17, inserted between a superior vertebra 1 and an inferior vertebra 2, and chisel 10 with tapped-in chisel blade 30.

The guide 31 of the chisel 10 (FIG. 27-29) is spring-loaded against the chisel shank 28 so that, in the unloaded state, it is displaced towards and beyond the proximal end of the chisel blade 30. The guide 31 is connected to a piston 32 which is displaceable under spring load in the interior of the chisel shank 28 and has a stopper 75 for mounting on the lateral surface 65 (FIGS. 55, 58).

Figure 2:
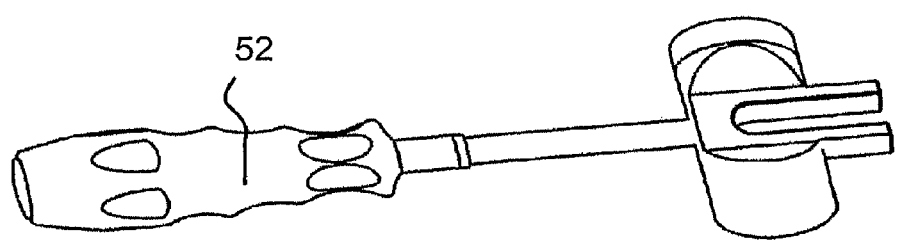
FIG. 2: A mallet 52 having a hammer shape according to the invention and a notch which fits into the shank 28 of the monochisel 10.
Figure 3:
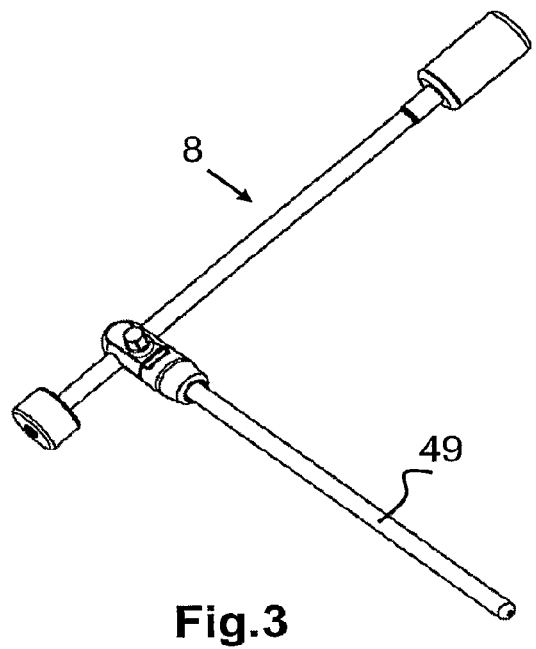
FIG. 3: A handle for the trial implant 8. The handle 49 is held either by an operating theatre nurse or a frame (e.g. Synframe®, trademark of Synthes) while the trial implant is being positioned by impact on the impact head.
Figure 4:
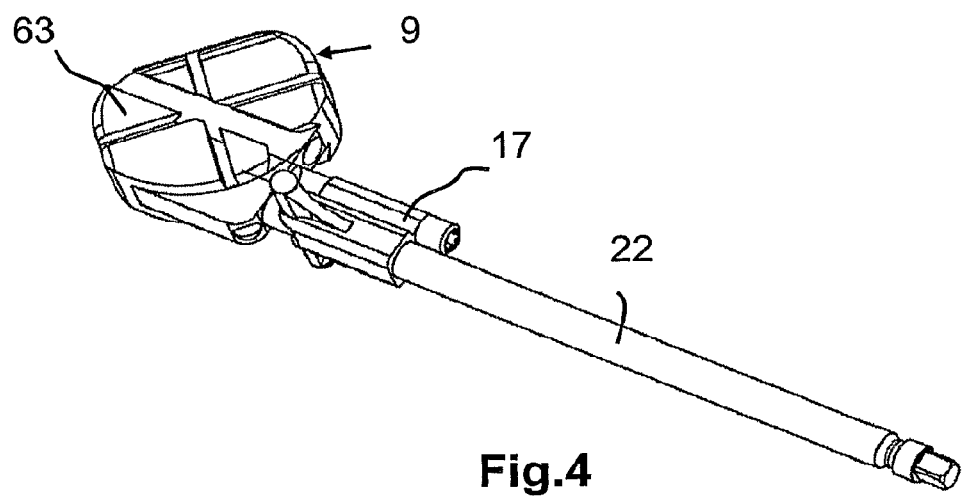
FIG. 4: Trial implant 9 having shaft 22 and an adjustable stop 17 as an adjustable stopper, superior bearing surface 63.
Figure 5:
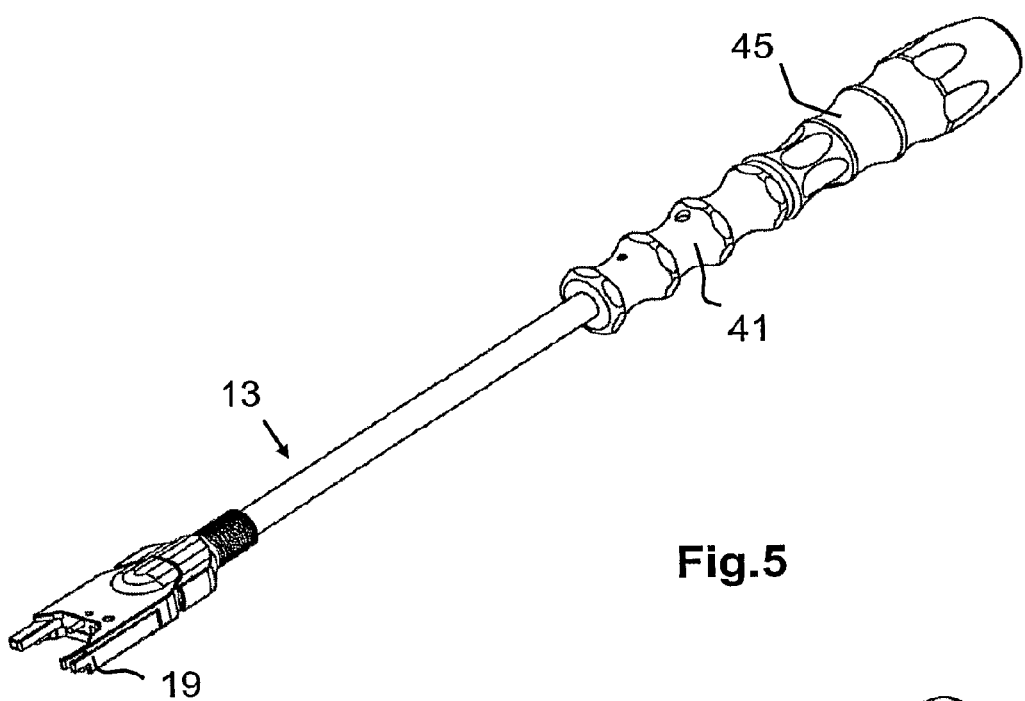
FIG. 5: An inserter 13 having a collet 19, actuating handle 41 and hand grip 45.
Figure 6:
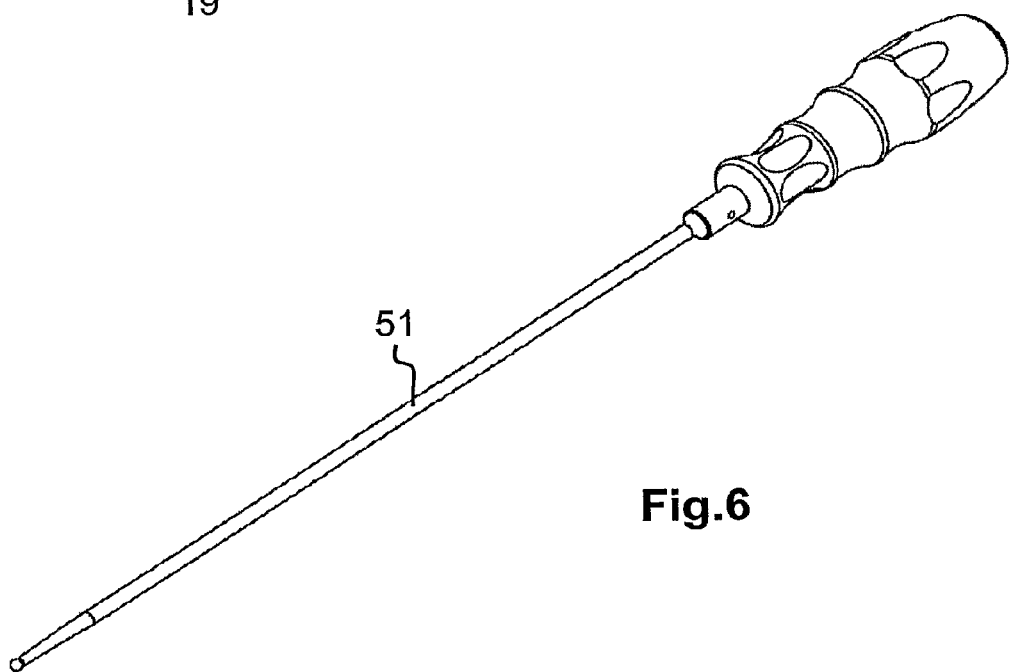
FIG. 6: An impact bar 51 for tapping the trial implant 9 into the intervertebral space 62.
Figure 7:
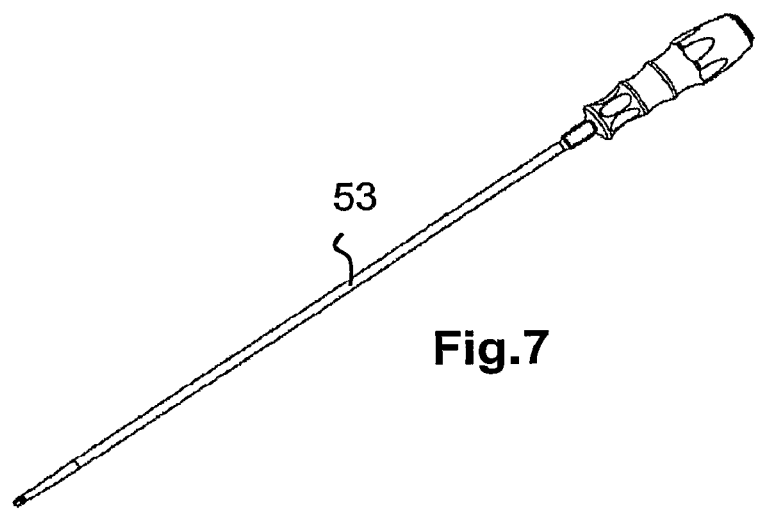
FIG. 7: A screwdriver 53 for use with a stopper according to the invention.
Figure 8:
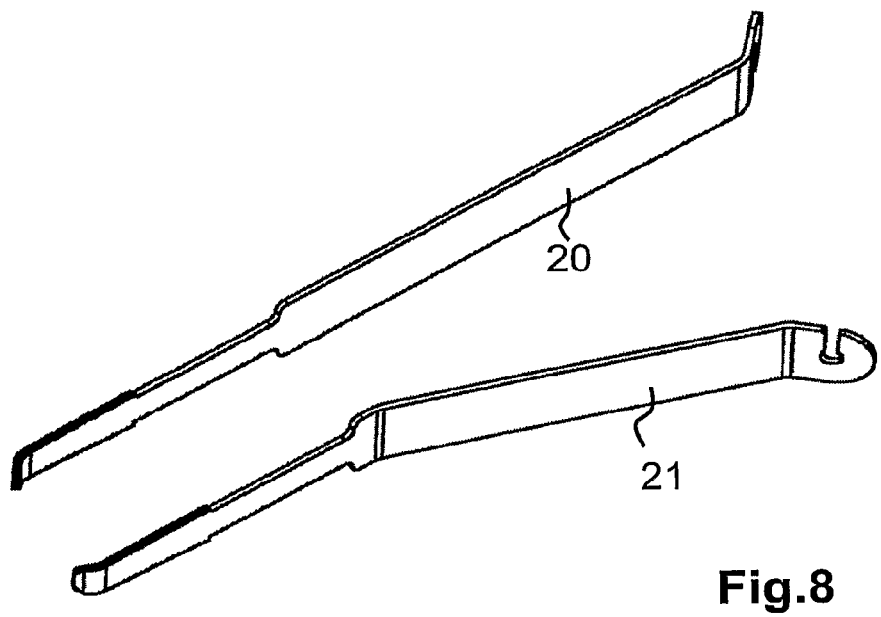
FIG. 8: Struts 20, 21.
Figure 9:
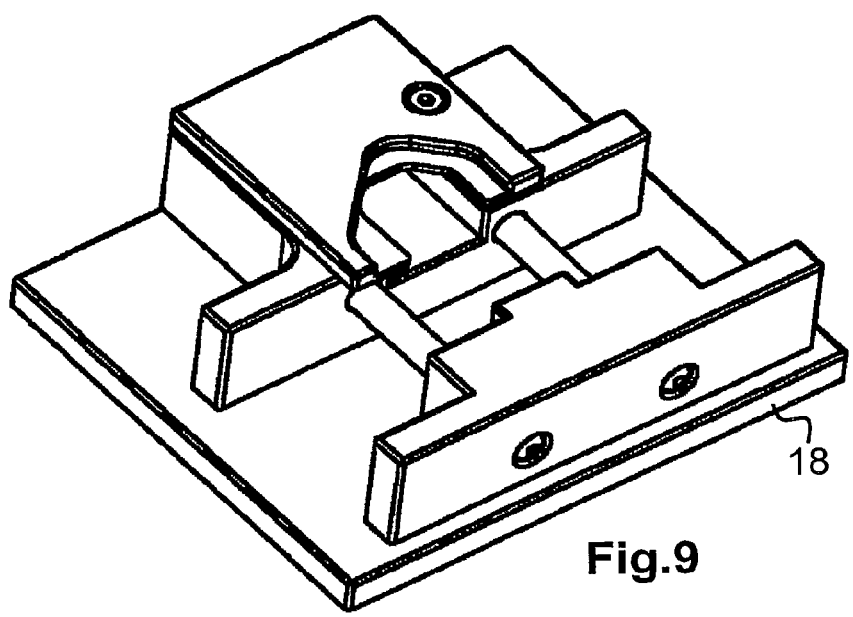
FIG. 9: An assembly tool 18 for assembly of an implant on site.
Figure 10:
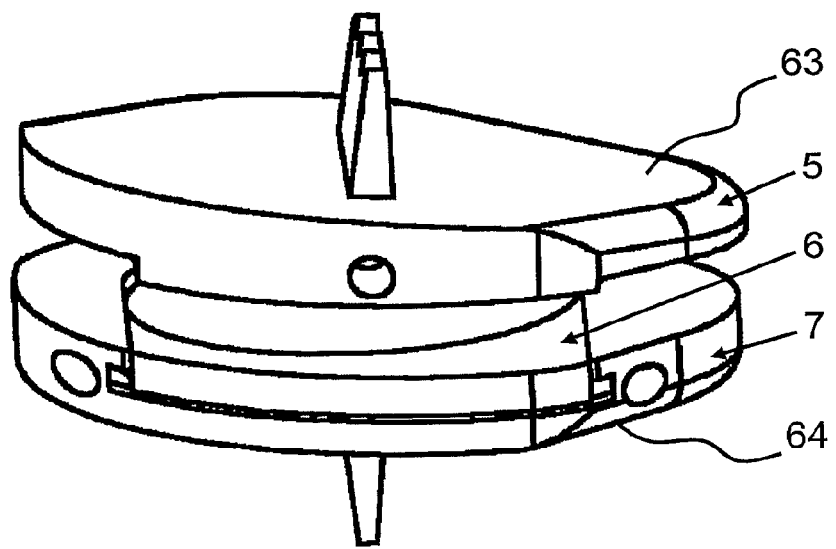
FIG. 10: An implant 5, 6, 7 with superior 63 and inferior 64 bearing surface, view in the direction of an anchorage keel.
Figure 11:
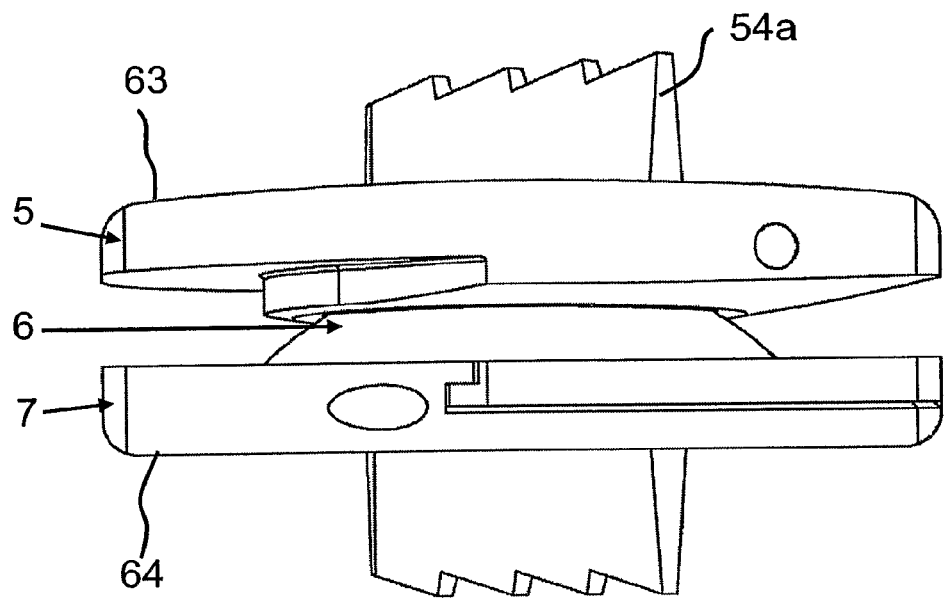
FIG. 11: The implant 5, 6, 7 with superior 63 and inferior 64 bearing surface, anchorage keel 54a; view in the anterior-posterior (AP) direction.

The implant 5', 6, 7' (FIG. 18) or trial implant 9 (FIG. 20-23) is provided as a set comprising a chisel 10 and the associated tools, such as, for example, mallet 52 (FIG. 2) and impact bar 51 (FIG. 6) and screwdriver 53 (FIG. 7).

According to the invention, a pre-trial implant 79 (FIG. 70-73) for the preparation of an intervertebral space 62 is also used if required. The pre-trial implant 79 is substantially produced from a X-ray-transparent, approximately rectangular or trapezoidal frame 76 which contains a compound slide formed from two X-ray-visible spindles 77a, 77b. The carriage body 78 is firmly connected to a positioning bar 80 and is oriented at an angle to one of the two spindles 77a which corresponds to the approach angle e. The positioning bar 80 projects through the frame 76.

The carriage body 78 of the pre-trial implant 79 (FIG. 70-73) can also carry an X-ray-visible marker 96.

Figure 65:
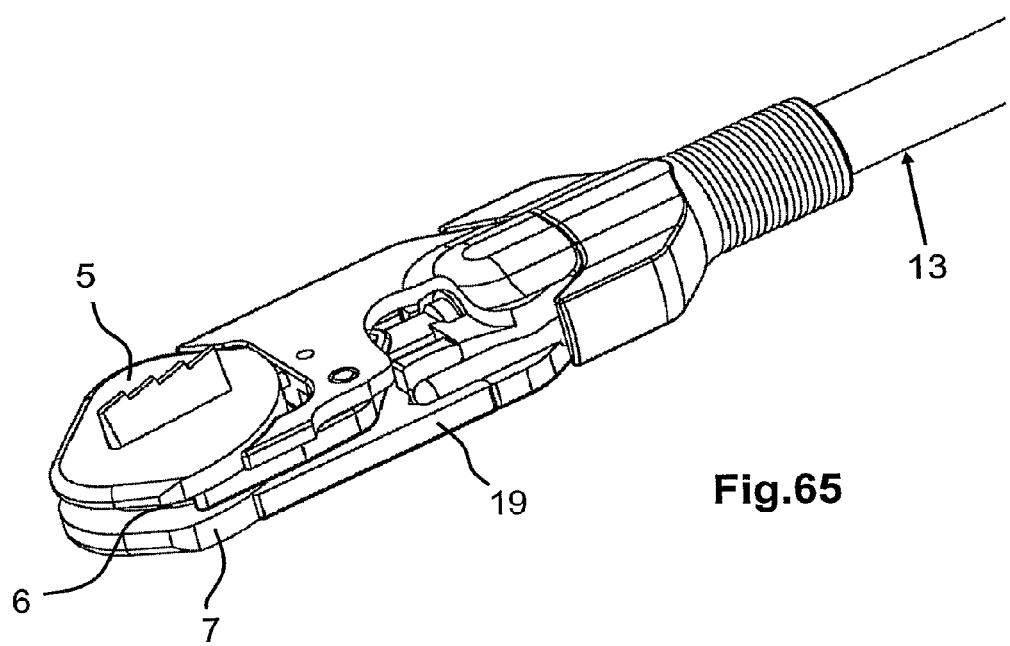
FIG. 65: Inserter 13 with the collet 19 and the 45° implant 5, 6, 7 (all in one)
Figure 66:
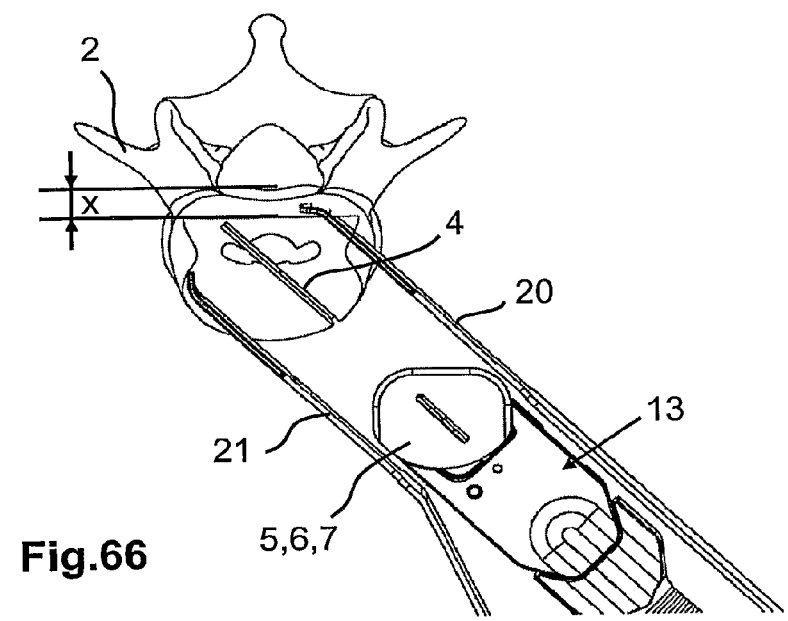
FIG. 66: Plan view of the inferior vertebra 2 with the chiselled groove 4 at the distance x from the spinal canal, with inserted struts 20 and 21, and with the inserter 13 for the insertion of the 45° implant 5, 6, 7 all in one.
Figure 81:
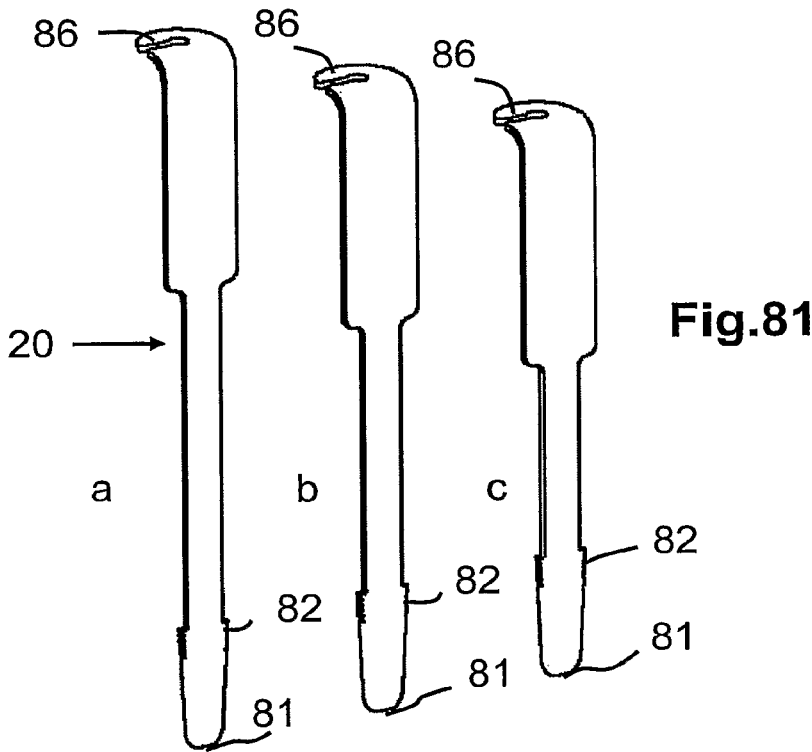
FIG. 81a,b,c: Strut 20 in 3 different sizes with a proximal area 81, a blade having edges 82 and a distal end 86.
Figure 82:
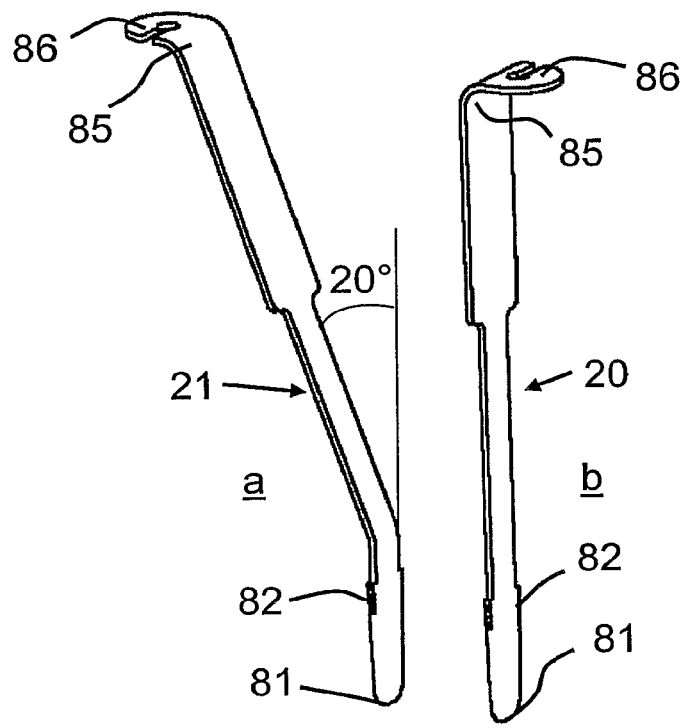
FIG. 82a: Angled strut 21 with a proximal area 81, a blade having edges 82, distal area 85 and a distal end 86, the two struts (20, 21) being wedge-shaped at the angle of lordosis in their proximal area 81 and being medially curved, e.g. at about 20° at their proximal end.
FIG. 82b: Straight strut 20 with a proximal area 81, a blade having edges 82, distal area 85 and a distal end 86, the two struts (20, 21) being wedge-shaped at the angle of lordosis in their proximal area 81.
Figure 83:
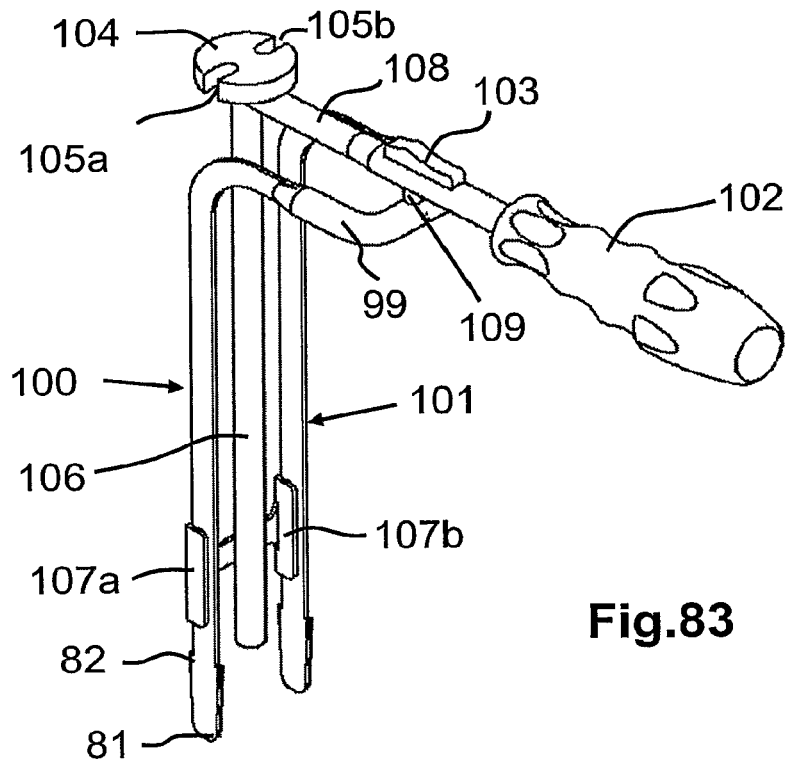
FIG. 83: Struts 100, 101, connected by a handle 99, guided in rails 107a,b. With the handle 102, the handle is connected to the support rod 108 by a lock 103 by means of lock 109. By tapping on the impact head 104 having recesses 105a,b for screwdriver 53 and impact pipe 106, the struts 100, 101 which are guided by the rails 107a,b can slide in the intervertebral space. The struts have a proximal area 81 having edges 82.
Figure 84:
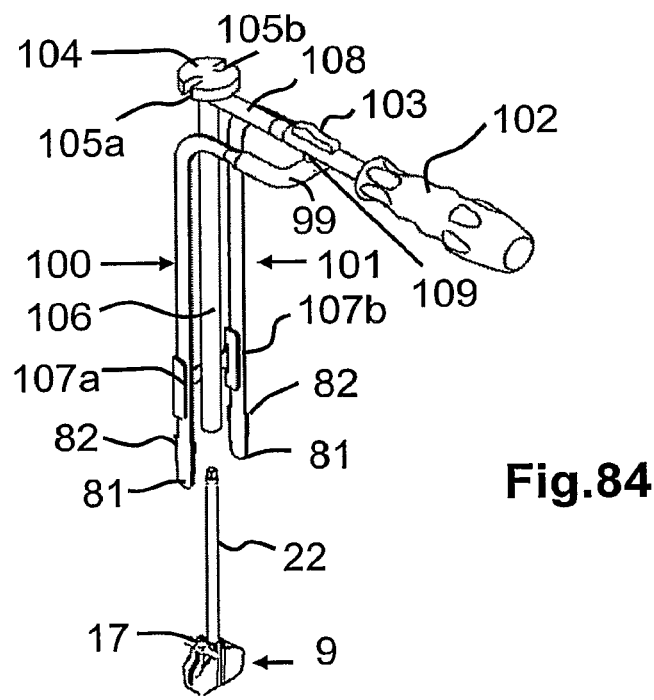
FIG. 84: According to FIG. 83 but with a trial implant arranged underneath. The trial implant 9 can be pushed into the impact pipe 106 by means of the shank 22. An adjustable stop 17 is present on the trial implant.
Figure 85:
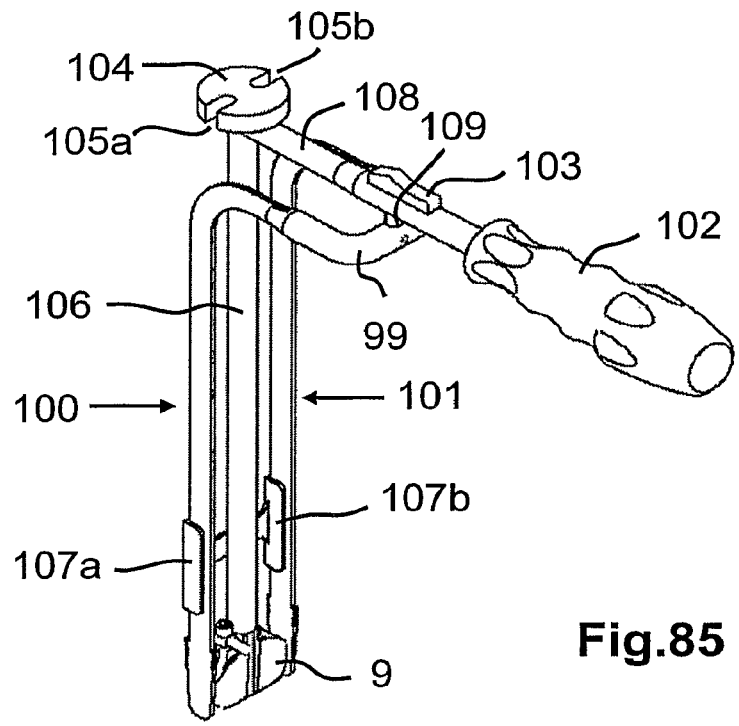
FIG. 85: According to FIG. 83 or FIG. 84. The trial implant 9 is pushed into the impact pipe 106 by means of the shank 22.
Figure 86A:
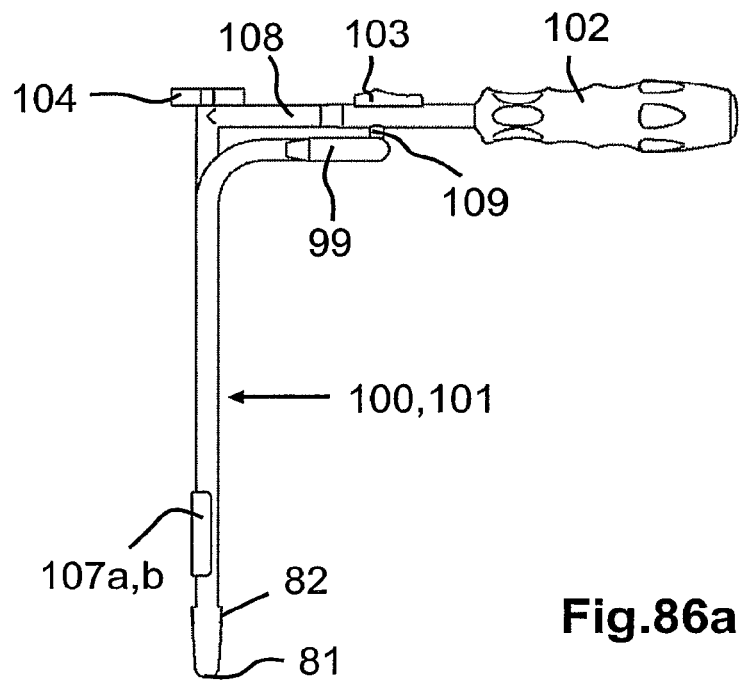
FIG. 86a: Side view of a strut 100, 101, connected by a handle 99, guided in rails 107a,b. With the handle 102, the handle 99 is connected to the support rod 108 via a lock 103 by means of lock 109. By tapping on the impact head 104, the struts 100, 101 which are guided by the rails 107a,b can slide in the intervertebral space 62 (not shown). The struts have a proximal area 81 having edges 82.
Figure 86B:
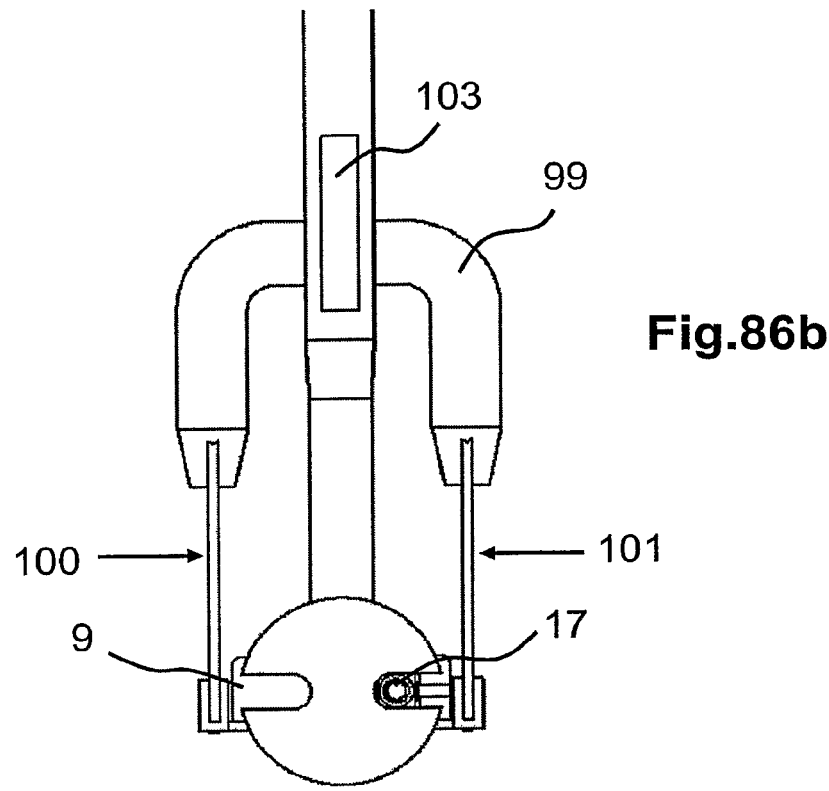
FIG. 86b: Plan view of a strut 100, 101, connected by a handle 99, with lock 103. An adjustable stop 17 is present on the trial implant 9.
Figure 86C:
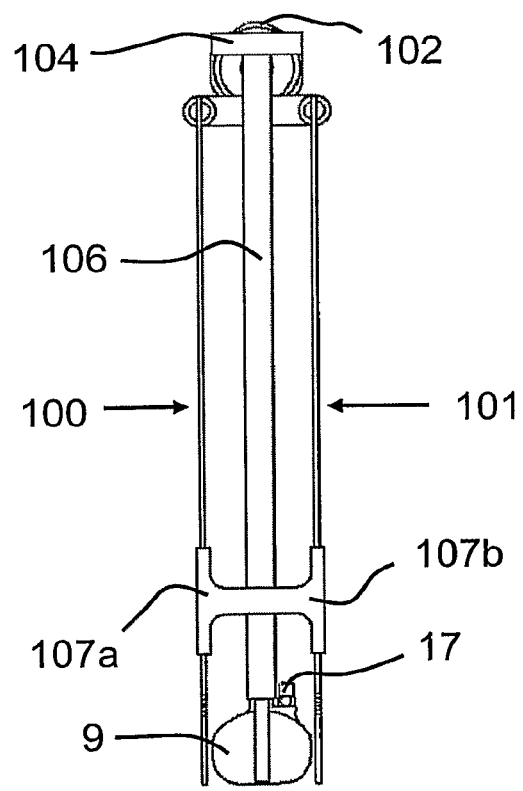
FIG. 86c: Front view of a strut 100, 101, guided in rails 107a,b, and handle 102. By tapping on the impact head 104, struts 100, 101 which are guided by the rails 107a,b can slide in the intervertebral space 62 (not shown). The trial implant 9 is pushed into the impact pipe 106. An adjustable stop 17 is present on the trial implant 9.
Figure 87:
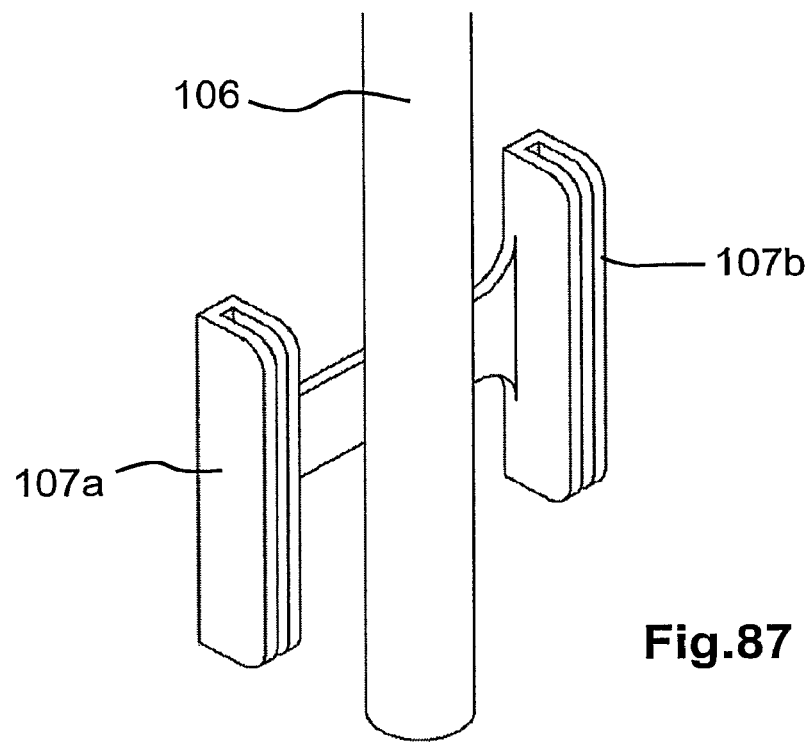
FIG. 87: Detailed view of the guide rails 107a,b with the impact pipe 106.
Figure 88:
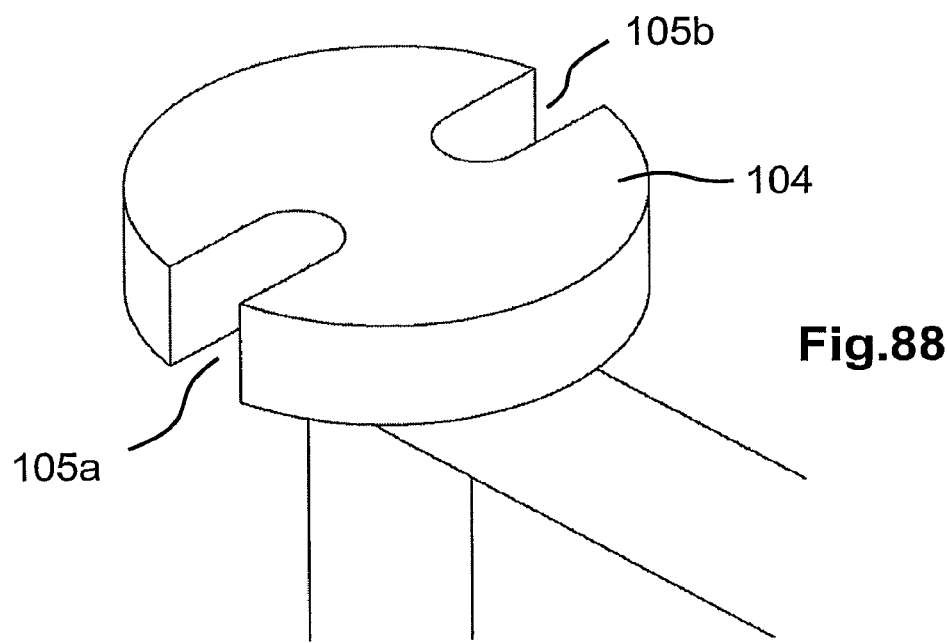
FIG. 88: Detailed view of the impact head 104 with the recesses 105a,b.
Figure 89:
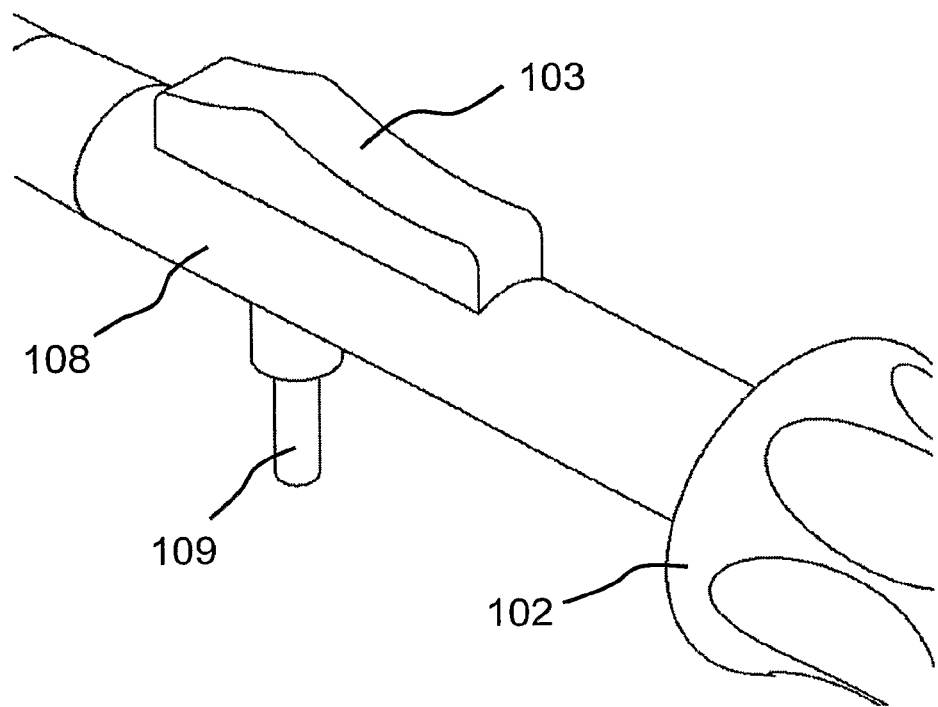
FIG. 89: Detailed view of the lock 103 with locking peg 109, the handle 102 and the support rod 108.
Figure 90A:
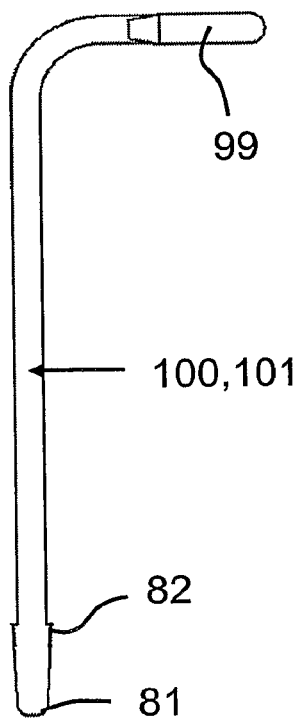
FIG. 90a: Side view of the struts 100, 101 connected to the handle 99, with proximal area 81 and edges 82.
Figure 90B:
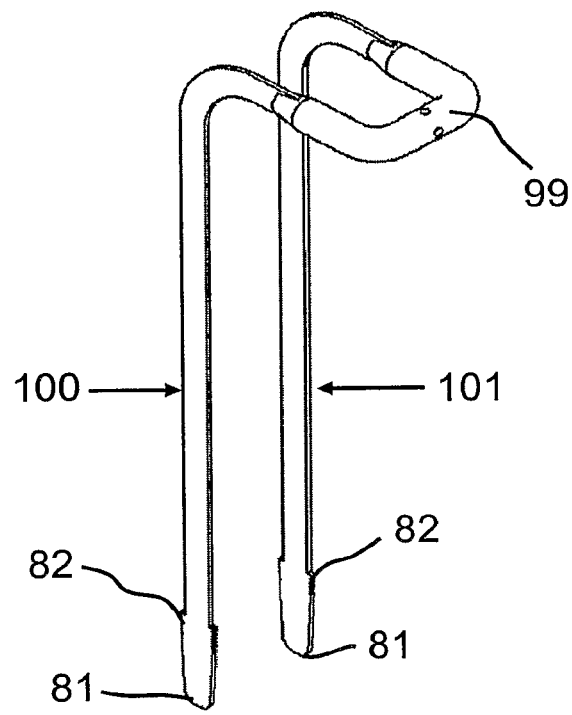
FIG. 90b: Oblique rear view of the struts 100, 101 connected to the handle 99, with proximal area 81 and edges 82.
Figure 90C:
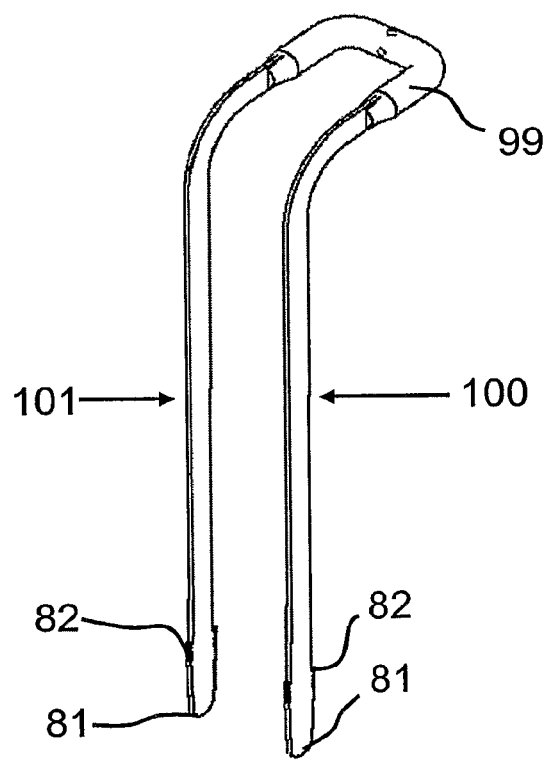
FIG. 90c: Oblique front view of the struts 100, 101 connected to the handle 99, with proximal area 81 and edges 82.
Figure 91:
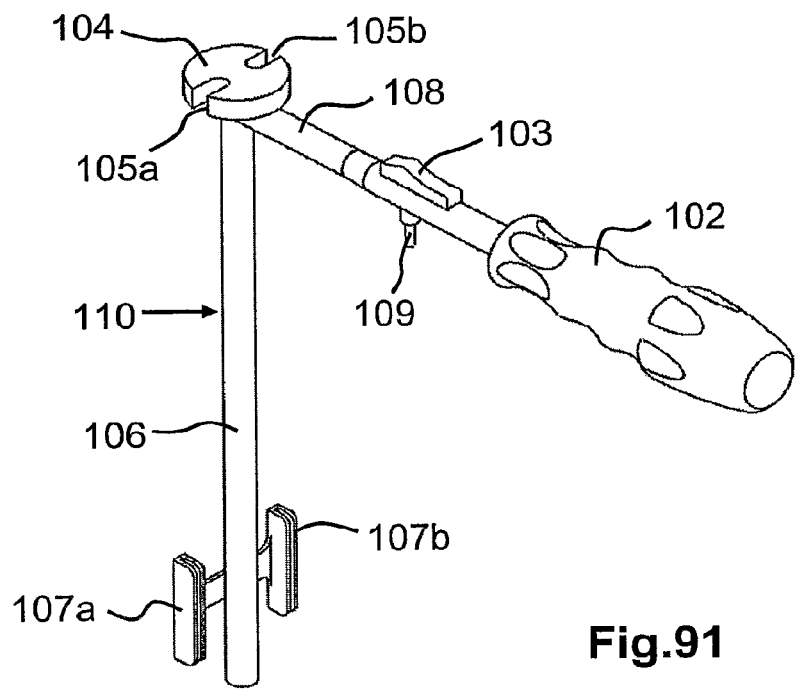
FIG. 91: Holding and impact device 110 (for the struts 100, 101) with handle 102, support rod 108, lock 103, locking peg 109, impact head 104 with recesses 105a,b, impact pipe 106 and guides 107a,b.
Figure 92A:
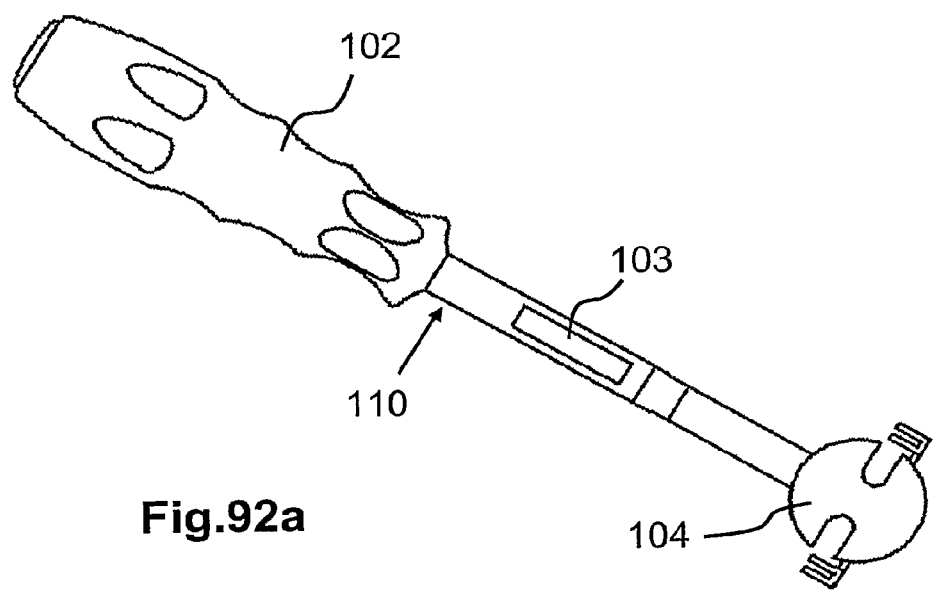
FIG. 92a: Plan view of the holding and impact device 110 (for the struts 100, 101), with handle 102, lock 103 and impact head 104.
Figure 92B:
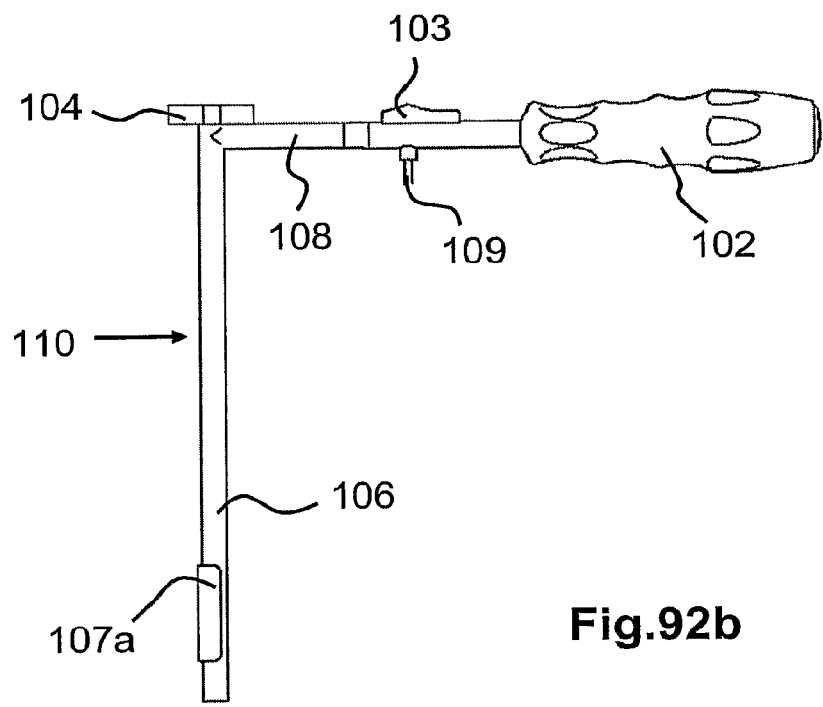
Figure 92C:
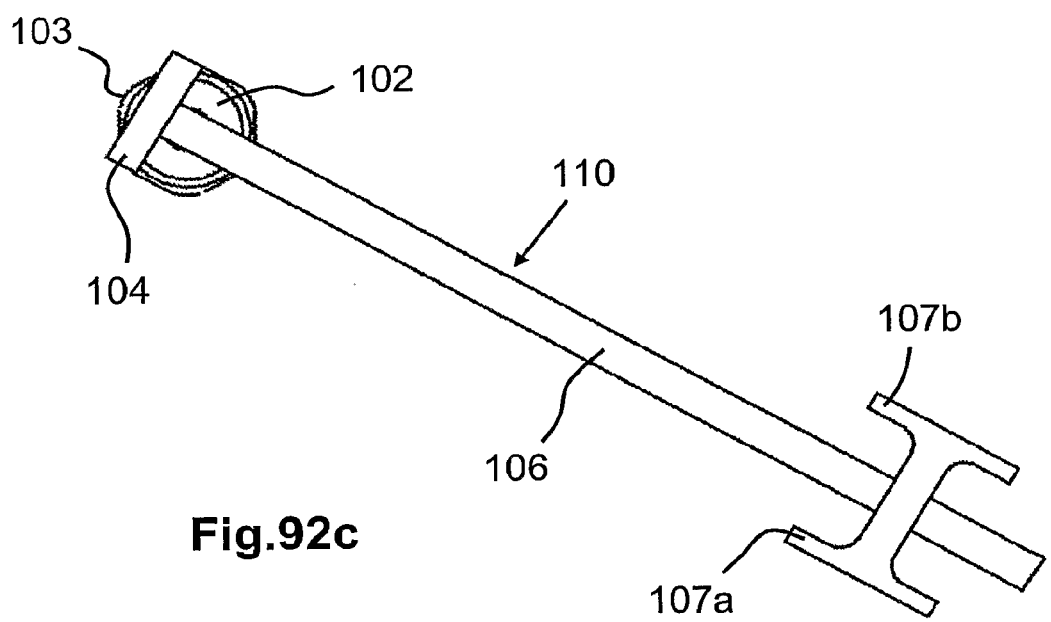
FIG. 92c: Front view of the holding and impact device 110 (for the struts 100, 101), with handle 102, lock 103, impact head 104, impact pipe 106 and guides 107a,b.
Figure 93:
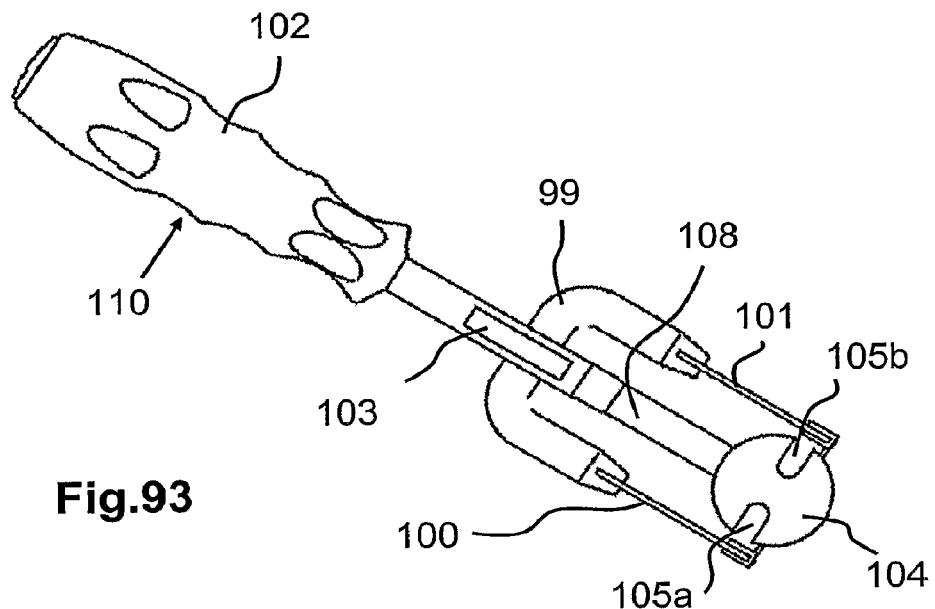
FIG. 93: Plan view of the holding and impact device 110 for the struts 100, 101, with handle 102, lock 103, support rod 108, impact head 104 with recesses 105a,b and struts 100, 101, connected to the handle 99.
Figure 94:
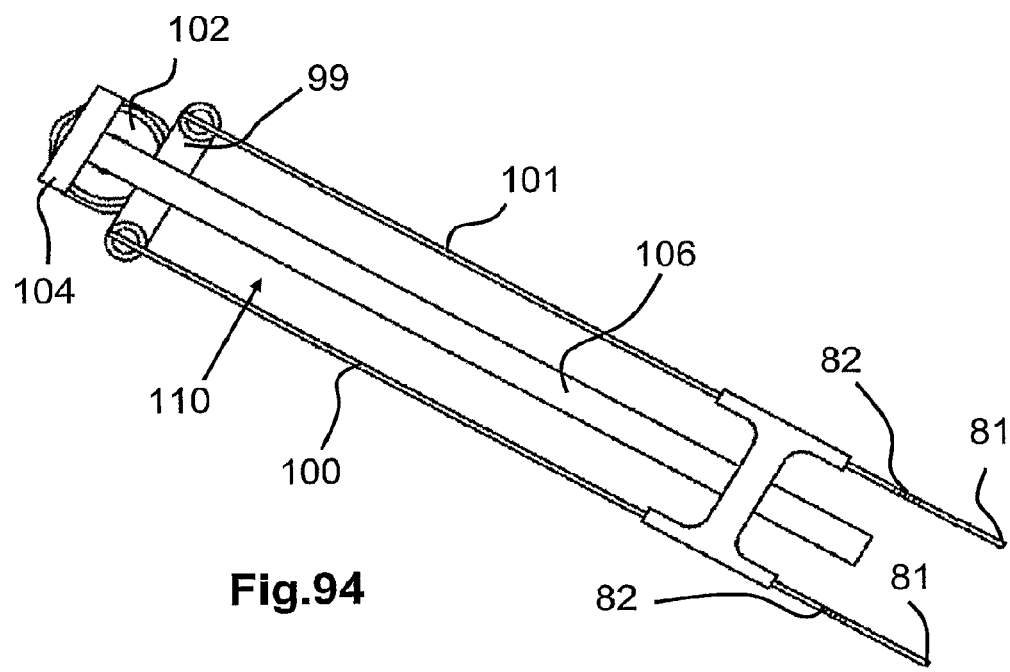
FIG. 94: Front view of the holding and impact device 110 for the struts 100, 101, with handle 102, impact head 104, impact pipe 106 with inserted struts 100, 101 connected to the handle 99, with proximal area 81, with edges 82.
Figure 95:
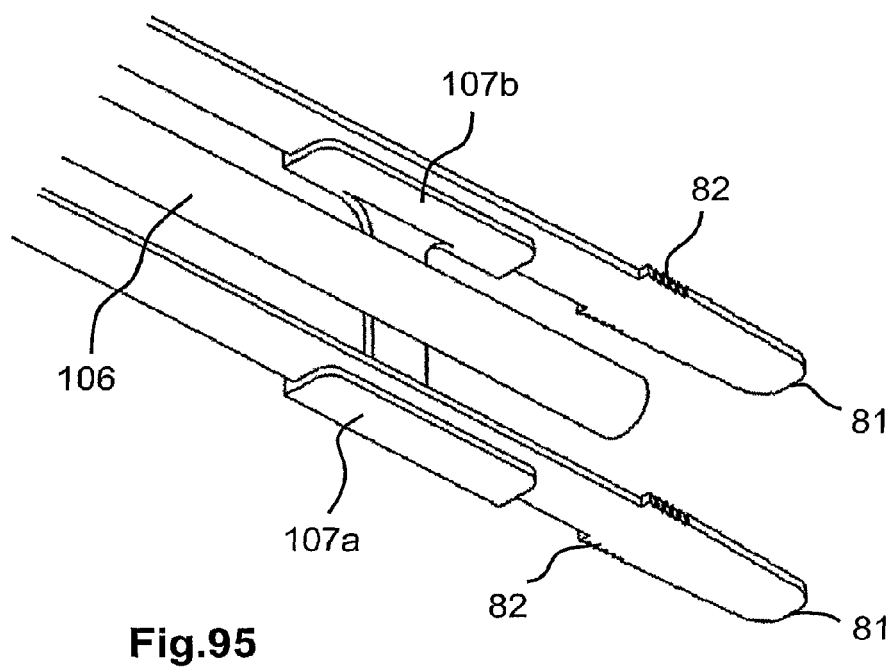
FIG. 95: Impact pipe 106 with guide 107a,b and inserted struts 100, 101 with proximal area 81 and edges 82.

For keeping the intervertebral space 62 (FIGS. 64, 65) open for the discectomy and/or for the insertion of an implant 5, 6, 7 or trial implant 9 or pre-trial implant 79, according to the invention two struts 20, 21 (FIGS. 81, 82) independent of one another and selectable from a group of leaf-like, different struts are formed, the two struts 20, 21 being wedge-shaped at the angle of lordosis in their proximal area and being medially curved at their proximal end.

The struts 20, 21 (FIGS. 64, 65) may be toothed (FIGS. 81, 82) in their proximal area 81 at their edges 82 facing the vertebrae and may have, at their distal end, a coupling device 83 (FIGS. 79, 80) for direct or indirect connection to an attachment frame 84, e.g. Synframe®.

According to the invention, at least one of the two struts 20, 21 (FIGS. 81, 82) is bent medially in its distal area 85, when at least one of the two struts 20, 21 can be formed with reduced height between its proximal and its distal area.

Figure 79:
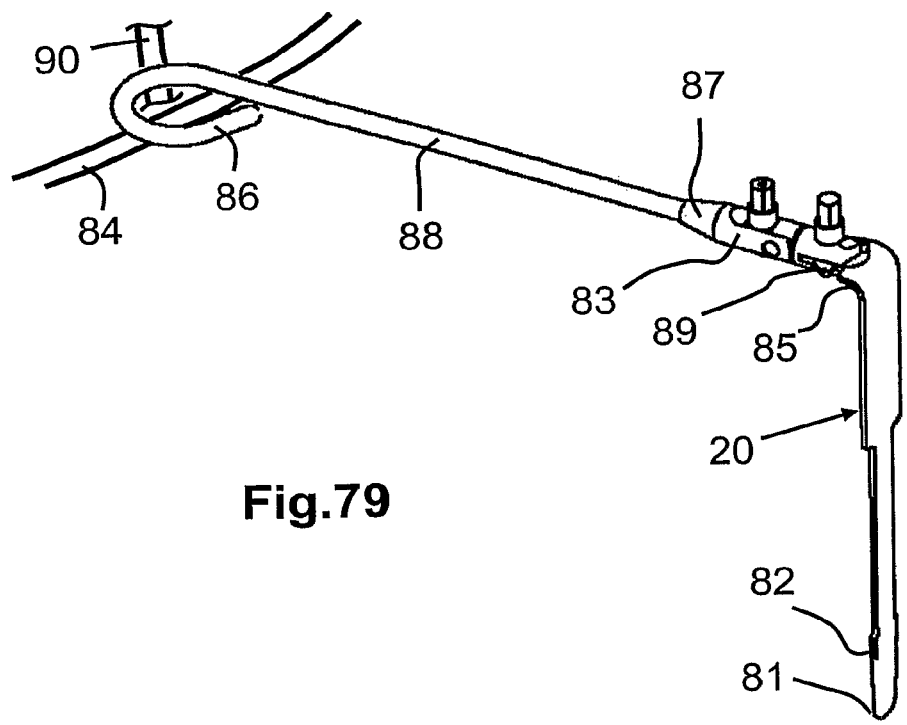
FIG. 79: Side view of a strut 20 (left) having a proximal area 81, a blade having edges 82, distal area 85, a coupling device 83 and a coupling 89. The strut 20 is connected by means of a connecting piece 87 to a handle 88 which is attached at the distal end 86 to an attachment frame 84. The handle 88 can also be attached to an attachment frame 84 which is held by a guide element 19 for lateral support.
Figure 80:
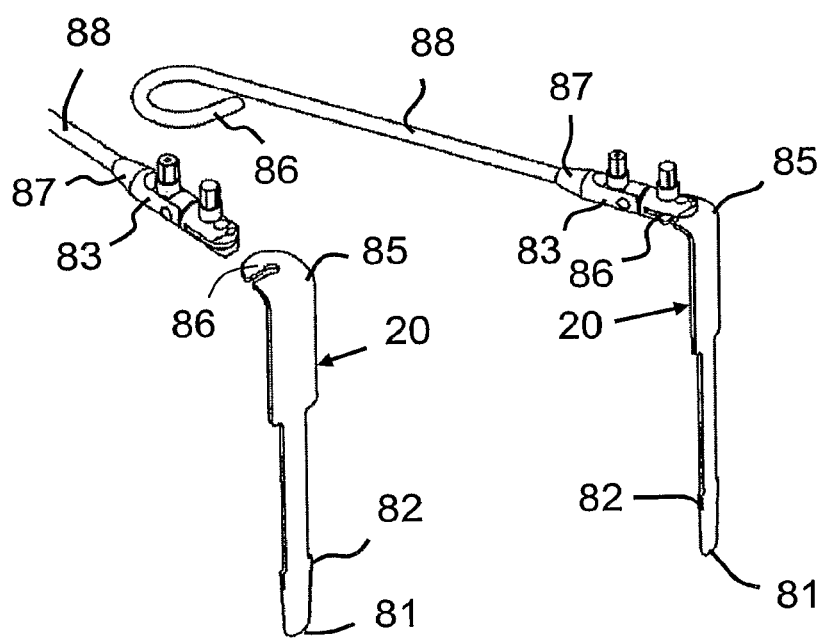
FIG. 80: Left diagram: Strut 20, distal area 85 is separated from a coupling device 83, right diagram: Strut 20 is connected at the distal end to the coupling device 83.

The two struts can be connected at their distal end 86 (FIGS. 81, 82) by means of the connecting piece 87, and the connecting piece 87 can also be connected to a handle 86—preferably by means of detachable coupling 89 (FIGS. 79, 80).

The handle 86 of the struts 20, 21 may have guide elements 90 for lateral support (FIG. 79).

According to the invention, an assembly tool 18 (FIG. 63*a*-*e*) is provided for assembling an intervertebral disc implant according to the invention having a superior and an inferior implant plate 5, 7 and an inlay 6. The assembly tool 18 has a baseplate 91 and a base 92 and a collet 93*a*,*b* in the base 92. The collet 93*a* is formed for interlocking with an implant plate 5 or 7. A batten-like guided sliding element 94 which has an interlocking collet 93*b* for the inlay 6 is coordinated with the base 92. The two implant plates 5, 7 and the inlay 6 can be placed in their collet in such a way that they are correctly positioned relative to one another and, after insertion of the sliding element 94, locked with one another. The base 92 of the assembly tool and the sliding element 94 are connected to one another in a slidable manner by means of parallel guide 95, e.g. by pins 23*a*,*b*.

Figure 97:
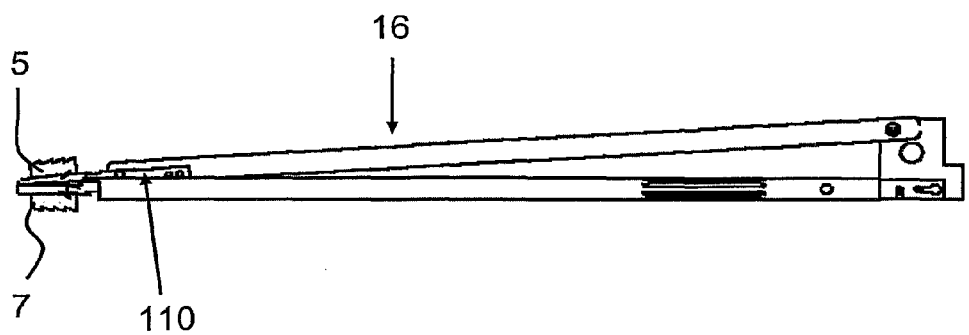
FIG. 97: An inserter 16 with module device 110 for subsequent insertion of an inlay 6 between the upper implant plate 5 and lower implant plate 7.

The intervertebral implant 5, 6, 7 (FIG. 10-14) for insertion into a superior vertebra 1 and an inferior vertebra 2, having a superior part 5, an inferior part 7 and an inlay 6, is designed, according to the invention, as an all-in-one intervertebral implant 5, 6, 7 (FIGS. 64, 65), and it can be inserted at 45° by means of a left oblique anterior approach into a prepared groove 3, 4 in the superior vertebra 1 or inferior vertebra 2 by means of an instrument 13 for insertion at 45°. In the case of a variant according to the invention, the intervertebral implant 5, 7 can be inserted without inlay 6, the inlay 6 subsequently being inserted using another instrument 16 for insertion at 45° (FIG. 97).

Figure 59:
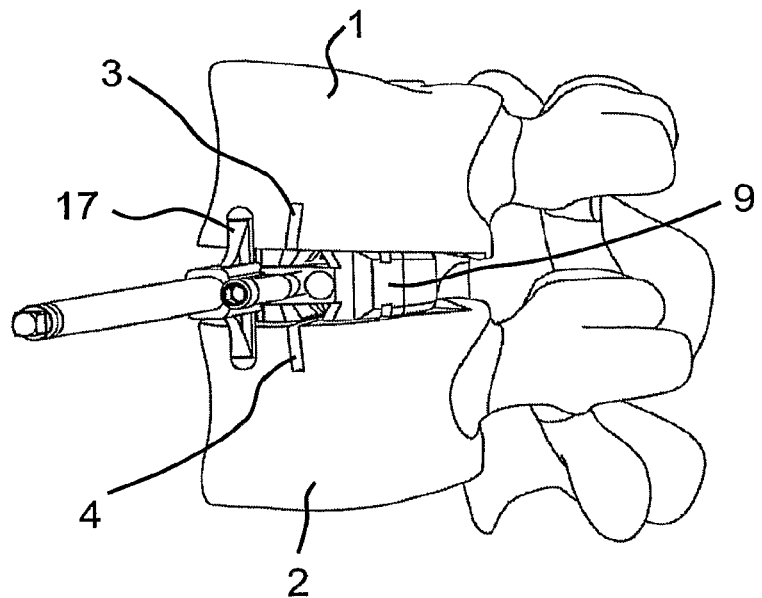
FIG. 59: Side view of groove 3 in the superior vertebra 1 and of groove 4 in the inferior vertebra 2 after chiselling, with inserted trial implant 9 with adjustable stop 17.
Figure 60:
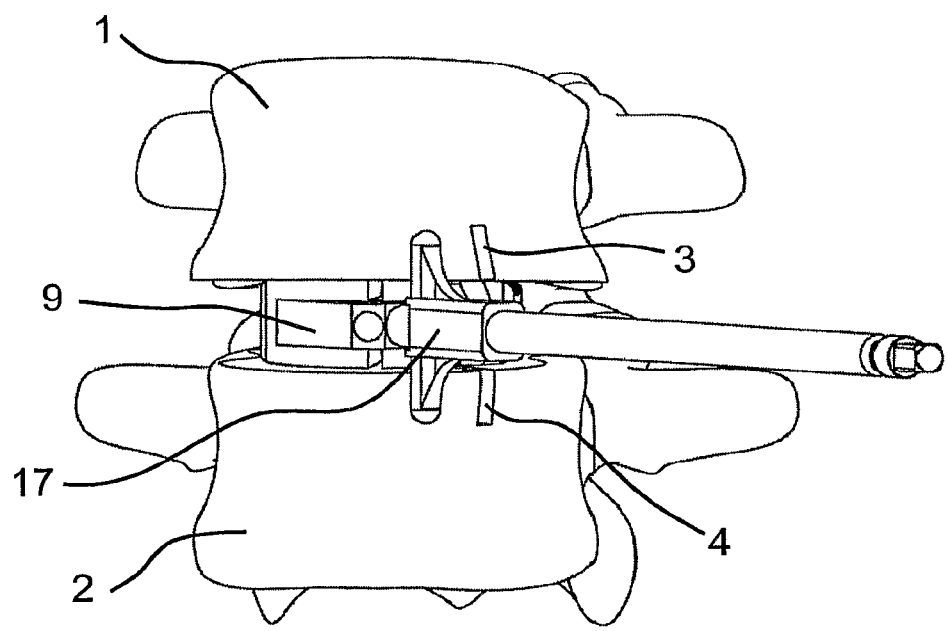
FIG. 60: Front view of groove 3 in the superior vertebra 1 and of groove 4 in the inferior vertebra 2 after chiselling, with inserted trial implant 9 with adjustable stop 17.

The prepared groove 3, 4 (FIGS. 59, 60, 64) in the superior vertebra 1 or inferior vertebra 2 makes an angle of 90° with the respective intervertebral surface in order to permit the best possible retention according to the invention.

Using the instrument 13 (FIG. 33-35, 64-66) for inserting an intervertebral implant 5, 6, 7 at 45°, an intervertebral implant 5, 6, 7 comprising 3 parts all in one can be held and can be inserted at 45° by means of an oblique anterior approach into the intervertebral space.

Using an alternative instrument 16 (FIG. 97) for inserting an intervertebral implant 5, 6, 7 at 45°, first the upper part 5 and lower part 7 of an intervertebral implant 5, 6, 7 can be held at about 45° and then the inlay 6 can be inserted at the same angle of about 45° by means of a left oblique anterior approach.

The components of the implant are preferably offered as a set in a sterilizable box.
Example of Industrial Application After opening of the abdominal cavity for an approach at 45° on the patient's left side, first the intervertebral disc is removed (discectomy) and the intermediate space is cleaned.

For maintaining the distance, the struts 20, 21 or the alternative variant of the struts 100, 101 can be inserted at this point. By tapping on the impact head 104 with recesses 105*a*,*b* for screwdriver 53 and impact pipe 106, the struts 100, 101 which are guided by the rails 107*a*,*b* can slide into the intervertebral space.

A trial implant 9 (FIG. 20-23) is then inserted. Corresponding to the size of the vertebrae, the trial implant 9 is present in the set sizes M or L and the various angles of lordosis. On the basis of his experience and through insertion of different variants, the surgeon finds the optimum size.

The position of the implant is of considerable importance, and the trial implant 9 is therefore exactly aligned by the surgeon with radiographic monitoring, by tapping onto the notches 24*a* and 24*b*.

An adjustable stop 17 prevents the trial implant 9 from penetrating too far into the intervertebral space. By turning the adjusting screw of the adjustable stop 17 by means of a screwdriver, the stopper can be turned forwards or backwards by about 9 mm. A trial implant 9 which has been inserted a track too far can thus be retracted again.

Alternatively, in order to find the exact middle for the implant, a pre-trial implant (FIG. 70-73), which is likewise aligned by means of X-ray monitoring, can be used.

The shank 22 of the trial implant 9 is fixed on the Synframe®, and only thereafter is the chisel 10 introduced into the slot of the trial implant 9, and the upper or the lower groove is chiselled into the upper or lower vertebra by tapping on the impact head (FIG. 53-58).

The groove must be at right angles to the respective intervertebral surface so that the implant rests against the superior and inferior surface with interlocking. According to the invention, the surgeon leaves the chisel in the bone after the upper chiselling and then performs the lower chiselling with a second chisel which results in better correspondence of the grooves with the implant keels.

Figure 61:
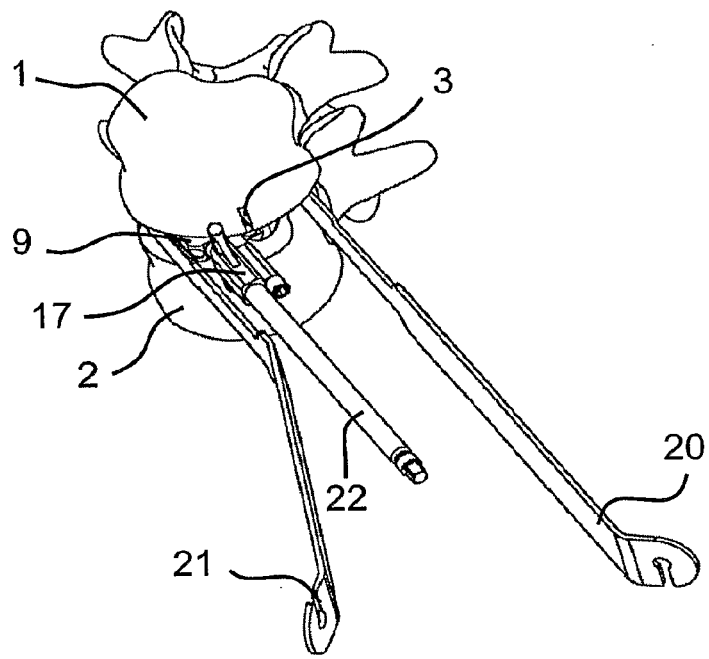
FIG. 61: Oblique view of a superior vertebra 1 and of an inferior vertebra 2 with chiselled groove 3, with inserted trial implant 9 with adjustable stop 17 and shank 22, and with inserted left 20 and right 21 struts.

After the upper and lower grooves have been chiselled in the bones (FIGS. 61, 62), struts 20, 21 are introduced now at the latest to the left and right of the trial implant, unless they are already present, and the trial implant is removed.

Figure 67:
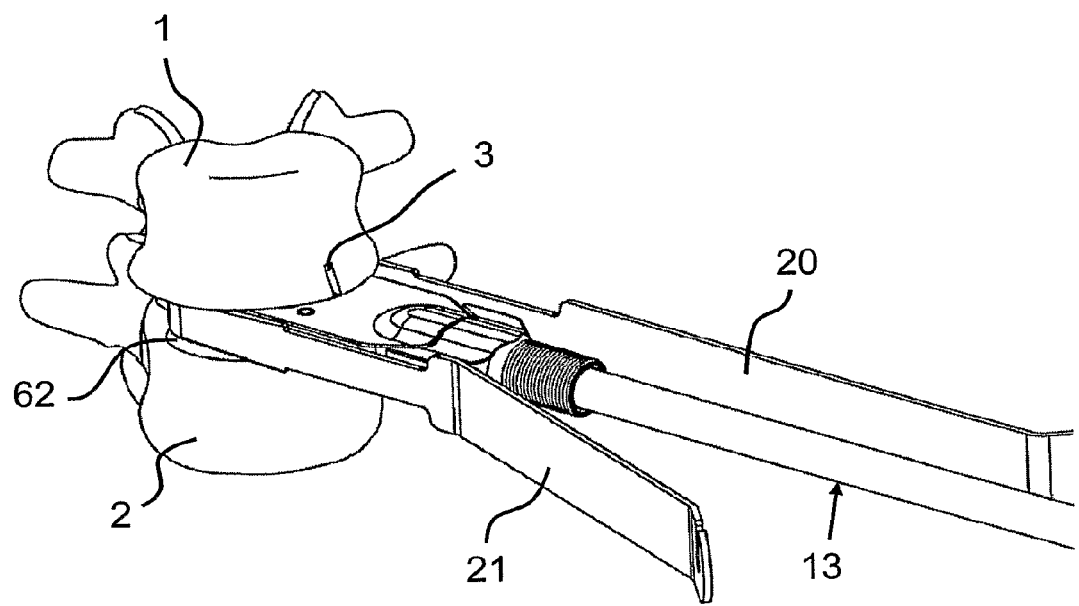
FIG. 67: Oblique view of a superior vertebra 1 and inferior vertebra 2 with the groove 3 in the inserted inserter 13 between the struts 20 and 21 in the intervertebral space 62.
Figure 68:
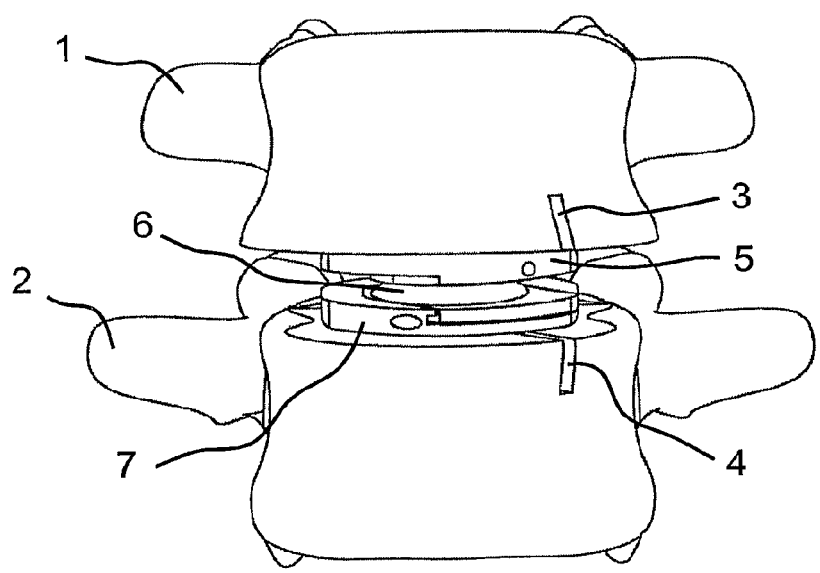
FIG. 68: Front view of an inserted implant 5, 6, 7 between the upper vertebra 1 and the inferior vertebra 2; the keel of the superior plate 5 is guided in the groove 3, and the keel of the inferior plate 7 is guided in the groove 4.
Figure 69:
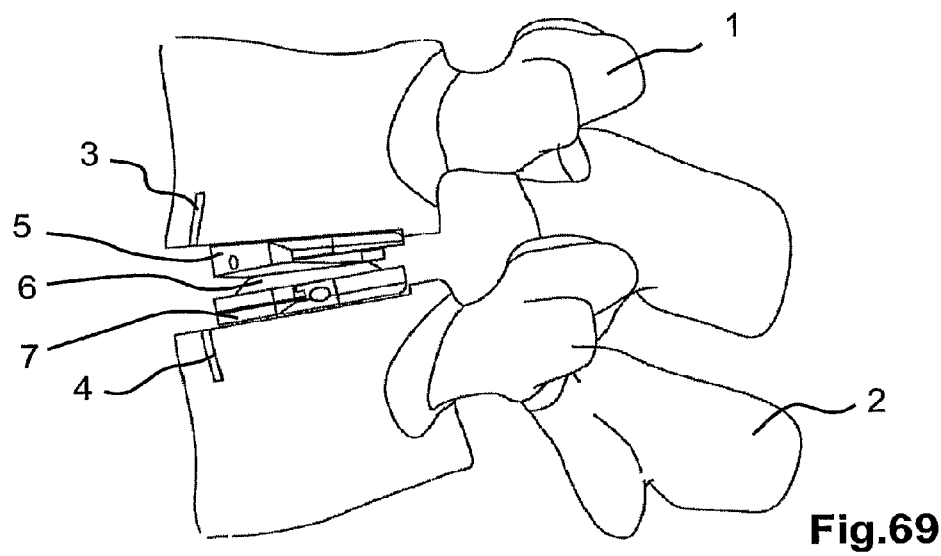
FIG. 69: Side view of an inserted implant 5, 6, 7 between the superior vertebra 1 and the inferior vertebra 2; the keel of the superior plate 5 is guided in the groove 3, and the keel of the inferior plate 7 is guided in the groove 4.
Figure 70:
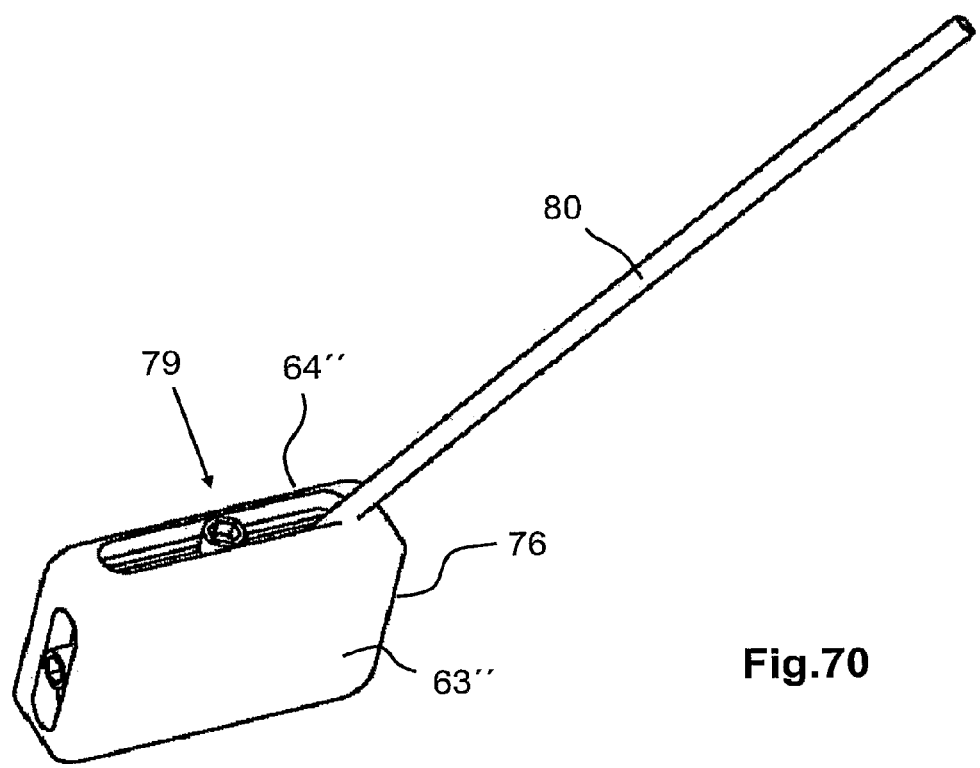
FIG. 70: Oblique view of a pre-trial implant 79 having a frame 76 and a positioning bar 80, and a superior bearing surface 63" and an inferior bearing surface 64"
Figure 71A:
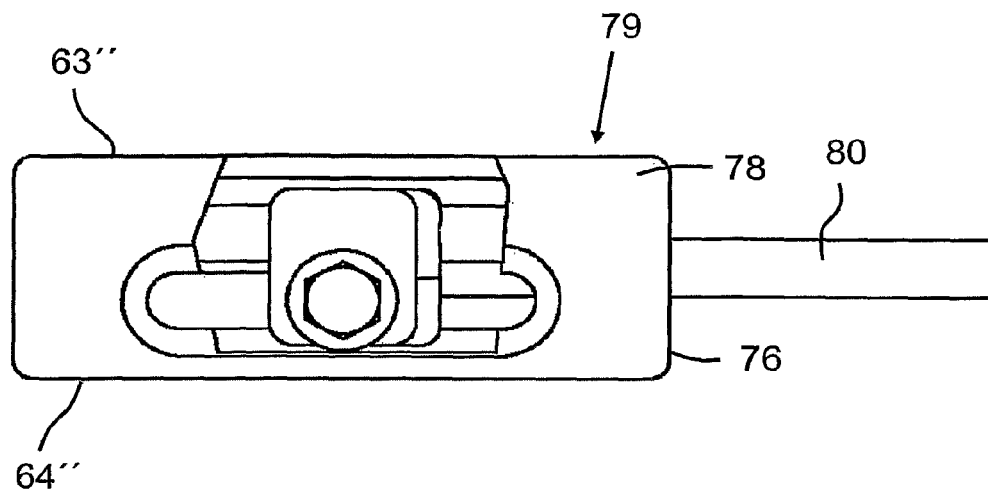
FIG. 71a: Side view of the short side of a pre-trial implant 79 having a frame 76 and a positioning bar 80, with a carriage body 78, and a superior bearing surface 63" and an inferior bearing surface 64"
Figure 71B:
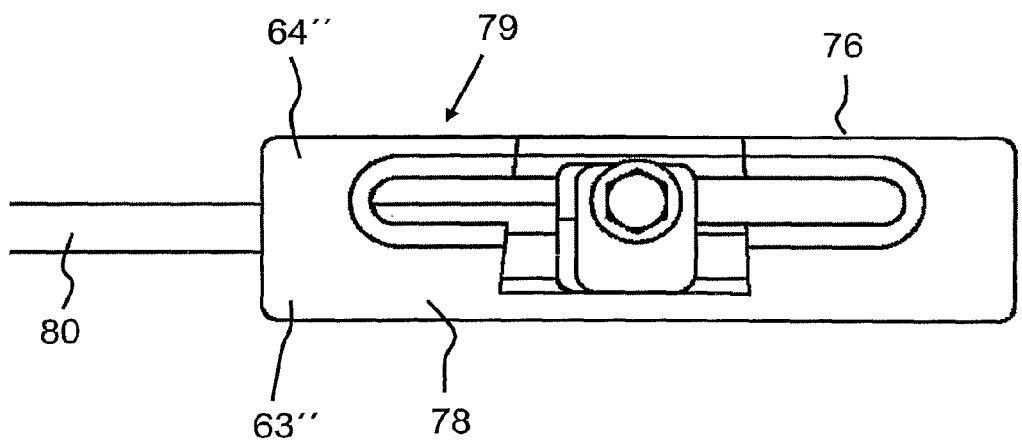
FIG. 71b: Side view of the longer side of the pre-trial implant 79 having a frame 76 and a positioning bar 80, with a carriage body 78, and a superior bearing surface 63" and an inferior bearing surface 64"
Figure 72A:
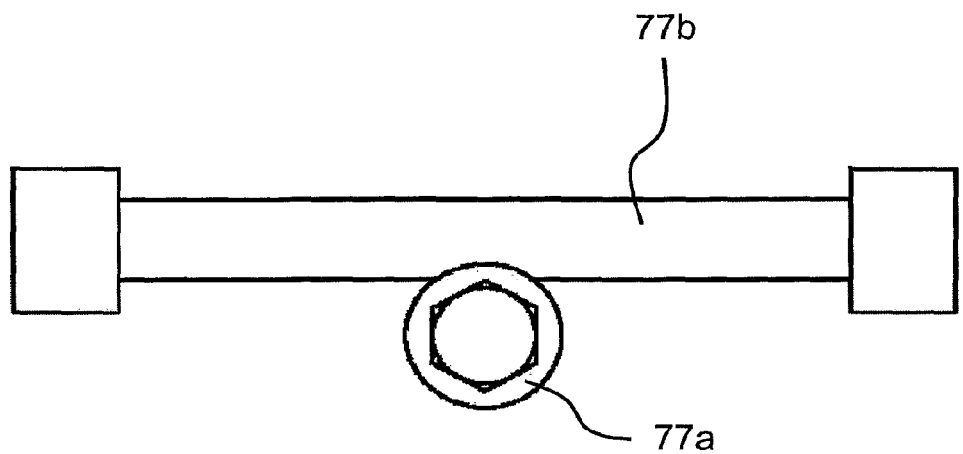
FIG. 72a: Side view of FIG. 71a as an X-ray image with the X-ray-visible spindles 77a and 77b.
Figure 72B:
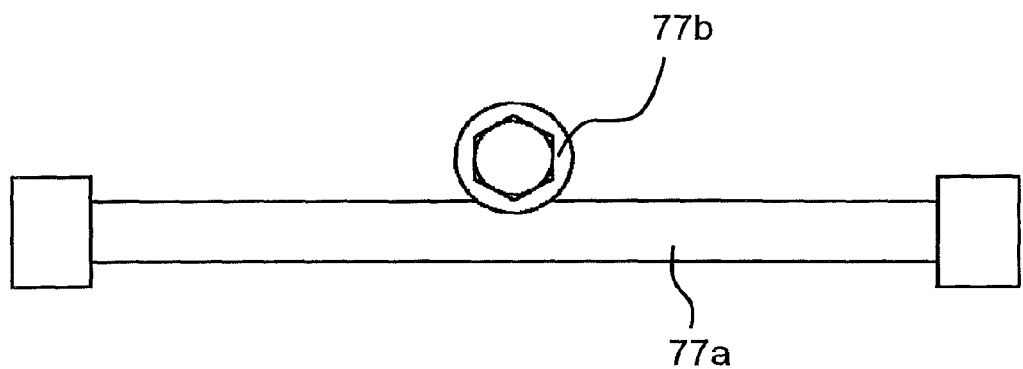
FIG. 72b: Side view of FIG. 71b as an X-ray image with the X-ray-visible spindles 77a and 77b.
Figure 73:
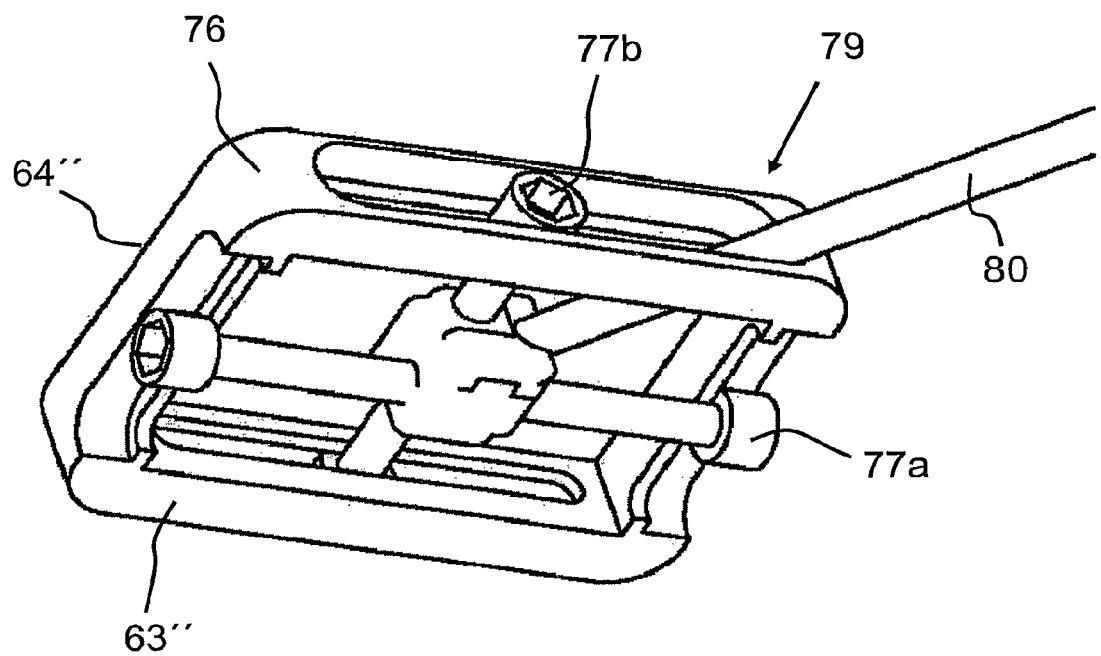
FIG. 73: Oblique view of a pre-trial implant 79 having a frame 76 and a positioning bar 80, and a superior bearing surface 63" and an inferior bearing surface 64" and with the X-ray-visible spindles 77a and 77b.
Figure 74:
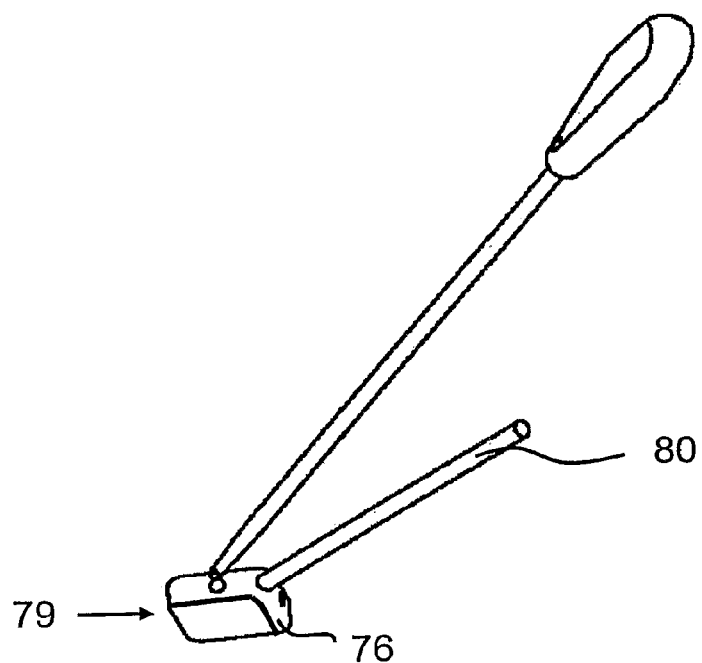
FIG. 74: Oblique view of a pre-trial implant 79 having a frame 76 and a positioning bar 80.
Figure 75:
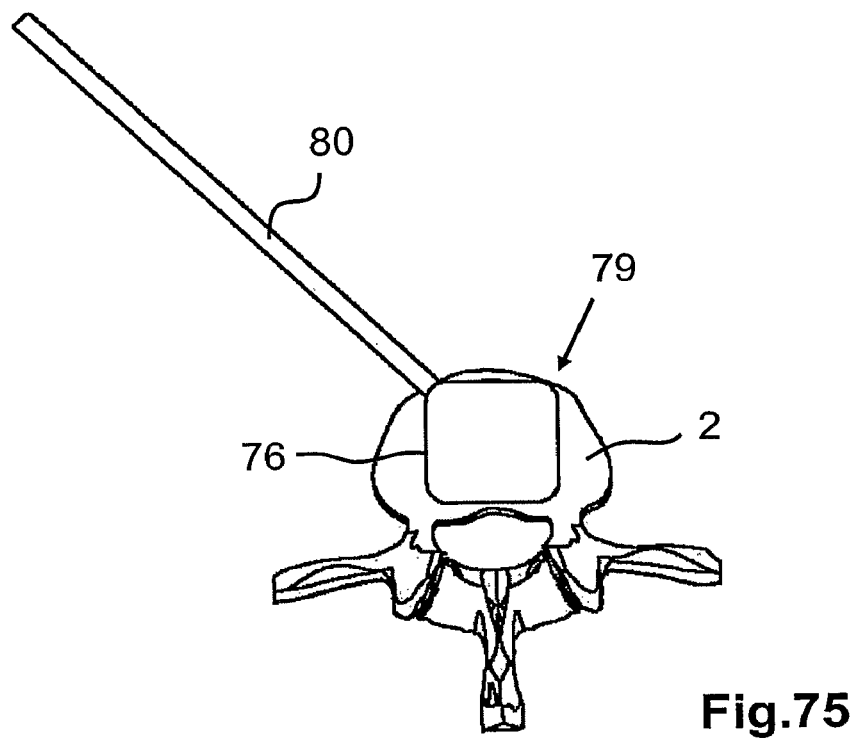
FIG. 75: Pre-trial implant 79 having a frame 76 and a positioning bar 80 on an inferior vertebra 2.
Figure 76A:
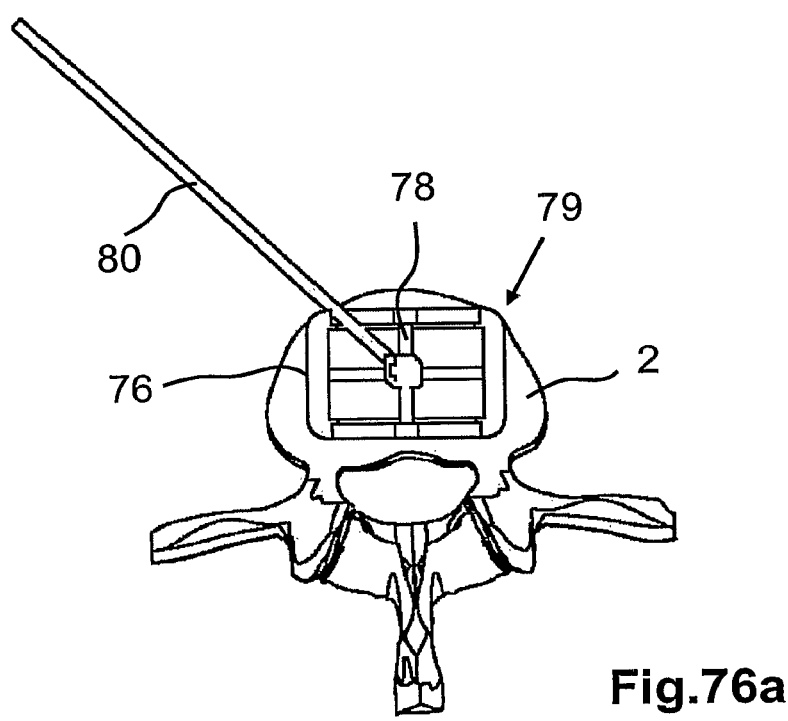
FIG. 76a: Sectional diagram of a pre-trial implant 79 having a frame 76 and a positioning bar 80 and a carriage body 78 on an inferior vertebra 2, surrounded by tissue.
Figure 77A:
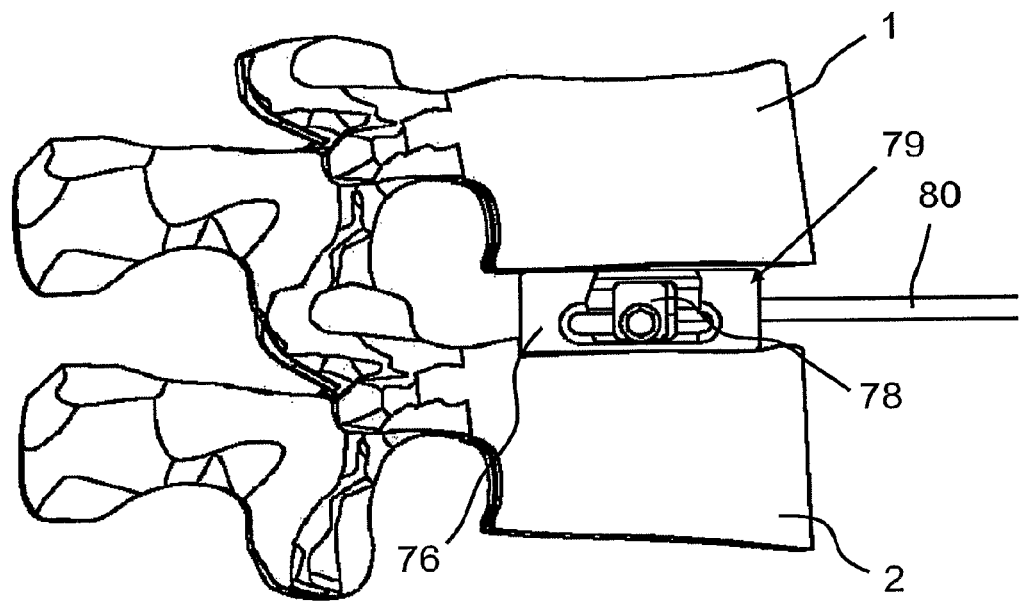
FIG. 77a: Side view of a pre-trial implant 79 having a frame 76 and a positioning bar 80 and a carriage body 78 between a superior vertebra 1 and an inferior vertebra 2.
Figure 77B:
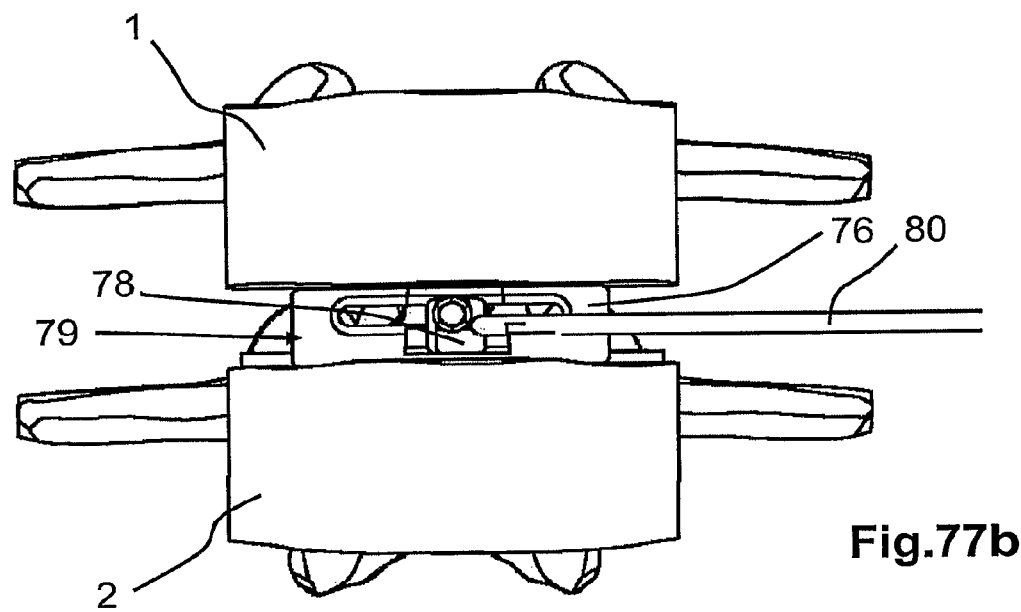
FIG. 77b: Front view of a pre-trial implant 79 having a frame 76 and a positioning bar 80 and a carriage body 78 between a superior vertebra 1 and an inferior vertebra 2.
Figure 78A:
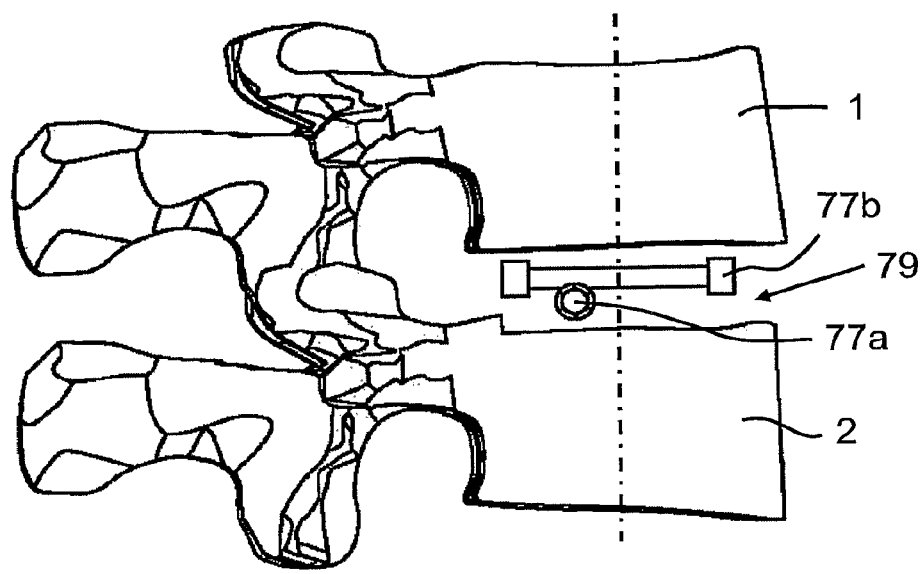
FIG. 78a: Side view of a pre-trial implant 79 as an X-ray representation with the X-ray-visible spindles 77a and 77b between a superior vertebra 1 and an inferior vertebra 2, the mid-line (dashed) not yet having been reached.
Figure 78B:
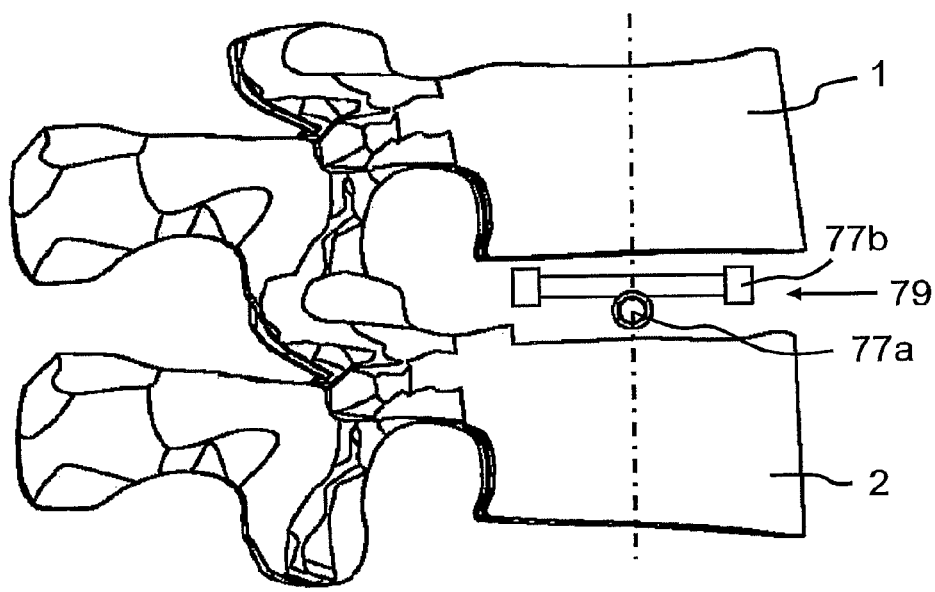
FIG. 78b: Side view of a pre-trial implant 79 as an X-ray representation with the X-ray-visible spindles 77a and 77b between a superior vertebra 1 and an inferior vertebra 2, with which the spindle 77a is aligned exactly with the mid-line (dashed)

The final implant 5, 6, 7 is now inserted (FIG. 67).

There are 2 variants.

In the first one, the inlay is inserted only after the upper and lower implant parts 5 and 7 have been pushed into the bone.

The insertion of an intervertebral implant 5, 6, 7 (FIG. 10-14) with subsequent insertion of the inlay 6 is effected using an instrument 16 (FIG. 97).

Figure 33:
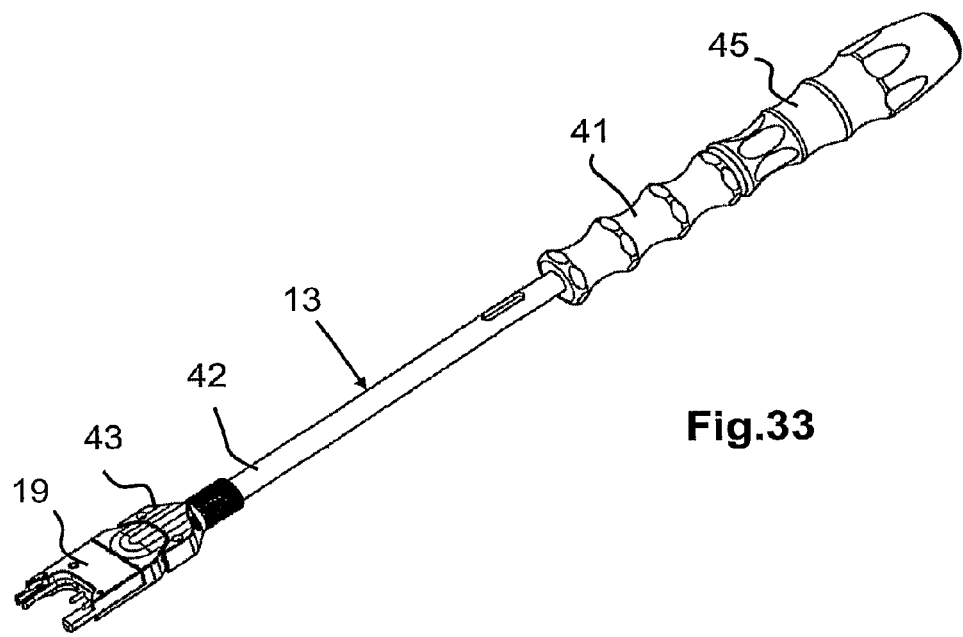
FIG. 33: Inserter 13 with actuating handle 41, with hand grip 45, with rod 42, with locking part 43 and with collet 19.
Figure 34:
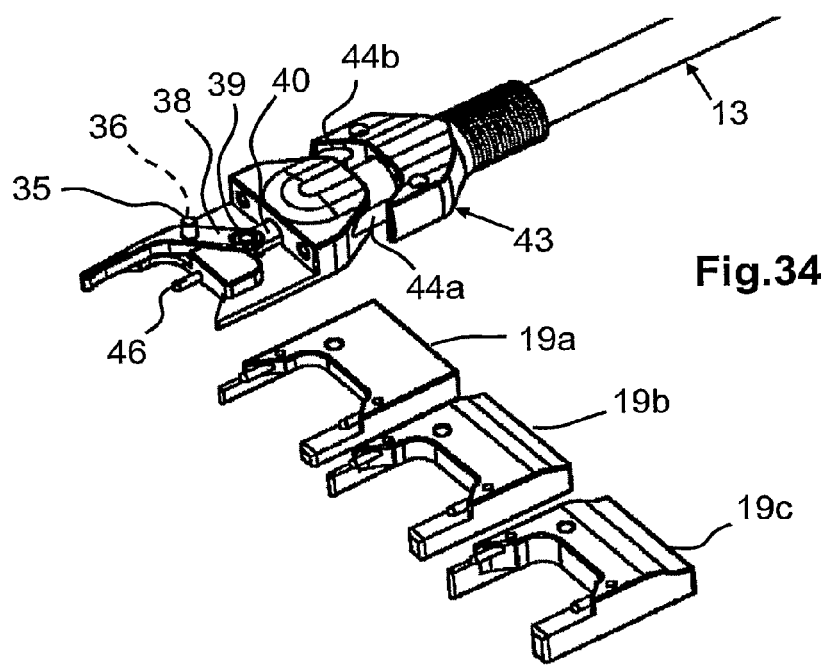
FIG. 34: Inserter 13 with locking part 43 and guide pins 44a,b with bearing pin 35 in the bearing pin axle 36, with lever 38 for holding the implant, with insert pin for superior plate 46 with joint pin 39 and actuating bar 40, and a set of collets 19a-c, with the preferred heights 10, 12, 14 mm, which are interlocked with the implant.
Figure 35:
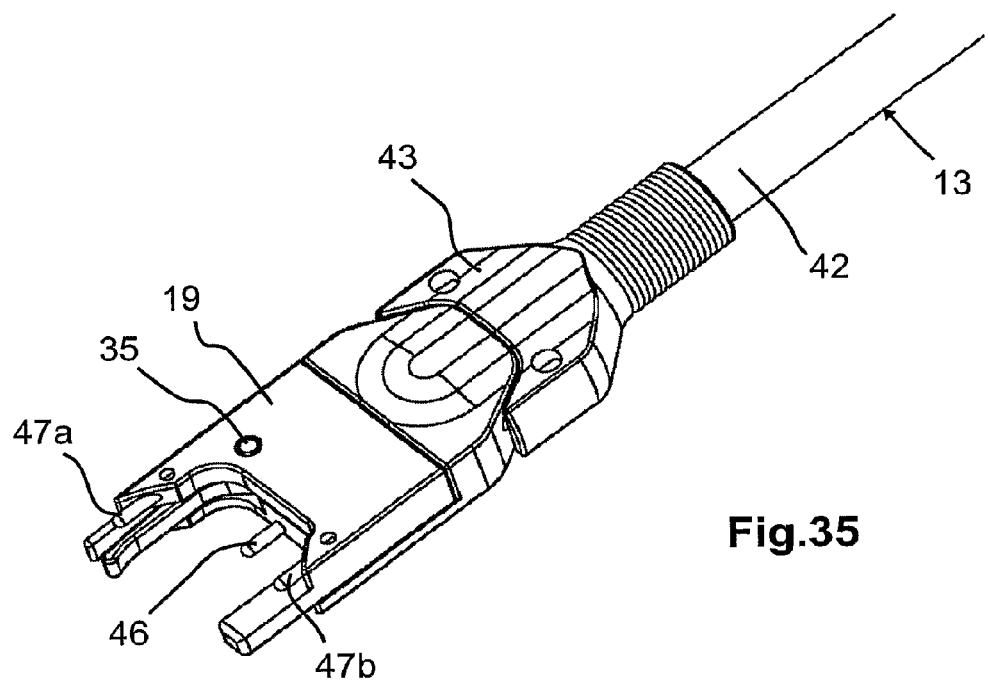
FIG. 35: Inserter 13 within locking part 43 and with collet 19, with bearing pin 35, insert pins for inferior plate 47a,b and insert pin for superior plate 46. An individual collet 19a-c (cf.
Figure 36:
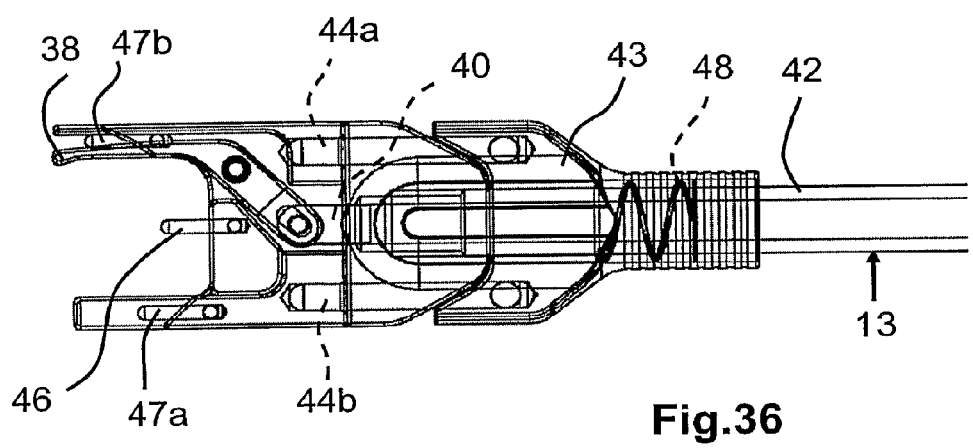
FIG. 36: Inserter 13 with locking part 43, spring 48, with lever 38 for holding the implant, actuating bar 40, with insert pin 46 for the superior implant plate 5, with insert pins 47a,b for the inferior implant plate 7 (not shown)
Figure 37:
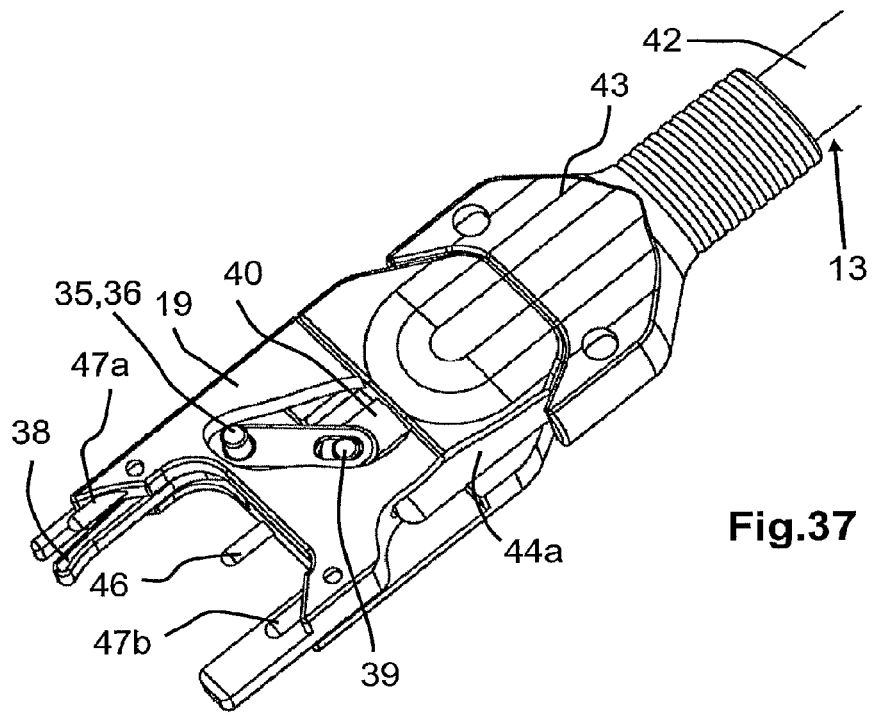
FIG. 37: Inserter 13 with rod 42 with locking part 43 and with collet 19, with bearing pin 35 in the bearing pin axle 36, with lever 38 for holding the implant, with joint pin 39 and actuating bar 40 with insert pin 46 for the superior implant plate 5, with insert pins 47a,b for the inferior implant plate 7 (not shown)
Figure 38:
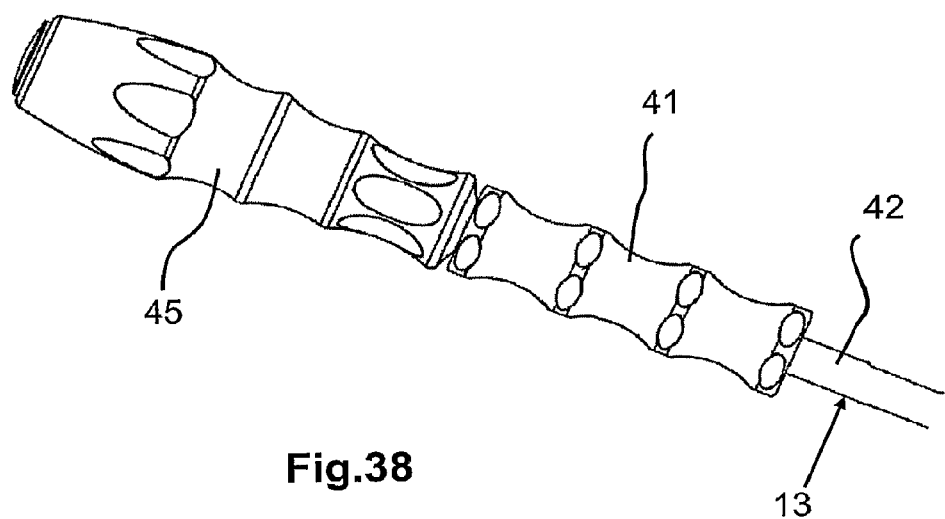
FIG. 38: Inserter 13 with actuating handle 41, with hand grip 45, with rod 42.
Figure 39:
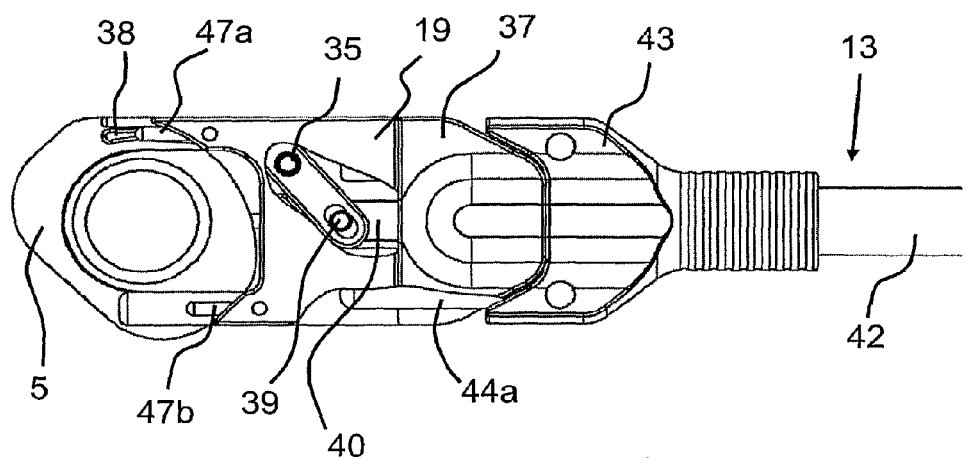
FIG. 39: Inserter 13 in the unlocked position, rod 42 with locking part 43 and with collet 19, with bearing pin 35, distance piece 37, with lever 38 for holding the implant, with joint pin 39 and actuating bar 40, and a collet 19 with inserted superior implant plate 5, with insert pins 47a,b for the inferior implant plate 7 (cf.
Figure 40:
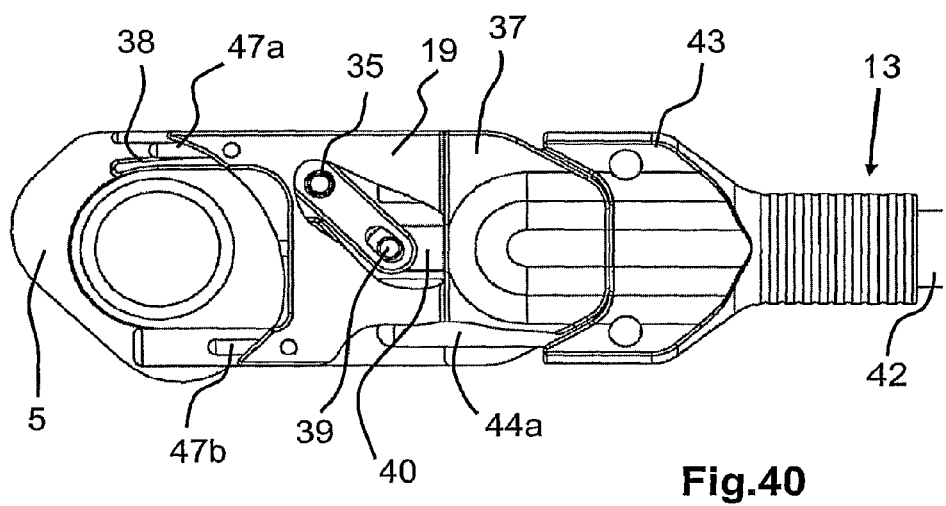
FIG. 40: Inserter 13 in the locked position, rod 42 with locking part 43 and with collet 19, with bearing pin 35, distance piece 37, with lever 38 for holding the implant, with joint pin 39 and actuating bar 40 and a collet 19, with inserted superior implant plate 5, with insert pins 47a,b for the inferior implant plate 7 (not shown)
Figure 41:
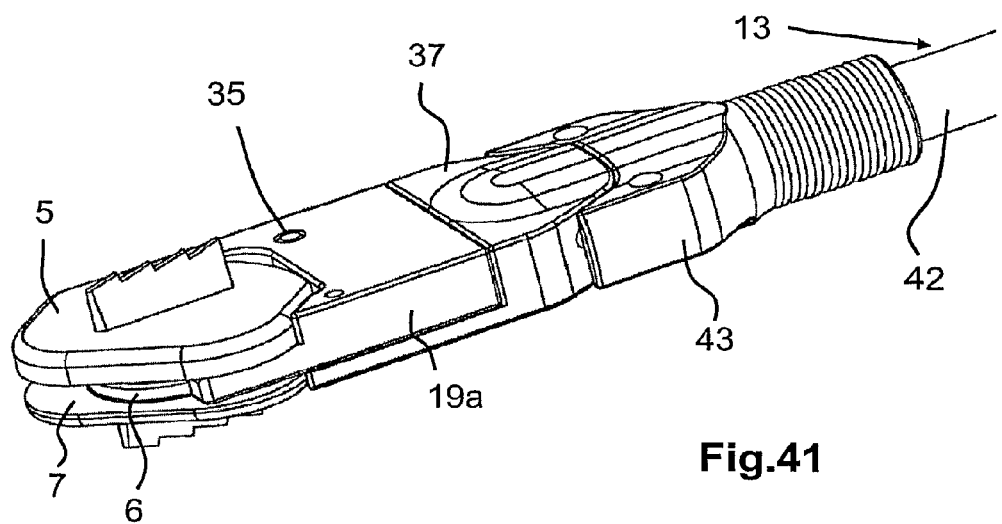
FIG. 41)
Figure 42:
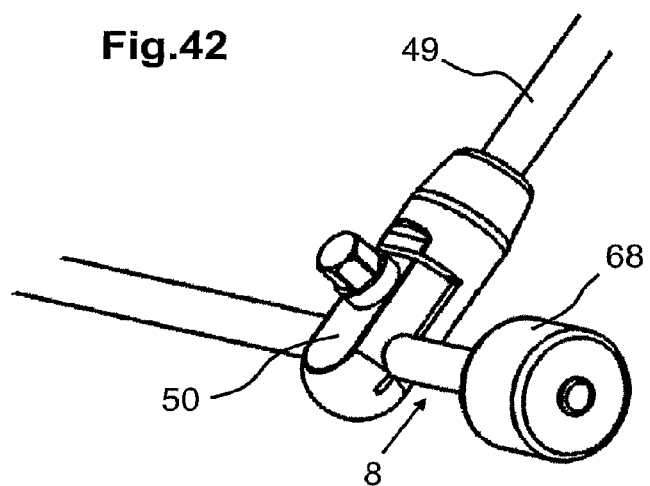
FIG. 42: Handle 8 with impact head 68 for the trial implant with support rod 49 for attachment on Synframe or on another support device, with a clamping device 50.
Figure 43:
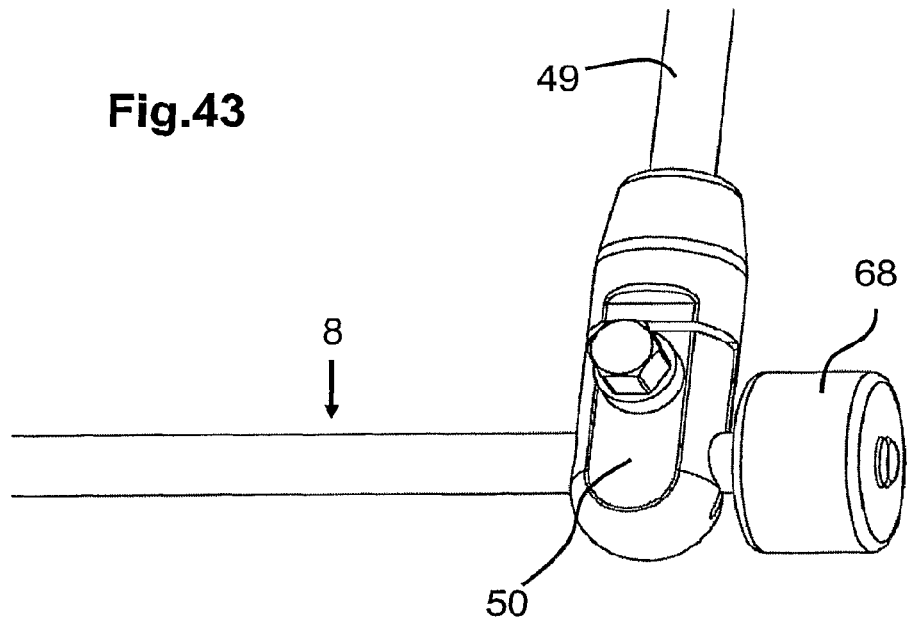
FIG. 43: Handle 8 for the trial implant with support rod 49 for attachment on Synframe or on another support device, with a clamping device 50 in the end position, before the impact head 68.

In the second "all-in-one" variant, the entire implant is inserted immediately. The insertion of an intervertebral implant 5, 6, 7 all in one is effected using an instrument 13 (FIG. 33-35).

When the implant fits correctly, which is likewise monitored by means of X-rays, the struts 20, 21 according to the invention (FIGS. 67, 81, 82) are removed and the abdominal cavity is closed again by a conventional surgical method.

The spirit and scope of the appended claims should not be limited to the description of the preferred versions contained herein. Many modifications may be made in the techniques and structures described and illustrated herein without departing from the spirit and scope of the invention. Accordingly, the techniques and structures described and illustrated herein should be understood to be illustrative only and not limiting upon the scope of the present invention. Particularly for the U.S. national stage, it should be understood that the original presentation of internation-style claims and their subsequent replacement in entry to U.S. national phase should not invoke any limitation upon the scope of the claimed invention as defined by the U.S. claims presented for examination, including known equivalents and unforeseeable equivalents at the time of filing of this application.

What is claimed is:

1. A trial implant configured to prepare an intervertebral space for insertion of an intervertebral disc prosthesis, the trial implant comprising:
 a trial implant body defining a superior bearing surface, an inferior bearing surface that is opposite the superior bearing surface along a vertical direction, an anterior end, a posterior end spaced from the anterior end along an anterior-posterior direction that is substantially perpendicular to the vertical direction, and opposed lateral sides spaced apart with respect to each other, and each of the anterior and posterior ends define a midpoint located between the opposed lateral sides, the midpoints lying on an anterior-posterior axis that is aligned with the anterior-posterior direction, and
 the trial implant body further defining a superior guide slot that extends into the superior bearing surface, an inferior guide slot that extends into the inferior bearing surface, a superior bottom surface, and an inferior bottom surface, the superior and inferior bottom surfaces being spaced from each bearing surface along the vertical direction, wherein 1) each guide slot extends from the respective bearing surfaces to the respective bottom surfaces such that the guide slots do not extend entirely through the trial implant body, and 2) each guide slot is elongate along a respective guide slot axis that is perpendicular with respect to the vertical direction and is oblique with respect to the anterior-posterior axis, wherein the at least one guide slot is configured to receive a guide along the guide slot axis.

2. The trial implant according to claim 1, wherein each of the at least one guide slot is configured to guide a chisel, wherein the chisel is displaceable relative to the guide.

3. The trial implant according to claim 1, wherein the at least one guide slot is a superior guide slot that extends into the superior bearing surface and an inferior guide slot that extends into the inferior bearing surface.

4. The trial implant according to claim 1, further comprising at least one sighting slot in each of the superior and inferior bearing surfaces configured so that when the trial implant is inserted into the intervertebral space defined between adjacent vertebrae, a position of each sighting slot relative to the vertebrae is detectable by X-rays.

5. The trial implant according to claim 4, wherein the at least one sighting slot is disposed at an angle relative to the respective at least one guide slot.

6. The trial implant according to claim 4, wherein the at least one sighting slot is two sighting slots, the two sighting slots being oriented at a right angle relative to one another.

7. The trial implant according to claim 1, wherein the trial implant is at least partly made of X-ray-opaque or X-ray-visible material.

8. The trial implant according to claim 4, wherein the at least one sighting slot is filled with X-ray-transparent material.

9. The trial implant according to claim 1, wherein the trial implant is at least partly made of X-ray-transparent material, and the trial implant includes X-ray-opaque or X-ray-visible inlays.

10. The trial implant according to claim 8, wherein least one guide slot is X-ray-visible.

11. The trial implant according to claim 1, wherein the trial implant body defines a lateral surface that includes at least one impact hollow.

12. The trial implant according to claim 1, further comprising a guide shank configured to engage an impact shank or handle.

13. The trial implant according claim 1, further comprising an adjustable stop that is configured to limit a depth of insertion of the trial implant into the intervertebral space.

14. The trial implant claim 1, wherein the trial implant is configured to be inserted in the intervertebral space at about 45° relative to the anterior-posterior direction.

15. An implant configured to be inserted as an intervertebral disc prosthesis into a prepared intervertebral space, the implant comprising
 an implant body defining a superior bearing surface and an inferior bearing surface that is opposite the superior bearing surface along a vertical direction; and
 at least one guide slot that extends into at least one of the superior and inferior bearing surfaces, the at least one guide slot being elongate along a central guide slot axis and the implant body defines a bottom surface of the at least one slot that is spaced from the respective bearing surface along the vertical direction, and at least one slot wall that extends from the bottom surface to the respective bearing surface, the implant body further defining a first edge where the at least one slot wall intersects the bottom surface and a second edge where the at least slot wall intersects the respective bearing surface and the second edge is disposed closer to the central guide slot axis than the first edge, wherein the at least one guide slot is configured to receive a guide such that the received guide is nondisplaceable along the vertical direction.

16. The implant according to claim 15, wherein the at least one guide slot is configured to guide a chisel, the chisel is displaceable relative to the guide.

17. The implant according to claim 15, wherein the at least one guide slot is a superior guide slot that extends into the superior bearing surface and an inferior guide slot that extends into the inferior bearing surface.

18. The implant according to claim 15, further comprising at least one sighting slot in each of the superior and inferior bearing surfaces configured so that when the implant is inserted into an intervertebral space a position of each of the at least one sighting slot relative to the vertebrae is detectable by X-rays.

19. The implant according to claim 18, the at least one sighting slot is disposed at that angle relative to the respective at least one guide slot.

20. The implant according to claim 15, wherein the at least one sighting slot includes two sighting slots, the two sighting slots being oriented at a right angle relative to one another.

21. The implant according to claim 15, wherein the implant is at least partly made of X-ray-opaque or X-ray-visible material.

22. The implant according to claim 15, wherein the implant is at least partly made of X-ray-transparent material, and the implant includes X-ray-opaque or X-ray-visible inlays.

23. The implant according to claim 19, wherein the at least one guide slot are X-ray-visible.

24. The implant according to claim 15, wherein the implant defines a lateral surface that includes at least one impact hollow.

25. The implant according to claim 15, further comprising a removable guide shank configured to engage an impact shank or handle of the implant.

26. The implant according to claim 15, further comprising an adjustable and removable stop that is configured to limit an insertion of the implant into the intervertebral space.

27. The implant according to claim 15, further comprising at least one anchorage keel carried by the implant, wherein the at least one anchorage keel protrudes from at least one of the superior and inferior bearing surfaces.

28. The implant according to claim 27, wherein the at least one anchorage keel is lockable in the at least one guide slot.

29. The implant according to claim 15, wherein the at least one guide slot is in the form of a substantially trapezoidal guide.

30. The implant according to claim 28, further comprising a tapped hole that is configured to receive a stop screw that is configured to stop a trapezoidal socket of the keel.

31. The implant according to claim 27, further comprising at least one anchorage keel that protrudes from each of the superior and inferior bearing surfaces, and the at least one anchorage keel is in the form of a chisel.

32. The implant according to claim 15, wherein the chisel defines a passage in a vertebra when the implant in disposed in the intervertebral space and the chisel is advanced into the vertebra.

33. The implant according to claim 15, wherein the implant is configured to be inserted between two vertebrae at about 45° relative to a medial plane.

34. The implant according to claim 15, wherein an anchorage keel is attached to a rotation plate which is rotatably and lockably mounted on at least one of the bearing surfaces.

35. The implant according to claim 34, further comprising a slot that is configured to receive a clamping screw that is configured to be tightened in a tapped hole in the rotation plate, the slot extends along a slot axis that is substantially parallel to at least one of the bearing surfaces.

36. The implant according to claim 25, wherein the impact shank defines a proximal end and a distal end that is opposite the proximal end, the impact shank includes a coupling piece at the proximal end, the coupling piece is configured to transmit force to the impact shank, the coupling piece has two locks which act separately from one another and provide a frictional or interlocking connection and at least one of which is remotely detachable, and the two locks can each transmit either a torque or an axial force.

37. The implant according to claim 36, wherein the impact shank includes an impact head at the distal end, the impact head defines impact surfaces in a distal direction as well as in a proximal direction.

38. The implant according to claim 25, wherein the impact shank defines a proximal end and an opposed distal end, and includes a detachable and displaceable support rod which can be fixed to the impact shank by a lockable clamping device.

39. The implant according to claim 15, further comprising an adjustable stop, wherein the adjustable stop has a captive stopper body on an adjusting screw, and defines a bore that extends into the captive stopper body, the adjusting screw configured to be received in the bore, the adjusting screw defines a proximal end and an opposed distal end, the proximal end of the adjusting screw defines, an external diameter that is larger than a cross-sectional dimension of the bore in the stopper body, and the adjusting screw includes an actuator at the distal end, the actuator defining an external diameter that is larger than the cross-sectional dimension of the bore.

40. The implant according to claim 39, further comprising a removable guide shank configured to be coupled to an impact shank, wherein the adjustable stop is arranged directly adjacent to the guide shank to stop excess impact force from the impact shank directly at the guide shank.

41. The implant according to claim 39, further comprising a removable guide shank configured to be coupled to an impact shank, wherein the adjustable stop is arranged directly adjacent to the guide shank, and the adjustable stop defines a bore that is configured to receive the guide shank.

42. The implant according to claim 39, wherein the adjustable stop defines a proximal stop side and an opposed distal stop side, the adjustable stop further defines a slot-like recess at the proximal stop side and, in a tapped-in state, the recess configured so that the adjustable stop is guided in a normal direction relative to the bearing surfaces.

43. A kit comprising:
an implant according to claim 15; and
a chisel including a chisel blade and a chisel shank that is coupled to the chisel implant, the chisel shank defining a first end and a second end, the chisel shank including an impact head at the second end, and the chisel shank is connected to a displaceable guide that is configured to be received in at least one of the guide slots.

44. An intervertebral implant configured for insertion into an intervertebral space along an anterior-oblique direction, the intervertebral implant including an anterior end and a posterior end that is spaced from the anterior end along an anterior-posterior direction that is angularly offset with respect to the anterior-oblique insertion direction, the intervertebral implant comprising:
a first implant plate;
a second implant plate spaced apart from the first implant along a vertical direction that is perpendicular to the anterior-posterior direction, and each of the first and second implant plates include respective lateral ends spaced from each other along a lateral direction that is perpendicular to the anterior-posterior direction and the vertical direction;
an inlay that is configured to be disposed between the first implant plate and the second implant plate; and
at least one anchorage keel that protrudes from at least one of the first implant plate and the second implant plate along the vertical direction away from the other of the first and second implant plates, wherein the at least one anchorage keel defines a keel body elongate along a keel axis, the keel body defining a leading end and a trailing end spaced apart from the leading end along the keel axis, wherein the keel body extends between the leading end and the trailing end, and the keel axis is oriented at about 45° relative to the anterior-posterior and lateral directions, such that when the intervertebral implant is inserted into the intervertebral space, the keel axis is aligned with the anterior-oblique direction,
wherein one of the first and second implant plates includes a recess, the recess having an open end and a closed end opposed to the closed end along a recess axis that extends along the anterior-oblique direction so as to be aligned with the keel axis.

45. The intervertebral implant according to claim 44, wherein the at least one anchorage keel defines a base supported by the first implant plate, and a free end spaced apart from the base along the first direction, wherein the free end is configured to face the upper vertebra when the intervertebral implant is disposed in the intervertebral space, and the at least one anchorage keel includes teeth at the free end.

46. The intervertebral implant according to claim 45, wherein each of the teeth defines a distal flank, and an opposed proximal flank, the proximal flank defining a proximal inclination relative to the first implant plate, the distal flank defining a distal inclination relative to the first implant plate, and the distal inclination is shallower than the proximal inclination to facilitate insertion of the at least one anchorage keel in the vertebra along the insertion direction, and to hinder removal of the at least one anchorage keel from the vertebra.

47. The intervertebral implant according to claim 44, wherein the intervertebral implant is at least partly coated with a titanium foam or titanium granules.

48. The intervertebral implant according to claim 44, wherein the at least one anchorage keel is a first anchorage keel, the keel body is a first keel body, and the keel axis is a first keel axis, wherein the intervertebral implant further comprises a second anchorage keel that protrudes from the second implant plate along the vertical direction away from the second implant plate, and the second anchorage keel defines a second keel body elongate along a second keel axis, a second leading end, and a second trailing end spaced apart from the second leading end along the second keel axis, the second keel body extending between the second leading and trailing ends, the second keel axis angularly offset relative to the anterior-posterior direction, wherein when the implant is inserted into the intervertebral space, the second keel axis is aligned with the insertion direction.

49. The implant according to claim 1, wherein the at least one guide slot is configured to receive a guide such that at least a portion of the guide received in the at least one guide slot is nondisplaceable along the vertical direction.

50. The implant according to claim 49, wherein the at least one guide slot is configured so that the received guide is moveable through an entirety of the guide slot along the guide slot axis in A) a first direction that is aligned with the guide slot axis, and B) a second direction that is opposite to the first direction.

51. The implant according to claim 15, wherein the implant body defines an anterior end and a posterior end that is spaced from the anterior end along an anterior-posterior direction that is substantially perpendicular to the vertical direction, wherein the at least one guide slot is elongate along a guide slot axis that is oblique with respect to the anterior-posterior direction.

52. The implant according to claim 15, wherein the at least one guide slot is configured so that the received guide is moveable through an entirety of the guide slot along the guide slot axis in A) a first direction that is aligned with the guide slot axis, and B) a second direction that is opposite to the first direction.

53. The trial implant according to claim 1, wherein the at least one guide slot is elongate linearly along the at least one of the superior and inferior bearing surfaces.

54. The trial implant according to claim 1, wherein the guide slot axis is perpendicular the vertical direction.

55. The intervertebral implant according to claim 1, wherein the opposed lateral sides that are spaced apart with respect to each other along a lateral direction that is perpendicular to the anterior-oblique direction and the vertical direction, and the opposed lateral sides extend from the anterior end toward the posterior along the anterior-oblique direction.

56. The intervertebral implant according to claim 44, wherein the inlay is elongate along an inlay axis, wherein when the inlay is disposed between the first and second implant plates and the inlay axis is parallel to the anterior-oblique direction.

57. The trail implant according to claim 1 wherein the at least one guide slot extends continuously along at least a majority of the respective superior and inferior bearing surfaces.

58. The implant according to claim 15 wherein the at least one guide slot extends continuously along at least a majority of the respective superior and inferior bearing surfaces.

59. The implant according to claim 51, wherein the implant body defines opposed lateral sides that are spaced apart with respect to each other along a lateral direction that is perpendicular to the anterior-posterior direction and the vertical direction, and the opposed lateral sides extend from the anterior end toward the posterior along the anterior-posterior direction.

60. The intervertebral implant according to claim 44, wherein the inlay is disposed in the recess.

61. The intervertebral implant according to claim 44, wherein the lateral ends of the first implant plate extend from the anterior end toward the posterior end substantially along the anterior-posterior direction.

62. The intervertebral implant according to claim 61, wherein the lateral ends of the second implant plate extend from the anterior end toward the posterior end substantially along the anterior-posterior direction.

* * * * *